(12) United States Patent
Ramachandran

(10) Patent No.: US 8,126,299 B2
(45) Date of Patent: Feb. 28, 2012

(54) PRODUCTION OF OPTICAL PULSES AT A DESIRED WAVELENGTH UTILIZING HIGHER-ORDER-MODE (HOM) FIBER

(75) Inventor: Slddharth Ramachandran, Hoboken, NJ (US)

(73) Assignee: OFS Fitel, LLC, Norcross, GA (US)

( * ) Notice: Subject to any disclaimer, the term of this patent is extended or adjusted under 35 U.S.C. 154(b) by 396 days.

(21) Appl. No.: 12/288,206

(22) Filed: Oct. 17, 2008

(65) Prior Publication Data

US 2010/0054661 A1   Mar. 4, 2010

Related U.S. Application Data

(63) Continuation of application No. 11/977,918, filed on Oct. 26, 2007, now abandoned.

(60) Provisional application No. 60/863,082, filed on Oct. 26, 2006, provisional application No. 60/896,357, filed on Mar. 22, 2007.

(51) Int. Cl.
| | |
|---|---|
| *G02B 6/26* | (2006.01) |
| *G02B 6/42* | (2006.01) |
| *G02B 6/00* | (2006.01) |
| *H01S 3/30* | (2006.01) |
| *H01S 3/10* | (2006.01) |
| *G02F 1/35* | (2006.01) |
| *G02F 2/02* | (2006.01) |

(52) U.S. Cl. ............. 385/28; 385/122; 372/6; 372/21; 372/23; 359/327

(58) Field of Classification Search .............. 385/28, 385/122; 372/6, 20, 21, 23, 25; 359/326, 359/327

See application file for complete search history.

(56) References Cited

U.S. PATENT DOCUMENTS

| | | | |
|---|---|---|---|
| 6,400,866 B2 * | 6/2002 | Ranka et al. ............. 385/28 |
| 6,813,429 B2 | 11/2004 | Price et al. | |
| 6,856,737 B1 | 2/2005 | Parker et al. | |
| 2005/0163426 A1 * | 7/2005 | Fermann et al. ............. 385/37 |
| 2005/0265407 A1 * | 12/2005 | Braun et al. ............. 372/30 |
| 2006/0039661 A1 * | 2/2006 | Ruilier et al. ............. 385/123 |
| 2006/0198588 A1 * | 9/2006 | Kuksenkov et al. ........... 385/122 |
| 2007/0206910 A1 | 9/2007 | Ramachandran | |

* cited by examiner

Primary Examiner — Ryan Lepisto
Assistant Examiner — Robert Tavlykaev
(74) Attorney, Agent, or Firm — Law Office of Wendy W. Koba, Esq.

(57) ABSTRACT

An apparatus and method for producing optical pulses of a desired wavelength utilizes a section of higher-order-mode (HOM) fiber to receive input optical pulses at a first wavelength, and thereafter produce output optical pulses at the desired wavelength through soliton self-frequency shifting (SSFS) or Cherenkov radiation. The HOM fiber is configured to exhibit a large positive dispersion and effective area at wavelengths less than 1300 nm.

34 Claims, 24 Drawing Sheets

EXPERIMENTAL

SIMULATION

US 8,126,299 B2

PRODUCTION OF OPTICAL PULSES AT A DESIRED WAVELENGTH UTILIZING HIGHER-ORDER-MODE (HOM) FIBER

CROSS-REFERENCE TO RELATED APPLICATIONS

This application is a continuation of U.S. Ser. No. 11/977,918, filed Oct. 26, 2007, now abondoned which claims the benefit of U.S. Provisional Applications 60/863,082, filed Oct. 26, 2006, and 60/896,357, filed Mar. 22, 2007, both provisional applications herein incorporated by reference.

FIELD OF THE INVENTION

The present invention relates to the production of optical pulses at a desired wavelength using higher-order-mode fibers and, more particular, to the utilization of HOM fiber with a positive dispersion and large effective area sufficient to generate high energy, short pulses at wavelengths below 1300 nm, considered useful for numerous applications.

BACKGROUND OF THE INVENTION

Mode-locked femtosecond fiber lasers at 1030 nm and 1550 nm have been improving significantly in the last several years, particularly with respect to the achievable output pulse energy (increasing from 1 to ~10 nJ). Even higher pulse energy can be achieved in femtosecond fiber sources based on fiber chirped pulse amplification. However, femtosecond fiber sources, including lasers, have seen only limited applications in multiphoton imaging. The main reason is that they offer very limited wavelength tunability (tens of nanometer at best), severely restricting the applicability of these lasers, making them only suitable for some special purposes. In addition, existing femtosecond fiber sources at high pulse energy (>1 nJ) are not truly "all fiber," i.e., the output is not delivered through a single mode optical fiber. Thus, additional setup (typically involving free-space optics) must be used to deliver the pulses to imaging apparatus, partially negating the advantages of the fiber source.

Reports have demonstrated the possibility of propagating femtosecond IR pulses through a large core optical fiber at intensities high enough (~1 nJ) for multiphoton imaging. In addition, a special HOM fiber that is capable of delivering energetic femtosecond pulses (~1 nJ) has been demonstrated. However, both of these fibers have normal dispersion, and both require a free-space grating pair for dispersion compensation. Not only is such a grating pair lossy and complicated to align, it needs careful adjustment for varying fiber length, output wavelength, and output pulse energy, and falls short of the requirement for most biomedical research labs and future clinical applications.

Femtosecond fiber sources are highly robust and cost effective. However, energetic femtosecond fiber sources at 1300 nm prove to be very difficult to obtain because of the characteristics of the fluoride fiber based gain medium. Such difficulties are exemplified by the huge performance and cost gap between optical amplifiers (essentially lasers without the cavity mirrors) at these wavelengths. For example, fiber amplifiers at 1300 nm are expensive (~$31 k) and have limited output power (~60 mW) and narrow spectral bandwidth (~20 nm). This is in sharp contrast to fiber amplifiers at 1030 nm and 1550 nm, where high power amplifiers (~2 W) will only cost ~$25 k and has a spectral bandwidth of ~40 nm. Thus, the route that follows the development of fiber sources at 1030 and 1550 nm is unlikely to be productive at 1300 nm. An alternative approach must be taken in order to create a femtosecond fiber source at 1300 nm that has a comparable performance and cost to that of the fiber sources at 1030 and 1550 nm.

Higher-order-mode (HOM) fiber has attracted significant interest recently, due to the freedom it provides to design unique dispersion characteristics in all-solid (i.e., non-"holey") silica fiber.

The 'wavelength tunability' of femtosecond optical sources has been extensively studied within the phenomenon of soliton self-frequency shift (SSFS), in which Raman self-pumping continuously transfers energy from higher to lower frequencies within an optical fiber. SSFS has been exploited over the last decade in order to fabricate widely frequency-tunable, femtosecond pulse sources with fiber delivery. Since anomalous (positive) dispersion ($\beta_2<0$ or $D>0$) is required for the generation and maintenance of solitons, early sources that made use of SSFS for wavelength tuning were restricted to wavelength regimes >1300 μm, where conventional silica fibers naturally exhibit positive dispersion.

In addition, Cherenkov radiation has been demonstrated in microstructured fibers pumped near their zero-dispersion wavelength. In general, an ideal soliton requires a perfect balance between dispersion and nonlinearity so that energy becomes endlessly confined to a discrete packet—both spectrally and temporally. When perturbations are introduced, this stable solution breaks down, allowing the transfer of energy between the soliton and the disturbance. Such energy transfer occurs most efficiently in fibers for solitons near the zero-dispersion wavelength. The spectral regime to which energy couples most efficiently has been dubbed "Cherenkov radiation" due to an analogous phase matching condition in particle physics. The phenomenon of Cherenkov radiation in fibers is often associated with SSFS as it allows a convenient mechanism for more efficient energy transfer between the soliton and the Cherenkov band. In particular, when the third-order dispersion is negative, SSFS will shift the center frequency of the soliton toward the zero-dispersion wavelength, resulting in efficient energy transfer into the Cherenkov radiation in the normal dispersion regime. The problem of tunability remains an issue for these arrangements capable of creating Cherenkov radiation.

The recent development of index-guided photonic crystal fibers (PCF) and air-core photonic band-gap fibers (PBGF) have relaxed this tunability requirement somewhat, with the ability to design large positive waveguide dispersion and therefore large positive net dispersion in optical fibers at nearly any desired wavelength. This development has allowed for a number of demonstrations of tunable SSFS sources supporting input wavelengths as low as 800 nm in the anomalous dispersion regime.

Unfortunately, the pulse energy required to support stable Raman-shifted solitons below 1300 nm in index-guided PCFs and air-core PBGFs is either on the very low side, a fraction of a nJ for silica-core PCFs, or on the very high side, greater than 100 nJ (requiring an input from an amplified optical system) for air-core PBGFs. The low-energy limit is due to high nonlinearity in the PCF. In order to generate large positive waveguide dispersion to overcome the negative dispersion of the material, the effective area of the fiber core must be reduced. For positive total dispersion at wavelengths less than 1300 nm, this corresponds to an effective area, $A_{\textit{eff}}$, of 2-5 μm², approximately an order of magnitude less than conventional single mode fiber (SMF). The high-energy limit is due to low nonlinearity in the air-core PBGF where the nonlinear index, $n_2$, of air is roughly 1000 times less than that of silica. These extreme ends of nonlinearity dictate the required pulse energy (U) for soliton propagation, which scales as $U \square D \cdot A_{eff}/n_2$. In fact, most microstructure fibers and tapered fibers with positive dispersion are intentionally designed to demonstrate nonlinear optical effects at the lowest possible pulse energy, while air-core PBGFs are often used for applications that require linear propagation, such as pulse delivery.

There are a number of biomedical applications that require femtosecond sources. Although applications requiring a large spectral bandwidth (such as optical coherency tomography) can also be performed using incoherent sources such as superluminscent diodes, techniques based on nonlinear optical effects, such as multiphoton microscopy and endoscopy, almost universally require the high peak power generated by a femtosecond source.

Molecular two-photon excitation (2PE) was theoretically predicted by Maria Goppert-Mayer in 1931. The first experimental demonstration of two-photon absorption, however, came nearly 30 years later, after the technological breakthrough of the invention of the ruby laser in 1960. It was almost another 30 years before the practical application of 2PE for biological imaging was demonstrated at Cornell University in 1990. Once again, this new development was propelled in large part by the rapid technological advances in mode-locked femtosecond lasers. Since then, two-photon laser scanning microscopy has been increasingly applied to cell biology and neurosciences. A number of variations, including three-photon excitation (3PE), second and third harmonic generation imaging, near-field enhanced multiphoton excitation and multiphoton endoscopic imaging, have emerged and further broadened the field, which is currently known as multiphoton microscopy (MPM). Today, MPM is an indispensable tool in biological imaging. Like any nonlinear process, however, multiphoton excitation requires high peak intensities, typically 0.1 to 1 $TW/cm^2$ ($TW=10^{12}$ W). Besides tight spatial focusing, MPM typically requires pulsed excitation sources to provide additional temporal "focusing" so that efficient multiphoton excitation can be obtained at low average power. For example, a femtosecond laser with 100-fs pulse width ($\tau$) at 100 MHz pulse repetition rate (f) will enhance the excitation probability of 2PE by a factor of $10^5$, i.e., the inverse of the duty cycle ($f\tau$). The development of multiphoton imaging depends critically on ultrafast technologies, particularly pulsed excitation source.

Endoscopes play an important role in medical diagnostics by making it possible to visualize tissue at remote internal sites in a minimally invasive fashion. The most common form employs an imaging fiber bundle to provide high quality white light reflection imaging. Laser scanning confocal reflection and fluorescence endoscopes also exist and can provide 3D cellular resolution in tissues. Confocal endoscopes are now becoming available commercially (Optiscan Ltd, Australia, Lucid Inc, Rochester) and are being applied in a number of clinical trials for cancer diagnosis. Multiphoton excitation based endoscopes has attracted significant attention recently. There were a number of advances, including fiber delivery of excitation pulses, miniature scanners, double clad fibers for efficient signal collections, etc. Thus, just like MPM has proven to be a powerful tool in biological imaging, multiphoton endoscopes have great potentials to improve the capability of the existing laser-scanning optical endoscopes. It is quite obvious that a compact, fully electronically controlled, femtosecond system seamlessly integrated with fiber optic delivery is essential for multiphoton endoscopy in medical diagnostics, particularly to biomedical experts who are not trained in lasers and optics.

Perhaps the most promising and successful area in biomedical imaging that showcases the unique advantage of multiphoton excitation is imaging deep into scattering tissues. In the past 5 to 10 years, MPM has greatly improved the penetration depth of optical imaging and proven to be well suited for a variety of imaging applications deep within intact or semi-intact tissues, such as demonstrated in the studies of neuronal activity and anatomy, developing embryos, and tissue morphology and pathology. When compared to one-photon confocal microscopy, a factor of 2 to 3 improvement in penetration depth is obtained in MPM. Nonetheless, despite the heroic effort of employing energetic pulses (~µJ/pulse) produced by a regenerative amplifier, MPM has so far been restricted to less than 1 mm in penetration depth. One promising direction for imaging deep into scattering tissue is to use longer excitation wavelength. Although there is little data for tissue scattering beyond 1.1 µm, the available data at shorter wavelengths clearly indicates the general trend that tissue scattering reduces as one uses longer excitation wavelength. Longer excitation wavelengths are an obvious choice for imaging deep into scattering tissues.

A concern for longer wavelength excitation is water absorption, which is typically the dominant contribution to tissue absorption at near IR. However, a careful examination showed that water absorption at 1270 nm is only approximately twice as high as that between 960 and 1000 nm, a spectral region where multiphoton excitation and imaging has been routinely performed in the past. Although the "diagnostic and therapeutic window," which is in between the absorption regions of the intrinsic molecules and water, extends all the way to ~1300 nm, previous investigations involving multiphoton imaging are almost exclusively carried out within the near IR spectral window of ~700 to 1100 nm, constrained mostly by the availability of the excitation source. Currently, there are only two femtosecond sources at the spectral window of 1200 to 1300 nm, the Cr:Forsterite laser and the optical parametric oscillator (OPO) pumped by a femtosecond Ti:Sapphire (Ti:S) laser. In terms of robustness and easy operation, both sources rank significantly below the Ti:S laser. Thus, the development of a reliable fiber source tunable from 1030 to 1280 nm will open up new opportunities for biomedical imaging, particularly for applications requiring deep tissue penetration.

Shortly after the inception of MPM, mode-locked solid state femtosecond lasers, most commonly the Ti:S lasers, have emerged as the favorite excitation sources to dominate the MPM field today. When compared to earlier ultrafast lasers, e.g., ultrafast dye lasers, the Ti:S lasers are highly robust and flexible. The concurrent development of the mode-locked Ti:S lasers was perhaps the biggest gift for MPM and enabled MPM to rapidly become a valuable instrument for biological research. Nonetheless, the cost, complexity, and the limited potential for integration of the bulk solid state lasers have hampered the widespread applications of MPM in biological research. The fact that a disproportionate number of MPM systems are located in physics and engineering departments, instead of the more biologically oriented institutions, reflects at least in part the practical limitations of the femtosecond pulsed source. Obviously, the requirement of a robust, fiber delivered, and cheap source is even more urgent for multiphoton endoscopy in a clinical environment.

For these reasons, previous work using SSFS below 1300 nm was performed at soliton energies either too low or too high (by at least an order of magnitude) for many practical applications, such as multiphoton imaging, where bulk solid state lasers are currently the mainstay for the excitation source.

The present invention is directed to overcoming these and other deficiencies in the state of the art.

SUMMARY OF THE INVENTION

The present invention relates to a higher-order-mode (HOM) fiber module operable to generate energetic, short output pulses of light at wavelengths amenable to various applications, while also providing a degree of wavelength tunability. In particular, the inventive HOM module includes a section of HOM fiber with anomalous (positive) dispersion and a large effective area, characteristics that create a soliton self-frequency shift sufficient to move an incoming stream of pulses at one wavelength to a stream of pulses at a second, desired wavelength associated with a specific application. These dispersion characteristics have also been found to allow for the creation of soliton Cherenkov radiation at wavelengths below 1300 nm, with usable energy in the range of 1-10 nJ.

Additionally, the HOM fiber module of the present invention provides the ability to compensate the dispersion of an optical pulse that is chirped at its input (chirp of no less than 5.25 fs/nm). It has been found that the HOM module provides a sufficient amount of dispersion to provide a transform-limited pulse at a predetermined location within the HOM fiber such that the pulse undergoes frequency shift by either of the SSFS or Cherenkov effects described above.

In accordance with the present invention, the HOM module comprises an input mode converter (for converting from the conventional $LP_{01}$ mode to a higher-order mode), a section of HOM fiber coupled to the input mode converter for generating the desired self-frequency shift to a desired output wavelength, and (when necessary) an output mode converter (for converting the wavelength-shifted pulses back to the conventional $LP_{01}$ mode or any other desired spatial profile).

In one embodiment, in-fiber long period gratings (LPGs) are used for the input and output mode converters, thus minimizing the amount of optical loss present at the junction between the mode converters and the HOM fiber.

The HOM fiber portion of the module is configured in one embodiment to include a wide, low index ring cladding area, separated from a high index core region by a trench. The index values and dimensions of the ring, trench and core are selected to provide the desired amount of anomalous dispersion and size of the effective area. One set of acceptable values for use in accordance with the present invention is a dispersion on the order of +60 ps/nm-km and an effective area of approximately 44 $\mu m^2$. Another set of acceptable values are defined by the wavelength range within which the dispersion is anomalous (positive), this range being between 10 and 300 nM. Yet another set of acceptable values are defined by the maximum achievable dispersion in the wavelength range of interest, this value ranging from 0 to +3000 ps/nm-km. With respect to the effective area, acceptable values of $A_{eff}$ for the purposes of the present invention range from about 5 to 4000 $\mu m^2$.

The present invention also relates to a method of producing output optical pulses having a desired wavelength. The method includes generating input optical pulses and delivering the input pulses to an HOM fiber module to alter the wavelength of the input optical pulses from the first wavelength to the second, desired wavelength by soliton self-frequency shifting (SSFS) within the HOM fiber module.

In one embodiment, the method can further include converting the spatial mode of the input signal into a higher-order mode at the input of the HOM fiber module, and thereafter reconverting the output of the HOM fiber module back to the original spatial mode or to any other desired mode profile.

It is an advantage of the present invention that the HOM module is capable of achieving these characteristics at wavelengths below 1300 nm, heretofore not accomplished in an all-silica (non-holey) fiber.

Further, the HOM module of the present invention is designed such that the difference between the effective index $n_{eff}$ of the mode in which signal propagation is desired is separated from that of any other guided mode of the fiber by greater than $10^{-5}$, thus providing for enhanced modal stability of the signal.

In one embodiment, the input comprises a single mode fiber (SMF) spliced to the HOM fiber before mode conversion, with the properties of the splice ensuring that signal propagation in the HOM fiber occurs predominantly in the $LP_{01}$ mode, further enhancing modal stability for the signal.

In one embodiment, the HOM fiber module includes an HOM fiber. Suitable HOM fibers can include, without limitation, a solid silica-based fiber. In another embodiment, the HOM fiber module includes an HOM fiber and at least one mode converter. The at least one mode converter can be connectedly disposed between the optical pulse source and the HOM fiber. The HOM fiber module can also include an HOM fiber, a mode converter connectedly disposed between the optical pulse source and the HOM fiber, and also a second mode converter terminally connected to the HOM fiber. Suitable mode converters that can be used in the present invention are well known in the art, and can include, for example, a long period grating (LPG). Successive HOM modules, each with different characteristics, can be concatenated together, forming a cascaded arrangement configured to generate SSFS and/or Cherenkov radiation at multiple wavelengths.

Suitable optical pulse sources that can be used in the present invention can include, without limitation, mode-locked lasers and chirped pulse amplification (CPA) systems. More particularly, the mode-locked laser can be a mode-locked fiber laser, and the CPA system can be a fiber CPA system. The optical pulse source in the present invention can include those that generate input optical pulses having various pulse energies. In one embodiment, the optical pulse source generates a pulse energy of at least 1.0 nanojoules (nJ). In another embodiment, the optical pulse source generates input optical pulses having a pulse energy of between about 1.0 nJ and about 100 nJ.

The optical pulse source can also be one that generates input optical pulses such that the first wavelength is a wavelength within the transparent region of a silica-based fiber. In one embodiment, the optical pulse source is one that generates a first wavelength below 1300 nanometers (nm). In another embodiment, the optical pulse source is one that generates a first wavelength between the range of about 300 nm and about 1300 nm.

The optical pulse source used in the present invention can also be one that generates input optical pulses having a sub-picosecond pulse width.

Suitable HOM fiber modules that can be used in the present invention can include, without limitation, HOM fiber modules that produce output optical pulses having a pulse energy of at least 1.0 nJ. Suitable HOM fiber modules can also be those that produce output optical pulses such that the desired wavelength that is below 1300 nm. In another embodiment, the HOM fiber module produces an output optical pulse having a desired wavelength between the range of about 300 nm and about 1300 nm. The HOM fiber module can also be such that it produces output optical pulses having a subpicosecond pulse width.

The apparatus of the present invention can further include a power control system connectedly disposed between the optical pulse source and the HOM fiber module. The power control system for use in the present invention can be one that achieves subnanosecond power tuning of the first wavelength. Suitable power control systems can include, without limitation, a lithium niobate (LiNbO$_3$) intensity modulator device.

The apparatus of the present invention can further include a single-mode fiber (SMF) connectedly disposed between the optical pulse source and the HOM fiber module.

The apparatus of the present invention can be used in a variety of applications where optical pulses of a desired wavelength are needed. For example, the apparatus can be effective in producing output optical pulses that can penetrate animal or plant tissue at a penetration depth of at least 0.1 millimeters (mm).

The apparatus of the present invention can further be such that the HOM fiber module is terminally associated with medical diagnostic tools such as an endoscope or an optical biopsy needle.

The apparatus of the present invention can further be functionally associated with a multiphoton microscope system.

The apparatus of the present invention can also further be functionally associated with a multiphoton imaging system.

The present invention also relates to a method of producing optical pulses having a desired wavelength. This method includes generating input optical pulses using an optical pulse source, where the input optical pulses have a first wavelength and a first spatial mode. The input optical pulses are delivered into an HOM fiber module to alter the wavelength of the input optical pulses from the first wavelength to a desired wavelength by soliton self-frequency shift (SSFS) within the HOM fiber module, thereby producing output optical pulses having the desired wavelength.

The method of the present invention can involve the use of the apparatus described herein as well as the various aspects and components of the apparatus (e.g., the optical pulse source and the HOM fiber module) described herein.

In one embodiment, the method can further include converting the first spatial mode of the input optical pulses into a second spatial mode prior to delivering the input optical pulses into the HOM fiber so that the output optical pulses have the second spatial mode, where the first spatial mode and the second spatial mode are different modes. This method can further include reconverting the second spatial mode of the output optical pulses back to the first spatial mode.

In another embodiment, the method can further include tuning the first wavelength of the input optical pulses to an intermediate wavelength prior to delivering the input optical pulses into the HOM fiber. The tuning can include, without limitation, power tuning. Such power tuning can include varying the power of the input optical pulses so as to vary the desired wavelength. In one embodiment, the power tuning can include subnanosecond power tuning using a power control system connectedly disposed between the optical pulse source and the HOM fiber module. Suitable power control systems can include, without limitation, a lithium niobate intensity modulator device. In another embodiment, the tuning can be achieved by varying the length of the HOM fiber so as to vary the desired wavelength.

Described in more detail below is the concept of SSFS and Cherenkov radiation in optical fibers and more particularly in HOM fibers.

Other and further aspects and embodiments of the present invention will become apparent during the course of the following discussion and by reference to the accompanying drawings.

BRIEF DESCRIPTION OF THE DRAWINGS

Referring now to the drawings,

FIG. 12(a): Near-field images. FIG. 12(b): Mode profiles at various wavelengths. Conventional mode transitions from high to low index;

designed HOM shows opposite evolution. Grey background denotes index profile of the fiber. FIG. 12(c): Resultant total dispersion ($D_{total}$, solid), also shown are silica material dispersion ($D_m$, dashed) and zero-dispersion line (dotted), where arrows show contribution of waveguide dispersion ($D_w$) to total dispersion;

DETAILED DESCRIPTION

Figure 1A:
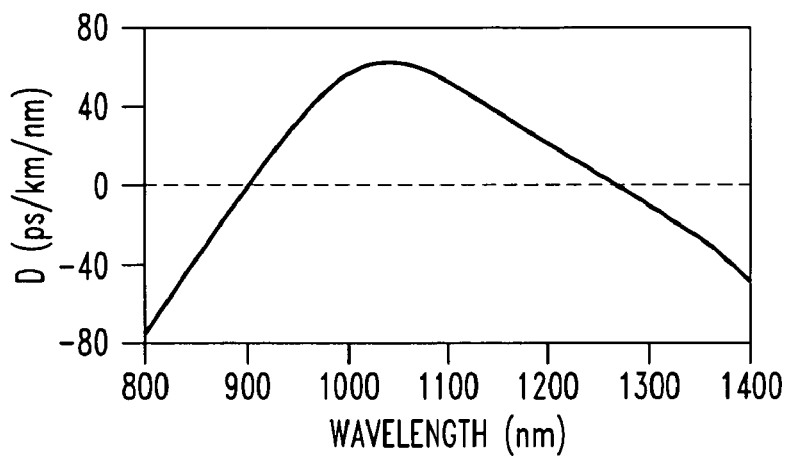
FIG. 1(a): Total dispersion for propagation in the LP$_{02}$ mode.

Soliton self-frequency shifting (SSFS) is a well-known and well-understood phenomenon. The concept of SSFS was first discovered ~20 years ago in fiber optic communications, and most of the past experiments on SSFS relates to telecom. Optical soliton pulses generally experience a continuous downshift of their carrier frequencies when propagating in a fiber with anomalous dispersion. This so-called soliton self-frequency shift originates from the intra-pulse stimulated Raman scattering which transfers the short wavelength part of the pulse spectrum toward the long wavelength part (SSFS sometimes is also called Raman soliton shift). Through the balancing of optical nonlinearity and fiber dispersion (i.e., soliton condition), the pulse maintains its temporal and spectral profiles as it shifts to the longer wavelengths. Although the physics of SSFS was well known for the last 20 years, its practical application was limited because the use of conventional fibers for generating wavelength-shifting solitons has major limitations. However, several new classes of optical fibers, such as photonic crystal fibers (PCF, sometimes also known as microstructure fiber) and solid-core or air-core band gap fibers (BGF), has generated enormous excitement in the last 5 years and greatly improved the feasibility of SSFS. Indeed, there are a number of experimental demonstrations of SSFS in PCF and BGF. However, none of the previous work can generate soliton energies that are of practical interest to biomedical research, i.e., solitons with pulse energies between 1 to 10 nJ and at wavelengths below 1300 nm. As we will elaborate below, the pulse energies produced in previous works are either one or two orders of magnitude too small or several orders of magnitude too large.

Because material nonlinearity for silica glass is positive at the relevant spectral range, the fundamental condition to form an optical soliton in silica fiber is anomalous dispersion. In addition, the existence of an optical soliton requires exact balance between fiber nonlinearity and dispersion. Thus, the energy of an optical soliton ($E_s$) is determined by material nonlinearity and dispersion, and scales as $$E_s \propto \lambda^3 \cdot D \cdot A_{eff}/n_2\tau \quad (1),$$

where $n^2$ is the nonlinear refractive index of the material, $\tau$ is the pulse width, D is the dispersion parameter, $A_{eff}$ is the effective mode field area, and $\lambda$ is the wavelength. Although standard single mode fibers (SMF) cannot achieve anomalous dispersion at $\lambda<1280$ nm, it was realized that the total dispersion (D) in a waveguide structure such as an optical fiber consists of contributions from the material ($D_m$), the waveguide ($D_w$), and the bandgap (in the case of BGF). By appropriately engineering the contributions of the waveguide and/or the bandgap, it is possible to achieve anomalous dispersion (D>0) at virtually any wavelength, thus, enabling soliton and SSFS at wavelengths below 1280 nm. (It is worth noting that the dispersion parameter D is actually positive for anomalous dispersion.) Previously, there were two approaches to achieve anomalous dispersion, and therefore solution propagation and SSFS, at $\lambda<1280$ nm:

(1) Small-core PCF can achieve anomalous dispersion for wavelengths down to ~550 nm. When the waveguide is tightly confining, with the air-silica boundary defining the confinement layer, the waveguide dispersion ($D_w$) is akin to that of microwave waveguides with perfectly reflecting walls. Hence, large positive waveguide dispersion may be realized by tightly-confined $LP_{01}$ (fundamental) modes in PCFs. However, the associated trade-off is with $A_{eff}$, and designs that yield dispersion $>+50$ ps/mm/km in the wavelength ranges of 800 nm or 1030 nm typically have $A_{eff}$ of 2-5 $\mu m^2$. Because the solution energy scales with the value of D*$A_{eff}$, a small $A_{eff}$ will severely limit the pulse energies that can be obtained with PCFs. For example, in one experiment using a special PCF structure, a soliton pulse energy of ~20 pJ was obtained at 800 nm, orders of magnitude smaller than practical for imaging. Indeed, most PCF structures are designed to demonstrate nonlinear optical effects at the lowest possible pulse energy.

(2) Air-guided BGFs potentially can offer anomalous dispersion at any guiding wavelength, but the extremely low nonlinearities in these fibers (the nonlinearity of air is ~one thousand times smaller than silica glass) make them impractical for a device that utilizes a nonlinear interaction to achieve the frequency shift. In one demonstration, a MW (~$\mu$J pulse) optical amplifier was needed for observing SSFS in air-guiding fiber. Not only is such a high power unnecessary for most biomedical applications, the cost and complexity of the high power amplifier also makes it completely impractical as a tool for biomedical research.

Although SSFS provides a convenient mechanism for wavelength tuning of a fixed wavelength fiber laser, previous works in SSFS were performed at soliton energies either too low or too high (by at least an order of magnitude) for practical use. Thus, it is essential to invent a new fiber structure, with just the right amount of optical nonlinearity and dispersion (i.e., $D \cdot A_{eff}/n_2$) in order to produce soliton pulses of practical utility for biomedical imaging.

An optical fiber generally propagates a number of spatial modes (electric field states). Because of modal dispersion and interference, however, only single mode fibers (i.e., fibers with only one propagating mode) are of interest for applications such as high speed data transmission and pulse delivery for imaging. It was realized, however, that a multimode fiber can propagate only one mode if two conditions are met: (1) the input field is a pure single mode and (2) the couplings between various modes during propagation are small. In the case that the one propagating mode is not the fundamental mode, the fiber is called a HOM fiber. HOM fibers first attracted attention in optical communications nearly ten years ago. The main motivation was for dispersion compensation of high bit-rate optical communications. The advantage of HOM fibers is to provide another degree of freedom in the design space to achieve the desired dispersion characteristics. There were a number of devices invented using HOM fibers. In fact, dispersion compensators based on HOM fibers have been commercially available for several years.

It has been realized that the design freedoms enabled by HOM fibers are exactly what is needed for achieving the desired soliton energy at wavelengths below 1300 nm for biomedical imaging: (1) A higher order mode can achieve anomalous dispersion at wavelength below 1300 nm, a condition necessary for soliton and impossible to obtain in a conventional silica SMF. (2) A higher order mode typically has a much larger $A_{eff}$ than that of PCF for achieving higher soliton energy. (3) The silica core of the HOM fiber retains just enough nonlinearity to make SSFS feasible at practical energy level. (4) The all silica HOM fiber retains the low loss properties (for both transmission and bending) of a conventional SMF, and allows easy termination and splicing. (5) A HOM fiber leverages the standard silica fiber manufacturing platform, which has been perfected over the course of 30 years with enormous resources. Thus, an appropriately designed HOM fiber can provide the necessary characteristics desired for biomedical imaging, and can be manufactured immediately with high reliability.

EXAMPLES

The Examples set forth below are for illustrative purposes only and are not intended to limit, in any way, the scope of the present invention.

Example 1

Demonstration of Soliton Self-Frequency Shift Below 1300 nm in Higher-Order-Mode, Solid Silica-Based Fiber Soliton-self frequency shift of more than 12% of the optical frequency was demonstrated in a higher-order-mode (HOM) solid, silica-based fiber below 1300 nm. This new class of fiber shows great promise of supporting Raman-shifted solitons below 1300 nm in intermediate energy regimes of 1 to 10 nJ that cannot be reached by index-guided photonic crystal fibers or air-core photonic band-gap fibers. By changing the input pulse energy of 200 fs pulses from 1.36 nJ to 1.63 nJ, clean Raman-shifted solitons were observed between 1064 nm and 1200 nm with up to 57% power conversion efficiency and compressed output pulse widths less than 50 fs. Furthermore, due to the dispersion characteristics of the HOM fiber, red-shifted Cherenkov radiation in the normal dispersion regime for appropriately energetic input pulses was observed at energies of 1.45 nJ and above.

The HOM fiber used in the experiments of this example was shown to exhibit large positive dispersion (~60 ps/nm-km) below 1300 nm while still maintaining a relatively large effective area of 44 μm$^2$, ten times that of index-guided PCFs for similar dispersion characteristics. Through soliton shaping and higher-order soliton compression within the HOM fiber, clean 49 fs output pulses from 200 fs input pulses were generated.

Figure 1B:
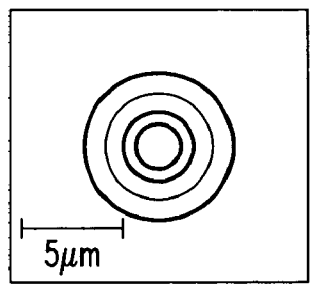
FIG. 1(b): Experimental near-field image of the LP$_{02}$ mode with $A_{eff}$=44 μm$^2$.

FIG. 1(a) shows the dispersion curve for the $LP_{02}$ mode in the HOM fiber used in the experiment of the present example. To generate positive dispersion below 1300 nm while simultaneously maintaining a large effective area, light propagates solely in the $LP_{02}$ mode. Light is coupled into the $LP_{02}$ mode using a low-loss long period grating (LPG). The index profile of the HOM fiber is made such that the mode becomes more confined to the higher-index core with an increase in wavelength, resulting in net positive dispersion. FIG. 1(a) shows a dispersion of 62.8 ps/nm-km at 1060 nm which is comparable to that of microstructured fibers used previously for SSFS and exhibits two zero dispersion wavelengths at 908 nm and 1247 nm. The mode profile at the end face of the HOM fiber is shown in FIG. 1(b), demonstrating a clean higher-order $LP_{02}$ mode and an effective area of 44 μm$^2$.

Figure 1C:
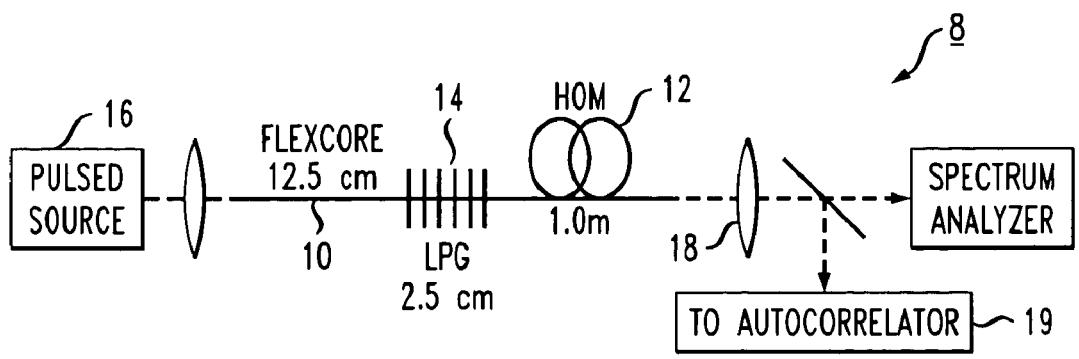
FIG. 1(c): Experimental setup used to couple light through the HOM fiber module and generate soliton self-frequency shifting.

A schematic of the fiber-module 8 used for this experiment is shown in FIG. 1(c). Here light propagates in the fundamental mode through 12.5 cm of standard single mode (Flexcore) fiber 10 before being coupled into 1.0 m of the HOM fiber 12 with a 2.5 cm long period grating (LPG) 14, entirely contained within a fiber fusion-splicing sleeve. Light resides in the $LP_{01}$ mode for approximately half the length of the grating 14 after which more than 99% is coupled into the $LP_{02}$ mode. The entire module 8 has a total loss of 0.14 dB which includes all splices, fiber loss, and mode conversion. It is also noted that the all-silica HOM fiber 12 leverages the standard silica fiber manufacturing platform and retains the low loss properties (for both transmission and bending) of a conventional SMF, allowing easy termination and splicing. The combination of the single mode fiber 10 and LPG 14 creates an input signal at the HOM 12 which exhibits a linear chirp of at least 5.25 fs/nm.

The pump source 16 consisted of a fiber laser (Fianium FP1060-IS) which delivered a free space output of ~200 fs pulses at a center wavelength of 1064 nm and an 80 MHz repetition rate. A maximum power of 130 mW was able to be coupled into the fiber module 8, corresponding to 1.63 nJ input pulses. The input pulse energy was varied from 1.36 nJ to 1.63 nJ to obtain clean spectrally-shifted solitons with a maximum wavelength shift of 136 nm (12% of the carrier wavelength), FIG. 2(a). Theoretical traces from numerical simulation for similar input pulse energy are plotted adjacent to the experimental data in FIG. 2(d). The split-step Fourier method was used in the simulation and included self-phase modulation (SPM), stimulated Raman scattering (SRS), self-steepening, and dispersion up to fifth-order. The dispersion coefficients were obtained by numerically fitting the experimental curve in FIG. 1(a) and a nonlinear parameter γ=2.2 W$^{-1}$ Km$^{-1}$ and a Raman response of $T_R$=5 fs were used in the simulation. The irregularly shaped spectrum of the input source was also approximated (FIG. 2(b)) with an 8.5 nm, Gaussian shape corresponding to 200 fs Gaussian pulses. Though a more accurate description should include the full integral form of the nonlinear Schrödinger equation, the excellent qualitative match and reasonable quantitative match validates this approach.

Figure 2:
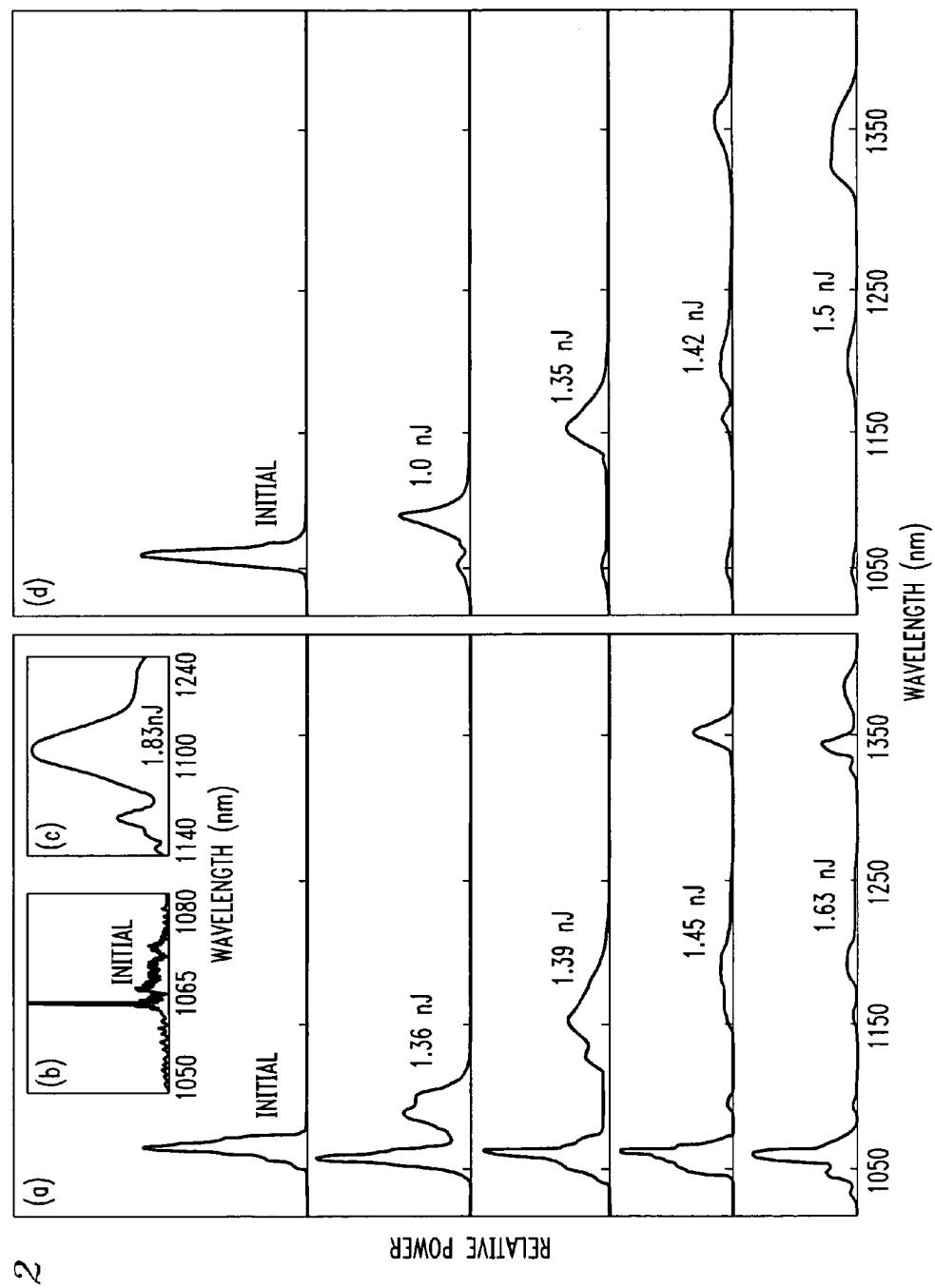
FIG. 2(a): Soliton self-frequency shifted spectra corresponding to different input pulse energies into the HOM fiber, with all traces taken at 4.0 nm resolution bandwidth (RBW) and input pulse energy noted on each trace. Power conversion efficiency is 57% for 1.39 nJ input.
FIG. 2(b): High resolution trace of the initial spectrum; 0.1 nm RBW.
FIG. 2(c): High resolution trace of the shifted soliton for 1.63 nJ input into the HOM; 0.1 nm RBW.
FIG. 2(d): Soliton self-frequency shifted spectra calculated from simulation.
Figure 3:
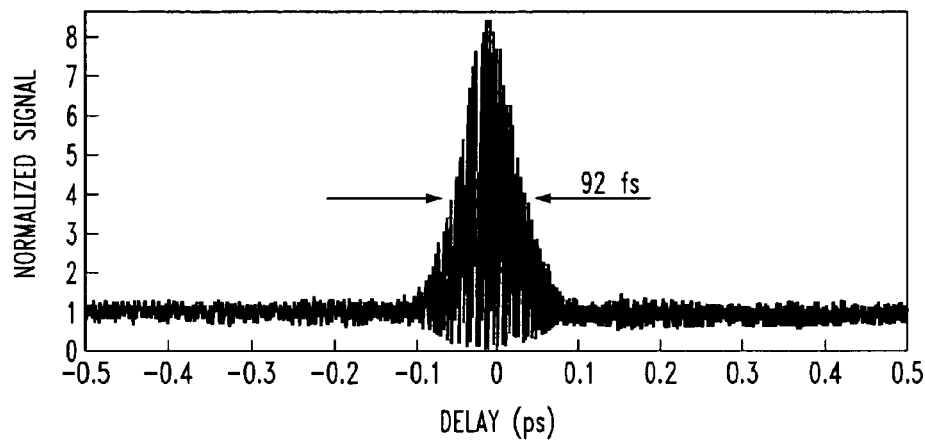
FIG. 3: Second-order interferometric autocorrelation trace of HOM output for 1.39 nJ input pulses. Autocorrelation FWHM measured to be 92 fs corresponding to a deconvolved pulse width of 49 fs.

57% power conversion from the input pulse spectrum to the red-shifted soliton was measured for the case of 1.39 nJ input pulses to achieve ~0.8 nJ output soliton pulses, FIG. 2(a). The corresponding second-order interferometric autocorrelation (FIG. 3) gives an output pulse width of 49 fs, assuming a sech$^2$ pulse shape, showing a factor of four in pulse width reduction due to higher-order soliton compression (soliton order N=2.1) in the HOM fiber 12. The measured spectral bandwidth of 35 nm gives a time-bandwidth product of 0.386 which is 23% beyond that expected for a sech$^2$ pulse shape. It is believed that the discrepancy is likely due to dispersion from ~5 cm of glass (collimating and focusing lenses 18) between the fiber output and the two-photon detector inside the autocorrelator 19. This explanation is supported by numerical simulation which gives an output pulse width of 40 fs. Of further note is the ripple-free, high resolution spectrum of the shifted soliton for 1.63 nJ input, FIG. 2(c). This is indicative of propagation exclusively in the $LP_{02}$ mode since multimode propagation would surface as spectral interference.

Finally, the appearance of Cherenkov radiation centered about 1350 nm for 1.45 nJ and 1.63 nJ input pulse energies, FIG. 2(a). Here, as has been demonstrated previously, Cherenkov radiation is generated from phase matching between the soliton and resonant dispersive waves. This process occurs most efficiently when the soliton approaches the zero dispersion wavelength where the dispersion slope is negative. Pumping more energy into the fiber does not red-shift the soliton any further, but instead transfers the energy into the Cherenkov spectrum. As the input pulse energy is increased from 1.45 nJ to 1.63 nJ (FIG. 2(a)), the soliton is still locked at a center wavelength of ~1200 nm but more energy appears in the Cherenkov spectrum. Simulations suggest that an ultrashort pulse can be filtered and compressed from this radiation to achieve energetic pulses across the zero-dispersion wavelength.

Both the wavelength shift and pulse energy can be significantly increased beyond what has been demonstrated through engineering of the fiber module. For example, simple dimensional scaling of the index profile can be used to shift the dispersion curve of the $LP_{02}$ mode. Numerical modeling shows that an output soliton energy of approximately 2 nJ can be realized if the dispersion curve is shifted ~100 nm to the longer wavelength side. Additionally, pulse energy can be scaled by increasing $D \cdot A_{eff}$. Aside from increasing the magnitude of dispersion through manipulation of the index profile and dimensions of the fiber, the effective area can be significantly enhanced by coupling into even higher-order modes. An effective area of ~2000 μm$^2$ (more than 40 times this HOM fiber) was recently achieved by coupling to the $LP_{07}$ mode, which is hereby incorporated by reference in its entirety).

In summary, SSFS between 1064 nm and 1200 nm has been demonstrated in a higher-order-mode, solid silica-based fiber. 49 fs Raman-shifted solitons were obtainable at 0.8 nJ with up to 57% power conversion efficiency. Due to the dispersion characteristics of the HOM fiber, Cherenkov radiation was also observed for appropriately energetic input pulses. It is believed that HOM fiber should provide an ideal platform for achieving soliton energies from 1 to 10 nJ for SSFS at wavelengths below 1300 nm, filling the pulse energy gap between index-guided PCFs and air-core PBGFs. This intermediate pulse energy regime which could not be reached previously for SSFS could prove instrumental in the realization of tunable, compact, all-fiber femtosecond sources for a wide range of practical applications.

In this work of the present invention, Cherenkov radiation has been generated at 1350 nm in an HOM fiber with 20% power conversion efficiency (approximately 25% photon efficiency). The Cherenkov output pulses have been successfully filtered and compressed to 106 fs. Cherenkov radiation generated in the normal dispersion regime of this HOM fiber can be used to extend frequency shifting even further, or to create a three-color femtosecond source (centered at the pump, frequency shifted soliton, and Cherenkov radiation wavelengths). This new class of fiber shows great promise for generating femtosecond pulses at various wavelengths in the energy regime of several nJs.

Figure 4A:
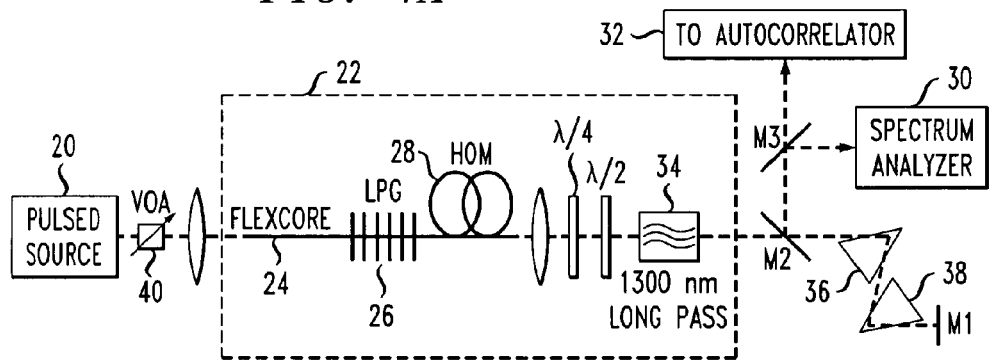
FIG. 4(a): Experimental setup used to couple light through the HOM fiber module and measure the Cherenkov pulse generated in the HOM fiber.
Figure 4B:
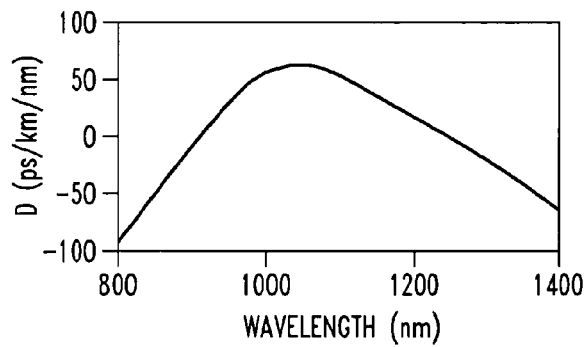
FIG. 4(b): Total dispersion for propagation in the LP$_{02}$ mode.
Figure 4C:
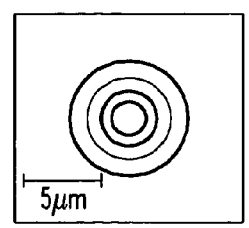
FIG. 4(c): Experimental near-field image of the LP$_{02}$ mode with $A_{eff}$=44 μm$^2$.

The experimental setup is shown in FIG. 4(a). The pump source 20 consists of a pulsed fiber laser (Fianium FP 1060-1S) centered at 1064 nm, with 80 MHz repetition rate and 200 fs pulsewidth. We couple the source into the HOM fiber module 22, which consists of a 12.5 cm standard single mode fiber (flexcore) pigtail 24, 2.5 cm of long period grating (LPG) 26 and 1 m of HOM fiber 28. The combination of 12.5 cm of SMF 24 and an LPG 26 of length 2.5 cm will provide an input signal to the HOM fiber 28 that exhibits a linear chirp of at least 5.25 fs/nm. The LPG 26 converts the fundamental mode to the higher-order $LP_{02}$ mode with good (>90%) efficiency over a large (50 nm) bandwidth; for the input wavelength of 1064 nm, 99% of the fundamental mode is converted to the $LP_{02}$ mode, which exhibits anomalous dispersion in the HOM fiber 28 between 908 and 1247 nm, see FIG. 4(b). At the input wavelength, the $LP_{02}$ mode, shown in FIG. 4(c), has an effective area $A_{eff}=44$ μm$^2$. The output of the HOM fiber module 22 is collimated and measured with an optical spectrum analyzer 30 and a second order interferometric autocorrelator 32. A 1300 nm long-pass filter 34 is used to select out the Cherenkov radiation, and a pair of silicon prisms 36, 38 are used for dispersion compensation and to simultaneously filter out any residual pump wavelength. A polarizer and a half-wave plate serve as a variable optical attenuator (VOA) 40 at the input of the HOM fiber module 22.

Figure 5A:
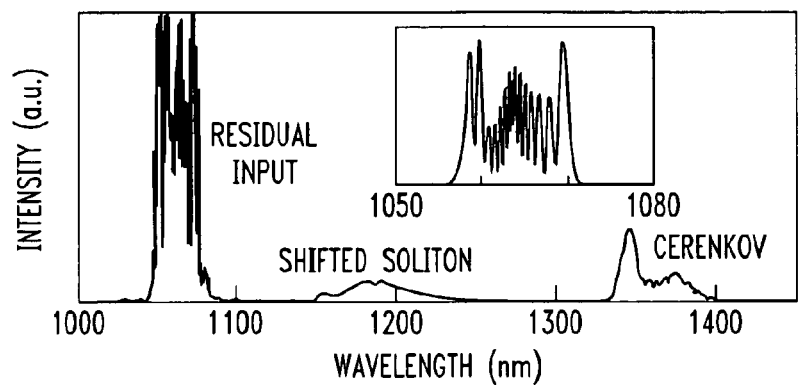
FIG. 5(a). Optical spectrum at output of HOM fiber module of FIG. 4 from experiment.
Figure 5B:
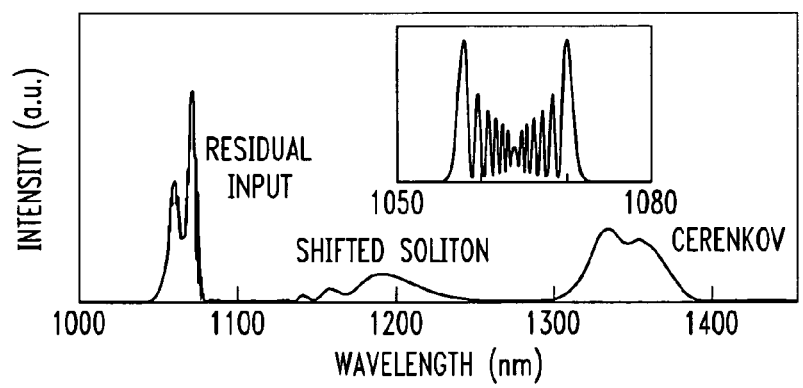
FIG. 5(b). Optical spectrum at output of HOM fiber module of FIG. 4 from simulation, where insets show input spectra on a 30 nm window.

We are able to couple a total power of 265 mW (3.31 nJ pulse energy) into the HOM fiber module 22. At this power level, the residual input, shifted soliton, and Cherenkov radiation can be clearly seen in the output spectrum shown in FIG. 5(a). The optical power residing in the Cherenkov band is ~53 mW (0.66 nJ pulse energy), a power conversion efficiency of 20% (25% photon conversion efficiency). We qualitatively match the experimental spectrum in simulation, shown in FIG. 5(b). We note the excellent qualitative match between simulation and experiment and the relatively good quantitative match. The observed quantitative discrepancy could arise from our approximation of both the input source characteristics and the dispersion curve, which is not characterized beyond 1400 nm. This simulated spectrum corresponds to an input power of 189 mW (2.36 nJ pulse energy), with 30% conversion to the Cherenkov band, equivalently 0.70 nJ in the Cherenkov pulse. At this power level, the soliton (centered at approximately 1200 nm) has shifted enough energy past the zero-dispersion wavelength so that resonant coupling occurs efficiently at 1350 nm (Cherenkov radiation). Intuitively, growth of the Cherenkov radiation begins exponentially with increasing input power until the "spectral recoil" exerted by the Cherenkov radiation on the soliton cancels the Raman self-frequency shift. After the soliton is frequency-locked, for our experiment at 1200 nm, increasing the pump power will only transfer energy to the Cherenkov spectrum instead of shifting the soliton further. Simulation shows that up to approximately 5 nJ can be pumped into the Cherenkov band, after which nonlinear effects begin to degrade the system. Experimental pulse energies were limited by the pump source's non-Gaussian beam shape, which results in poor coupling into the HOM fiber module.

Figure 6:
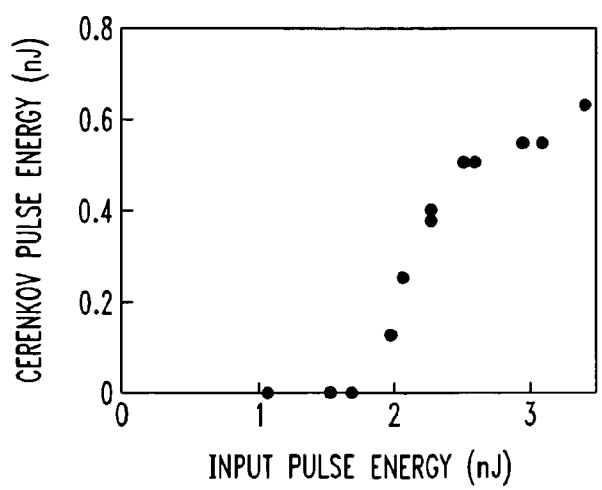
FIG. 6. Cherenkov output pulse energy as a function of input pulse energy.

We additionally measure Cherenkov output pulse energy as a function of input pulse energy by varying the attenuation (via VOA 40) at the input of the HOM fiber module 22. We can see from FIG. 6 that the Cherenkov pulse energy increases rapidly at input energies of approximately 2 nJ (input power 160 mW). This "threshold" behavior, as well as the location of the knee agrees well with our simulation. The threshold behavior has also been experimentally observed previously in PCF. A discrepancy in Cherenkov pulse energy between numerical results and experiment was found at the highest input pulse energies we investigated, where simulation shows a faster increase in Cherenkov energy than the experimental results. We currently do not have an explanation for this discrepancy.

Figure 7A:
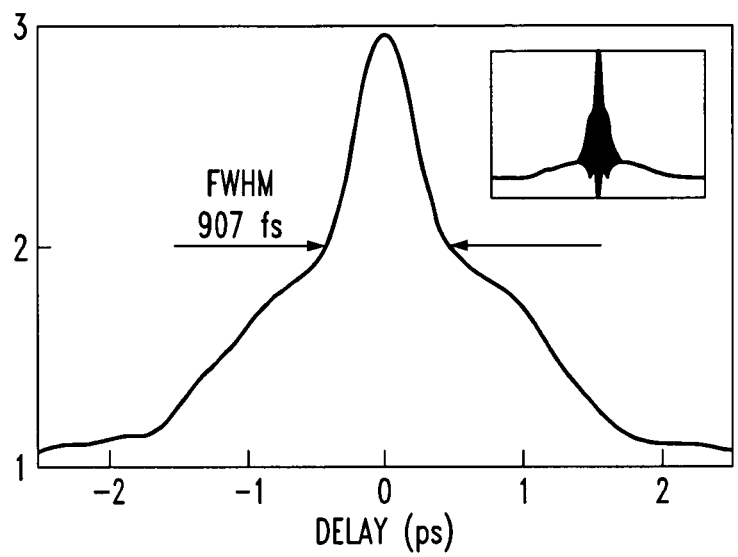
FIG. 7. Intensity autocorrelation traces of Cherenkov pulse, (a) at the output of the HOM fiber module, without dispersion compensation, and (b) dispersion compensated pulse, with interferometric autocorrelation traces shown as insets, this corresponds to pulsewidths of 465 fs and 106 fs in (a) and (b), respectively.
Figure 7B:
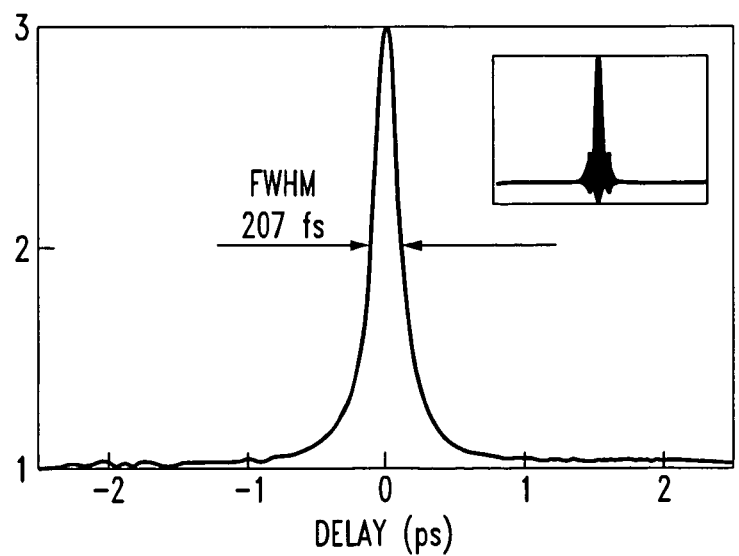

A second order autocorrelation trace of the filtered Cherenkov pulse at the output of the HOM fiber module 22 is shown in FIG. 7(a); it is visibly chirped and has an autocorrelation FWHM of 907 fs. We are able to compress this pulse to 207 fs autocorrelation FWHM, shown in FIG. 7(b), with appropriate dispersion compensation by a silicon prism pair 36, 38. We calculate the dispersion provided by the silicon prism pair (prism separation distance approximately 7 cm in optical pathlength) to be $\beta_2=-0.0065$ ps$^2$ and $\beta_3=-1.9\times10^{-5}$ ps$^3$. Applying such dispersion compensation values to our spectrally matched simulation, we obtain numerically an autocorrelation FWHM of 200 fs and a pulsewidth of 103 fs. If we assume the same pulse shape, the experimentally measured deconvolved pulsewidths with and without dispersion compensation are 106 fs and 465 fs, respectively.

The location of the Cherenkov radiation can be tuned through engineering of the fiber dispersion. For example, simple dimensional scaling of the index profile of the HOM fiber 28 can be used to shift the dispersion curve of the $LP_{02}$ mode. By shifting the zero-dispersion wavelength 50 nm to the shorter wavelength side, the generated Cherenkov radiation will also shift by approximately the same amount. Such design control could lead to the generation of useful femtosecond pulsed sources in spectral regimes unattainable by current laser systems. Furthermore, the large effective area and flexibility for dispersion engineering in the HOM fiber open up the possibility to achieve pulse energies significantly beyond the level demonstrated here.

Although not demonstrated in our experiment, the generated Cherenkov pulse can be converted back to the fundamental mode by another LPG at the output of the HOM fiber module. With proper dispersion matching, efficient and broadband (>100 nm) LPG has already been experimentally demonstrated for mode conversion. Such an LPG will ensure the output pulse is always converted back to a Gaussian profile, within the tuning range. An important consideration for the output LPG is its length. Since the energetic output pulses are solitons for a specific combination of dispersion and $A_{eff}$ of the $LP_{02}$ mode, nonlinear distortions may occur when the energetic pulse goes to the (smaller $A_{eff}$) fundamental $LP_{01}$ mode at the output. However, the length over which the signal travels in the $LP_{01}$ mode, and hence the distortion it accumulates, can be minimized because the high-index core of the HOM fibers enable LPG lengths of <5 mm. This implies that light can reside in the $LP_{01}$ mode for <2.5 mm, hence largely avoiding nonlinear distortions. Note that the requirement for short LPGs actually complements the need for broad-bandwidth operation, since the conversion bandwidth is typically inversely proportional to the grating length. On the other hand, depending on the intended usage, the higher-order-mode output could also be used directly without mode conversion.

In summary, we demonstrate a method of generating short pulses at 1350 nm by exciting Cherenkov radiation in a HOM fiber with a 1064 nm pulsed fiber source. We have successfully dechirped a 465 fs pulse at the output of the HOM fiber to a 106 fs pulse with a pair of silicon prisms. This method of generating short pulses at 1350 nm can potentially be extended to other wavelengths and to higher pulse energies with appropriate design of the HOM fiber.

Example 2

Figure 8:
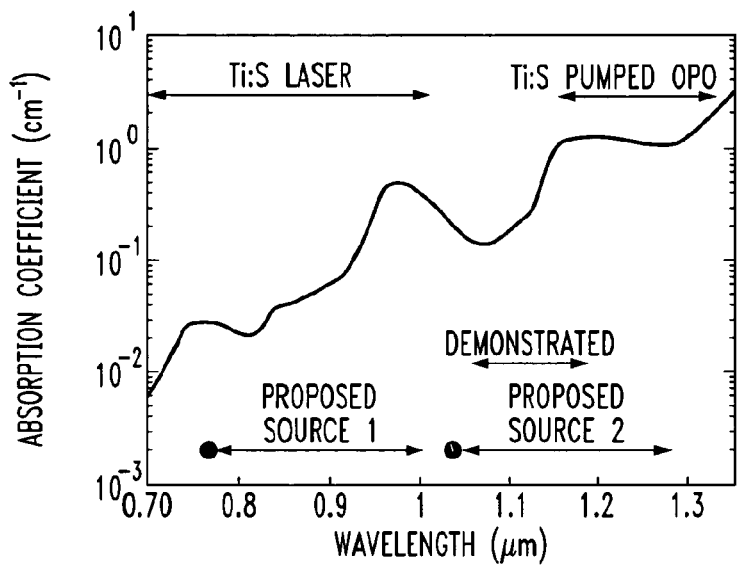
FIG. 8 shows an absorption coefficient of water as a function of wavelength.

All Fiber, Wavelength Tunable Femtosecond Sources for Biomedical Spectroscopy and Imaging To emphasize the significance of the proposed femtosecond sources, we compare our proposed sources with the existing mode-locked Ti:S laser, Ti:S pumped OPO and femtosecond fiber sources. FIG. 8 shows the wavelength tuning range of the sources. The absorption spectrum of water is also shown to indicate the relevant wavelength range for biomedical imaging. The arrows indicate the tuning ranges of a femtosecond Ti:S laser, a Ti:S laser pumped OPO, and the proposed sources. The solid circles represent the wavelength of existing femtosecond fiber lasers. The tuning range that has already been demonstrated in a preliminary study is also indicated. In essence, we want to develop two all-fiber femtosecond sources that cover approximately the same wavelength window as the existing Ti:S laser and Ti:S pumped OPO. These wide wavelength tuning ranges were simply impossible to achieve in any existing fiber sources, but are crucial to satisfy the requirements of nonlinear biomedical engineering.

TABLE 1

Comparisons of femtosecond laser systems

| fs lasers | pulse energy (nJ)* | | pulse width (fs) | wavelength | | size (cubic feet) | estimated cost** $k |
| | free space | fiber delivered | | tuning range (nm) | tuning speed (s) | | |
| --- | --- | --- | --- | --- | --- | --- | --- |
| Ti:S | 25 | 5 | ~60 | 700-1000 | >10 | ~10 | 170 |
| Ti:S pumped OPO | 4 | 1 | ~100 | 1120-1340 | >10 | ~14 | 250 |
| Cr:Forsterite | 3 | 1 | ~60 | 1230-1280 | >10 | ~4 | 68 |
| Current 1030 fiber source | 15 | 5 | ~200 | 1030-1070 | >10 | ~1 | 40 |
| Current 1550 fiber source | 15 | 5 | ~200 | 1540-1590 | >10 | ~1 | 55 |
| proposed source at 775 to 1000 | 10 | 10 | ~50 | 775-1000 | ultrafast | ~1.5 | 70 |
| proposed source at 1030 to 1280 | 10 | 10 | ~50 | 1030-1280 | ultrafast | ~1.5 | 50 |

*The pulse energies listed are all at the peak of the wavelength tuning range.
**The estimated cost for the existing laser systems are based on written price quotes from commercial vendors. The estimated cost for the proposed sources are largely based on the price of existing sources at 1550 and 1030 nm, with our best effort estimates for the additional cost of the HOM module and the control electronics. We have also included necessary cost for frequency doubling for the source at 775 nm.

Table 1 compares some of the key characteristics of the existing and our proposed femtosecond sources. The proposed systems would be much less expensive than the currently used state-of-the-art single box Ti:S lasers (Spectra-Physics Mai Tai and the Coherent Chameleon), probably ⅓ to ¼ the cost. The telecom manufacturing platform employed in the proposed fiber sources provides an inherent opportunity for further cost reduction by volume scaling. In addition, there are the practical advantages offered by the all-fiber configuration, such as a compact foot print and a robust operation. However, what truly sets the proposed femtosecond sources apart from other existing fiber sources is performance. Table 1 shows that the proposed all-fiber sources will achieve comparable or better performances in terms of output pulse energy, pulse width, and wavelength tuning range when compared to bulk solid-state mode-locked lasers. We note that the output characteristics of the proposed sources listed above are delivered through an optical fiber. The eliminate of the free-space optics makes the proposed fiber sources more efficient in delivering power to an imaging setup. Thus, even at a slightly lower output power, the imaging capability of the proposed sources will likely be close to that of the free-space Ti:S laser. It is worth emphasizing that significant research and development efforts have been devoted to femtosecond fiber sources in the last 15 years or so. However, femtosecond fiber lasers have so far failed to have a major impact in biomedical research. We believe the reason for the low penetration of fiber femtosecond sources in the biomedical field is precisely due to various performance handicaps (such as pulse energy, wavelength tunability, pulse width, fiber delivery, etc.) that kept existing fiber sources from being the "complete package." It has nothing to do with the lack of demand or interest from biomedical researchers. Leveraging major developments, we believe we have finally arrived at the stage where all-fiber femtosecond sources can be realized without sacrificing performance. The successful completion of this research program will make femtosecond sources truly widely accessible to biologists and medical researchers and practitioner.

Figure 9:
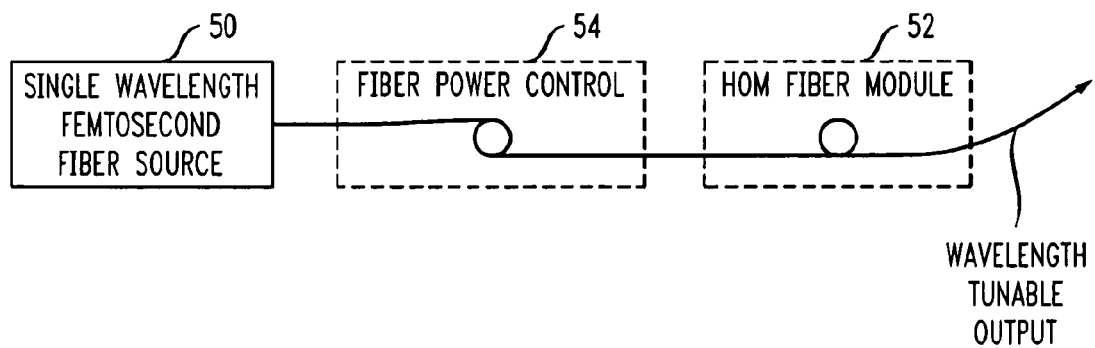
FIG. 9 is a schematic drawing of one embodiment of an all fiber, wavelength tunable, energetic, femtosecond source.

This program explores a new route for generating energetic femtosecond pulses that are continuously tunable across a wide wavelength range, where, in contrast to previous approaches, ultrafast pulses are wavelength shifted in a novel HOM fiber module by SSFS. By eliminating the constraint of a broad gain medium to cover the entire tuning range, our approach allows rapid, electronically controlled wavelength tuning of energetic pulses in an all-fiber configuration. FIG. 9 schematically shows the design of the proposed excitation sources. We start off with a single wavelength femtosecond fiber source 50 at 1030 nm (or 775 nm with frequency doubling from 1550 nm) with high pulse energy (10 to 25 nJ). The pulse is then propagated into a specifically designed HOM fiber module 52 for wavelength shifting via SSFS. The output wavelength of the soliton pulses are controlled by the input pulse energies (and/or HOM fiber length) using a pulse controller 54. The target performances of the proposed systems are 5- to 10-nJ pulses tunable from (1) 775 to 1000 nm and (2) 1030 to 1280 nm in an all-fiber configuration.

A feature of the proposed research is to harvest the recent development in femtosecond fiber sources and the latest breakthrough in fiber optic communication industry. During the course of our research and development in both academia and industry over the last 5 years, we have accumulated significant amount of preliminary data to support our approach. Specifically, we present below our studies on femtosecond fiber sources, HOM fibers, and SSFS, three key components of the proposed femtosecond source.

Figure 10A:
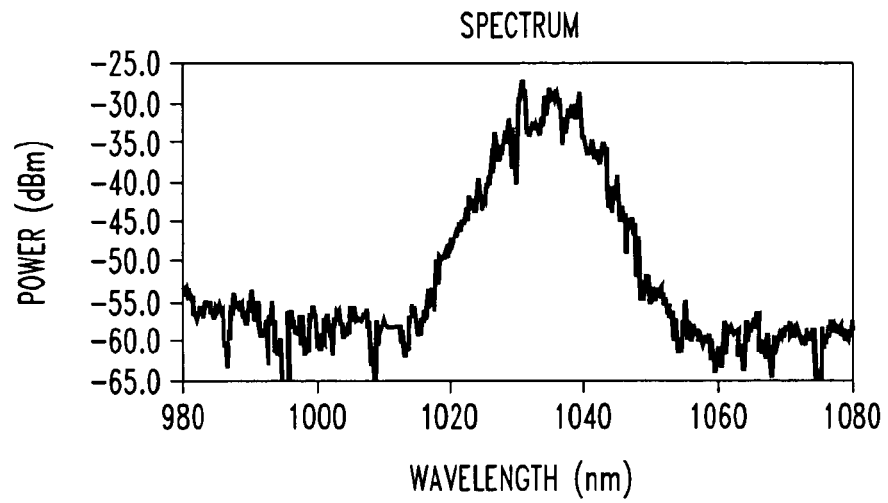
FIG. 10(a) is an output spectrum and FIG. 10(b) is a second-order autocorrelation measurement of the pulse width (~300 fs) of a commercial fiber source (Uranus 001, PolarOnyx Inc.)
Figure 10B:
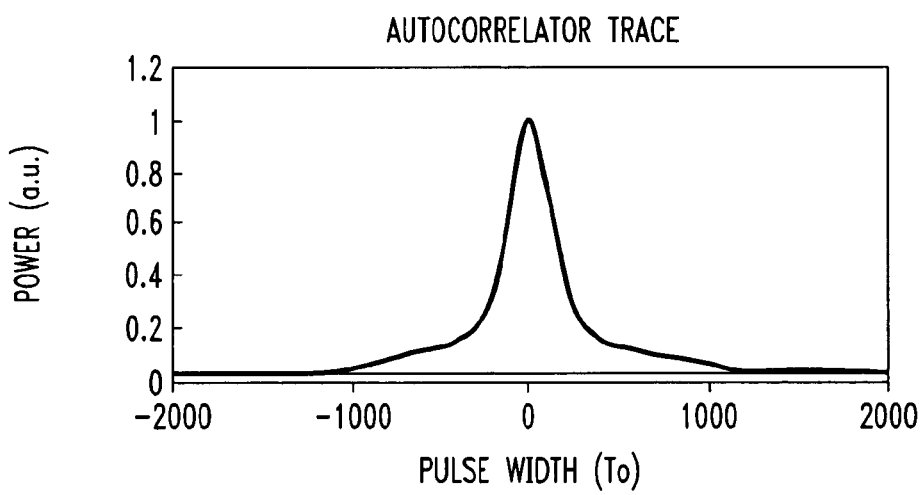
Figure 10C:
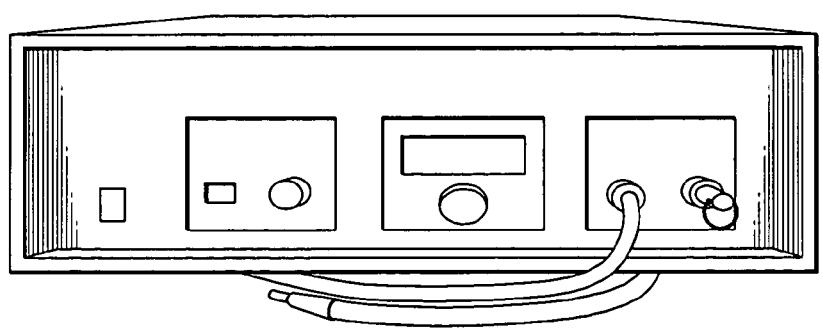
FIG. 10(c) is a photograph of the fiber source. The lateral dimension of the source is about one foot. Data and photograph courtesy of PolarOnyx Inc.

The performance of fixed wavelength femtosecond fiber sources at 1030 and 1550 nm have been improved significantly in the last several years. In fact, cost effective commercial fiber sources that are capable of delivering ~10-nJ pulse energies at 40 MHz repetition rate or higher already exist. These sources are mostly based on fiber chirped pulse amplification (CPA), where a low pulse energy oscillator serves as a seed source for the subsequent optical fiber amplifier. Examples of such sources are offered by PolarOnyx Inc. and several other companies. FIG. 10 shows the output spectrum, pulse width (autocorrelation), and the photograph of the device (in FIGS. 10(*a*), (*b*) and (*c*), respectively). The output pulse energy of the source is 14.9 nJ, and the repetition rate is 42 MHz. These sources will be sufficient to achieve our first goals of 1- to 2-nJ output pulse after SSFS.

One of the drawbacks of the commercial fiber sources is that they employ the CPA technique to achieve the pulse energies required for our application. The combination of oscillator and amplifier inevitably increases the cost of the system. Obviously, a lower cost approach will be to build a fiber oscillator that can achieve the pulse energy directly. A series of advances in femtosecond fiber lasers at wavelengths around 1 μm, based on ytterbium-doped fiber (Yb:fiber) have been reported. These include some of the best performances reported for femtosecond fiber lasers, such as the highest pulse energy (14 nJ), highest peak power (100 kW), highest average power (300 mW) and highest efficiency (45%). These are the first fiber lasers with pulse energy and peak power comparable to those of solid-state lasers. These lasers are diode-pumped through fiber spliced to the gain fiber, and are therefore already stable and reliable laboratory instruments. Uninterrupted operation for weeks at a time is routine, except when the performance is pushed to the extremes of pulse energy or pulse duration.

Figure 11:
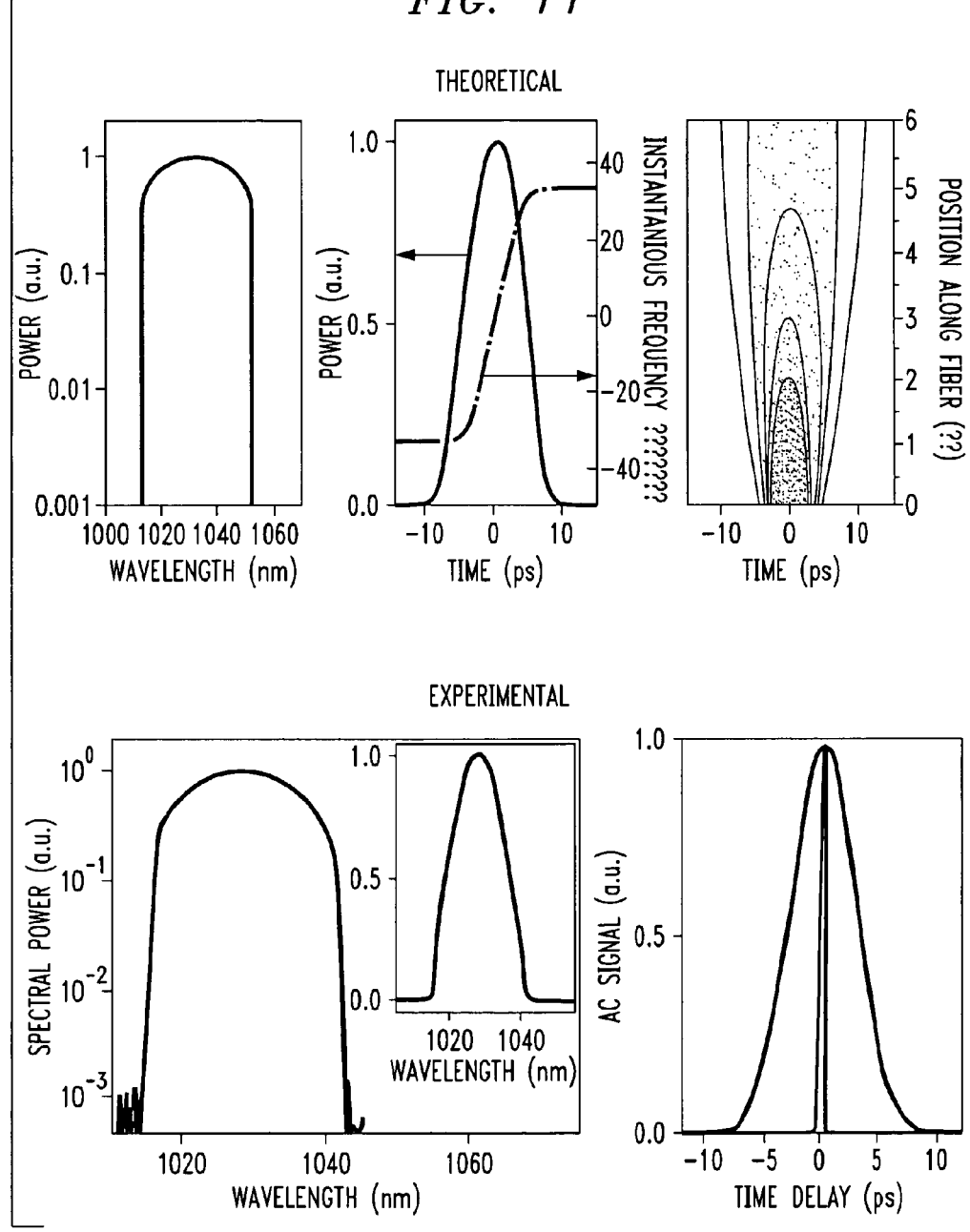
FIG. 11 shows an output of self-similar laser. Left: theoretical spectrum, output pulse, and equi-intensity contours of the pulse as it traverses the laser. Right: experimental spectrum (on logarithmic and linear scales), and measured autocorrelations of the pulse directly from the laser (broad pulse) and after dechirping (short pulse)

The science that underlies the increases in pulse energy and peak power listed above is the demonstration of pulse propagation within wave-breaking. The theoretical and experimental demonstration of "self-similar" evolution of short pulses in a laser is a major breakthrough. This is a completely new way to operate a mode-locked laser. The laser supports frequency-swept ("chirped") pulses that avoid wave-breaking despite having much higher energies than prior fiber lasers. The pulses can be dechirped to their Fourier-transform limit (FIG. 11, far-right panel), but the chirped output is actually advantageous to the design of the proposed tunable source. As illustrated by FIG. 11, the experimental performance of a self-similar laser agrees with the theoretical spectral and temporal pulse shapes. This will allow us to use the theory to scale the pulse energy to what is needed for the present project, as well as to design self-similar lasers at 1.55 μm based on erbium-doped fiber (Er:fiber). The maximum pulse energy reported from a femtosecond Er:fiber laser remains at ~1 nJ, because there has been no attempt to develop self-similar lasers at 1.55 μm yet.

The high-energy lasers described above are experimental systems. They employ some bulk optical components in the cavity, such as diffraction gratings for anomalous group-velocity dispersion. These components naturally detract from the benefits of the fiber medium, and integrated versions of these devices will be needed for most applications. Virtually all of the components of the lasers are now available in fiber format, and several advances toward the ultimate goal of all-fiber and environmentally-stable devices were made in the past few years. The first step is to replace the diffraction gratings with a fiber device. Microstructure fibers, which have become commercially available in the past couple years, offer new combinations of dispersion control with a PCF was the first such application of microstructure fibers. The resulting laser is limited to low pulse energies by the small $A_{eff}$ of the PCF. The extension of this approach to air-core PBF is quite promising as it will enable all-fiber lasers capable of wave-breaking-free operation.

Lasers with segments of ordinary fiber are susceptible to environmental perturbations such as strain or temperature changes. For ultimate stability, it will be desirable to construct lasers with polarization-maintaining fiber. We exploited the fact that photonic-bandgap fiber is effectively a polarization-maintaining fiber owing to the high index contrast, to build the first environmentally-stable laser at 1 μm wavelength. This laser operates stably when the fiber is moved, twisted or heated. All the components of the laser (which was a testbed for new concepts) now exist in fiber format. It is therefore now possible to design lasers in which the light never leaves the fiber, and which are impervious to environmental perturbations.

Our development in robust femtosecond fiber lasers has already attracted significant commercial interests. PolarOnyx, Inc. (Sunnyvale, Calif.), and Clark/MXR, Inc. (Dexter, Mich.) have introduced products based on the lasers described above (see FIG. 10 for the PolarOnyx source). The appearance of commercial products two years after the initial reports of new concepts is evidence of the robust nature of the pulse-shaping in the lasers.

The present invention is directed to an arrangement for producing high energy, femtosecond output light pulses over a tunable wavelength range for wavelengths less than 1300 nm, using a relatively new type of fiber—higher-order-mode (HOM) fiber that yields strong anomalous dispersion in the output wavelength range. Advantageously, the HOM fiber is an all-solid silica fiber structure (i.e., does not include air gaps or other microstructures) where the guidance mechanism is conventional index guiding. This represents a major breakthrough in fiber design, inasmuch as it was not previously considered possible to obtain anomalous dispersion at wavelengths shorter than 1300 nm in an all-silica optical fiber.

In accordance with the present invention, a higher-order-mode (HOM) fiber has been developed that is capable of achieving a strong positive (anomalous) waveguide dispersion ($D_w$) for the $LP_{02}$ mode at wavelengths less than 1300 nm. In particular, an HOM fiber has been formed that exhibits +60 ps/km-nm dispersion for the $LP_{02}$ mode in the 1060-nm wavelength range. Combined with in-fiber gratings, this result has enabled the construction of an HOM anomalous dispersion element (hereinafter referred to as an "HOM module") with low loss (~1%), and an effective area $A_{eff}$ (e.g., ~44 $\mu m^2$) that is ten times larger than conventional photonic crystal fibers (PCFs). Significantly, the guidance mechanism is index-guiding, as in standard fibers. Therefore, the inventive HOM fiber retains the desirable properties of such fibers, including low loss, bend resistance, and lengthwise invariance (in terms of loss, dispersion, etc.), making such a fiber attractive for a variety of applications. By utilizing the phenomenon of SSFS, for example, an input optical signal at a first, input wavelength can be shifted to a second, output wavelength after propagating through the HOM fiber of the present invention. Additionally, an HOM fiber module in accordance with the present invention can be used as a femtosecond fiber source at 1300 nm using soliton Cherenkov radiation in the HOM fiber to efficiently converter a 1030 nm femtosecond fiber source to the desired 1300 nm wavelength.

Figure 12:
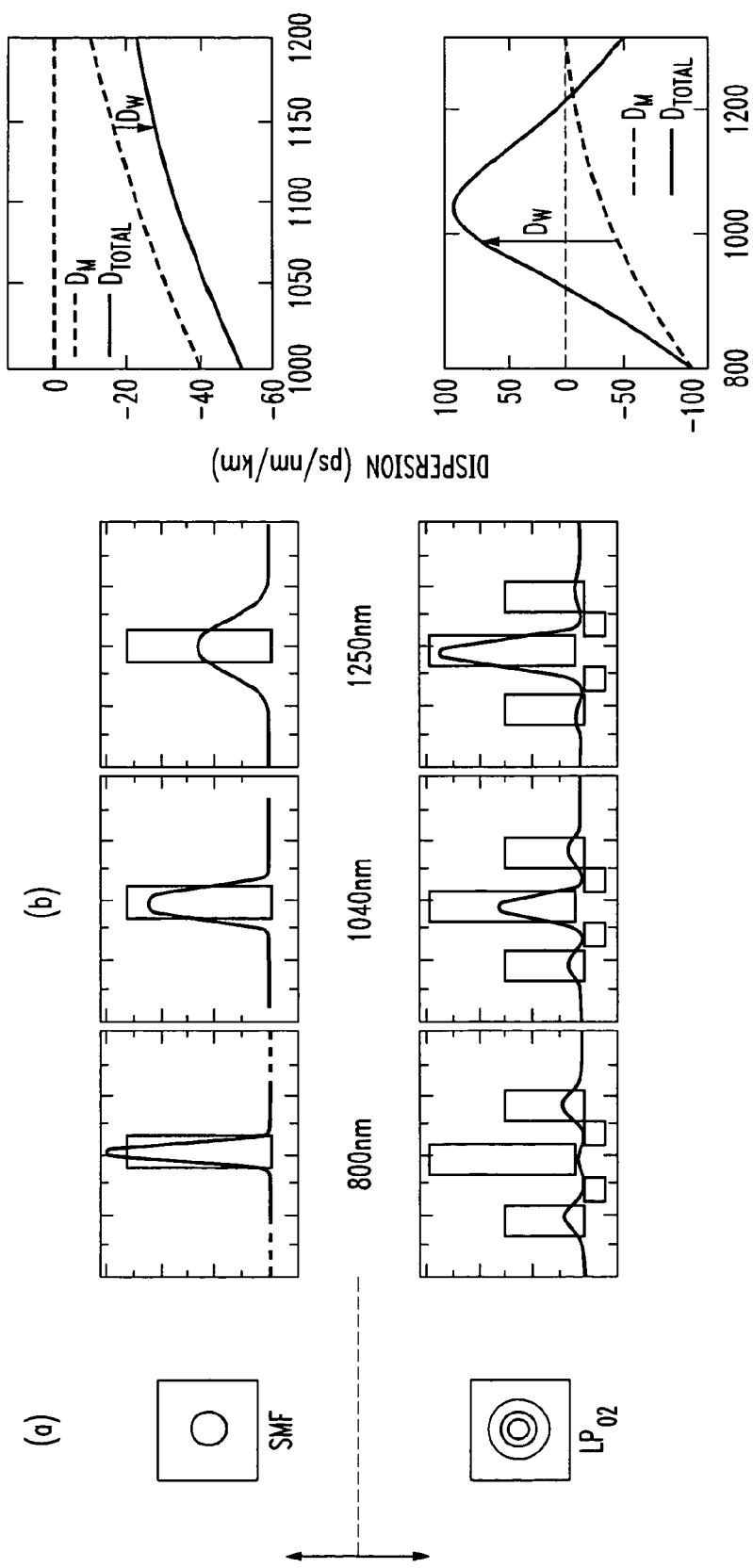
FIG. 12 shows a comparison of modal behavior between conventional LP$_{01}$ (single mode fiber, top-schematic) and LP$_{02}$ (bottom-simulated) modes.

FIG. 12 provides an intuitive picture for the dispersive behavior of the guided modes by comparing the properties of the $LP_{01}$ mode typically associated with convention single mode fiber, and the $LP_{02}$ mode as supported within the inventive HOM fiber. In particular, FIG. 12(a) shows modal images for the fundamental $LP_{01}$ mode (top) and the higher order $LP_{02}$ mode (bottom). FIG. 12(b) shows the evolution of these mode profiles as a function of wavelength, in particular at 800 nm, 1040 nm and 1250 nm. The gray background in FIG. 12(b) is used to illustrate the refractive index profile of the fiber.

As shown in the top set of modal images, the $LP_{01}$ mode monotonically transitions from the high index central core to the surrounding lower index regions as the wavelength increases from 800 nm to 1040 nm, and finally to 1250 nm. Thus, the fraction of power traveling in lower index regions increases with increasing wavelength. Since the velocity of light increases as the refractive index of the medium drops, the $LP_{01}$ mode experiences smaller group delays as wavelength increases.

Waveguide dispersion ($D_w$), which is the derivative of group delay with respect to wavelength, is thus negative for the $LP_{01}$ mode. Therefore, in wavelength ranges in which material dispersion ($D_m$) is itself negative, the conventional $LP_{01}$ mode can achieve only negative total dispersion values, where "total dispersion" $D_{total}$ is defined as the sum of waveguide dispersion and material dispersion. This is illustrated in FIG. 12(c) (top), which plots material dispersion $D_m$ as well as total dispersion $D_{total}$ of the $LP_{01}$ mode in the 1060-nm wavelength range.

In contrast and in accordance with the present invention, the higher-order $LP_{02}$ mode is designed to have the mode evolution shown in FIG. 12(b) (bottom). Again, the gray background is used to illustrate the refractive index profile for the fiber supporting this mode. As shown, when the wavelength increases from 800 nm to 1040 nm, and then to 1250 nm, the mode evolves in the opposite direction as the conventional fiber described above. That is, with reference to the diagrams along the bottom of FIG. 12(b), the mode transitions from the lower index regions to the higher index core as the wavelength increases from 800 nm to 1250 nm. The $LP_{02}$ mode thus experiences larger group delays as the wavelength increases.

Therefore, the $LP_{02}$ mode will exhibit a wavelength dispersion $D_w$ that is positive over this entire range as the mode transitions from the cladding to the core. This is illustrated in FIG. 12(c) (bottom), which shows the wavelength range where this transition occurs. Indeed, very large positive values of $D_w$ may be obtained, vastly exceeding the magnitude of the material dispersion $D_m$ (which, as mentioned above, is negative over the same range). As a result of the substantial difference in magnitude between the waveguide dispersion and the material dispersion, the $LP_{02}$ mode that propagates along an HOM fiber will exhibit a total dispersion $D_{total}$ that is positive (anomalous dispersion).

It is to be noted that this evolution is governed by the "attractive" potential of various high index regions of the waveguide, and can thus be modified to achieve a variety of dispersion magnitudes, slopes and bandwidths. This yields a generalized recipe to obtain positive dispersion in a variety of wavelength ranges.

Figure 13:
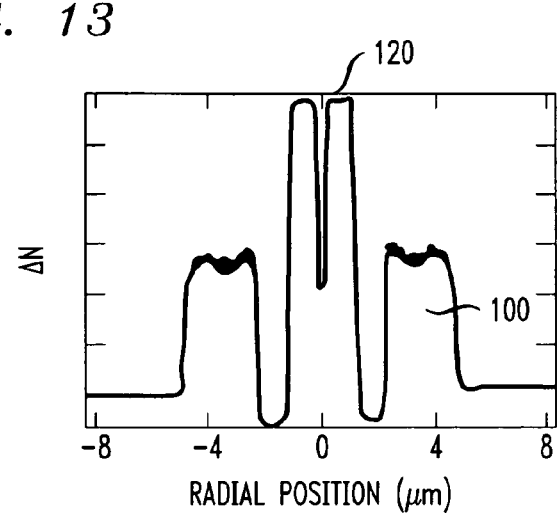
FIG. 13 is an index profile of the HOM fiber.
Figure 14:
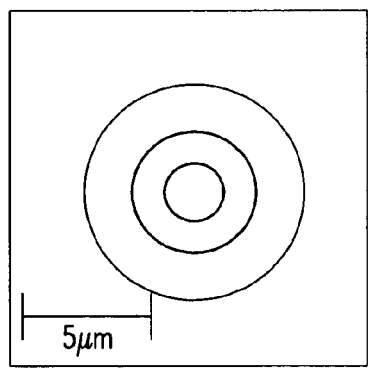
FIG. 14 shows an experimentally measured near-field image $LP_{02}$ mode with an effective area $A_{eff} \sim 44$ μm$^2$.

FIG. 13 shows the index profile of an exemplary HOM fiber formed in accordance with the present invention to provide this positive dispersion value, where a broad, low index ring 100 serves to substantially guide the $LP_{02}$ mode at shorter wavelengths. As described above, the mode will then transition to a small, high index core 120 as wavelength increases (as described above in association with FIG. 12(b), bottom). The experimentally recorded near-field image of this $LP_{02}$ mode is shown in FIG. 14, where measurements have shown that this exemplary HOM fiber will exhibit an effective area $A_{eff}$ of approximately 44 $\mu m^2$ at 1080 nm.

The well-known physics of SSFS dictates that the wavelength tuning range is limited by the range within which the dispersion of the fiber mode is anomalous (positive). In other words, for a tuning range of $\lambda_{tuning}$, the dispersion-zero crossings of the dispersion curves must also be separated by at least the same amount $\lambda_{tuning}$. For many applications, it is desirable that this range be at least 300 nm. More broadly, a tuning range anywhere between 10 nm and 2000 nm may be considered useful. In general, the range of such tuning, and correspondingly the energy carried by the shifted soliton, scale with $D^*A_{eff}$ for the wavelength and the mode in which the soliton signal resides.

The well-known physics of generation of Cherenkov radiation, on the other hand, requires the existence of a zero-dispersion crossing. If an optical soliton exists in its vicinity in the anomalous dispersion wavelength range, then Cherenkov radiation is generated in the spectral region on the other side of this zero-dispersion wavelength—i.e., in the region where the dispersion is normal. The exact spectral location of the generated wave is further governed by the dispersion slope of the fiber mode. Again, the energy of the converted radiation scales as $D^*A_{eff}$ for the mode in which the optical radiation resides.

Figure 15:
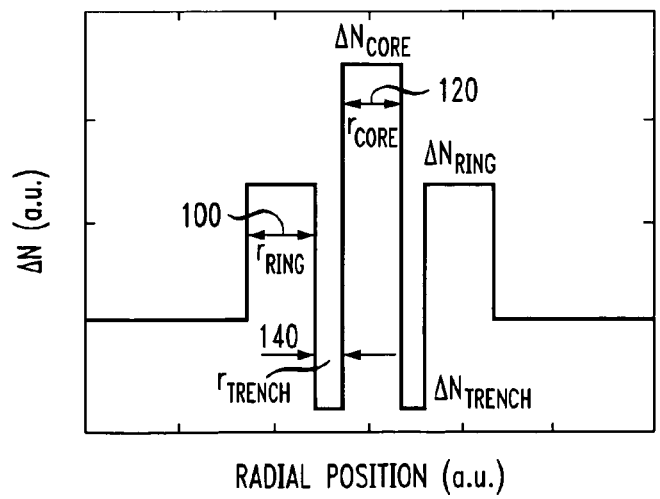
FIG. 15 is a refractive index profile for an HOM fiber of the present invention, indicating the set of six different parameters than may be adjusted to provide the desired positive dispersion and large effective area.

In accordance with the present invention, therefore, the fiber design problem reduces to one of configuring an HOM fiber with the required value of $D^*A_{eff}$ at the output wavelengths of the dispersion curve. The general fiber index profile for achieving $D_w>0$ for the $LP_{02}$ mode is shown in FIG. 15. While FIG. 12 provides the physical intuition for $D_w>0$ in an HOM fiber, achieving target dispersion D and effective area $A_{eff}$ values requires a numerical optimization of the six parameters shown in FIG. 13, namely, the indices and dimensions of ring 100, trench 140 and core 120. There are two ways to achieve a large dispersion (D) value; one is by increasing refractive index values $\Delta N_{core}$ and $\Delta N_{ring}$, but this may be at the expense of the effective area $A_{eff}$. The second approach is by increasing $r_{ring}$ as well as $r_{trench}$. Increasing $r_{ring}$ will enhance the mode size, while increasing $r_{trench}$ will provide for greater effective index changes as the mode transitions, resulting in larger dispersion.

The key to achieving the desired properties is a mode that can transition (as a function of wavelength) through well-defined, sharp index steps in the fiber's index profile. Therefore, the fabrication process must be capable of producing both large index steps as well as steep index gradients, as shown in FIG. 15. The ideal means to achieve this is the Modified Chemical Vapor Deposition (MCVD) process, which affords the best layer-to-layer control of refractive index of all established fabrication technologies for fibers.

Dimensional scaling of the preform can also be used to shift the waveguide dispersion $D_w$ in order to achieve the $D^*A_{eff}$ necessary for the desired output wavelength ranges. This is known in the art of optical waveguides as complementary scaling, which states that wavelength and dimension play a complementary role in the wave equation and, therefore, are interchangeable. However, it is to be noted that this is true only for the waveguide component of dispersion, $D_w$. Changes in the material dispersion, $D_m$, are not complementary and, as a result, the total dispersion D is not wavelength scalable. In other words, to move the dispersion curve that provides satisfactory operation in the 1030 nm wavelength range to the 775 nm spectral range, the dispersion $D_w$ needs to be high enough to counteract the strong negative trend for $D_m$ as wavelength decreases. Therefore, achieving similar properties at lower wavelengths needs the use of both dimensional scaling and the above-described dispersion-increasing configurations.

Figure 16:
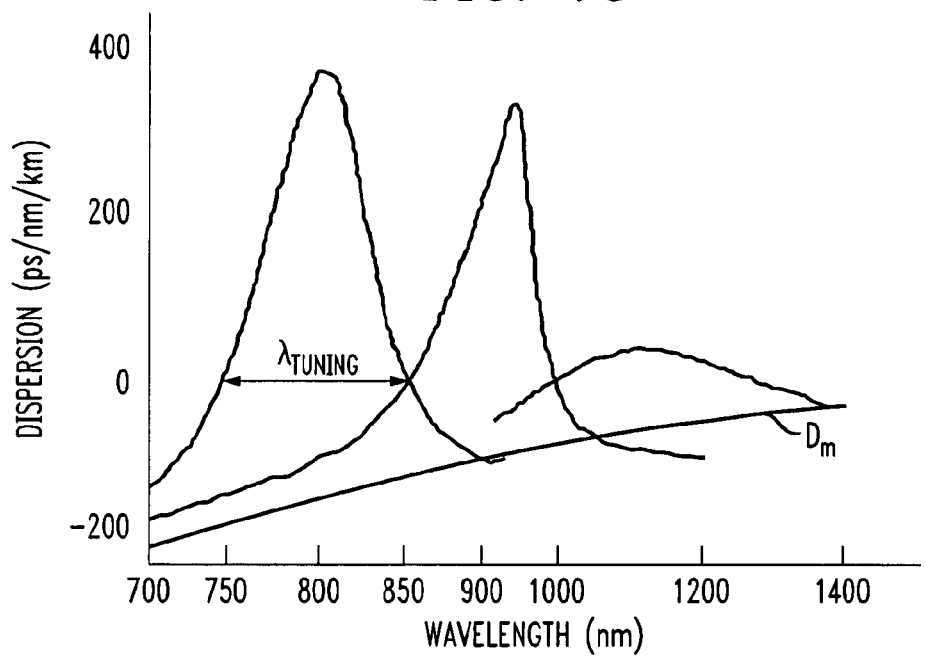
FIG. 16 is a graph of the simulated total dispersion vs. wavelength curves for a variety of profiles, forming by adjusting one or more of the parameters shown in FIG. 15.

To achieve the higher 5- to 10-nJ output pulse energies, the design of an inventive HOM in this range requires a $D^*A_{eff}$ value that is five to ten times greater than that associated with providing output pulses in the 1-2 nJ range. The main difficulty is to simultaneously achieve the large values of $D^*A_{eff}$ while maintaining $\lambda_{tuning}$ at approximately 300 nm. FIG. 16 illustrates the simulated total D vs. wavelength curves for a variety of acceptable profiles, where the material dispersion value of silica, $D_m$, is also shown. An important constraint applied in generating the profiles shown in FIG. 16 is that the effective index $n_{eff}$ of the HOM in which signal propagation is desired (i.e., the mode for which the dispersion curves are shown), is vastly separated from the $n_{eff}$ of any other mode that may be guided in the fiber. The large separation in $n_{eff}$ between modes ensures that the signal that is introduced in the HOM predominantly propagates only in that mode and does not randomly coupled to any other mode. Such random coupling may occur due to bends and other environmental perturbations, and typically the $n_{eff}$ difference between the modes should be greater than $10^{-5}$ to avoid this type of coupling.

Figure 17:
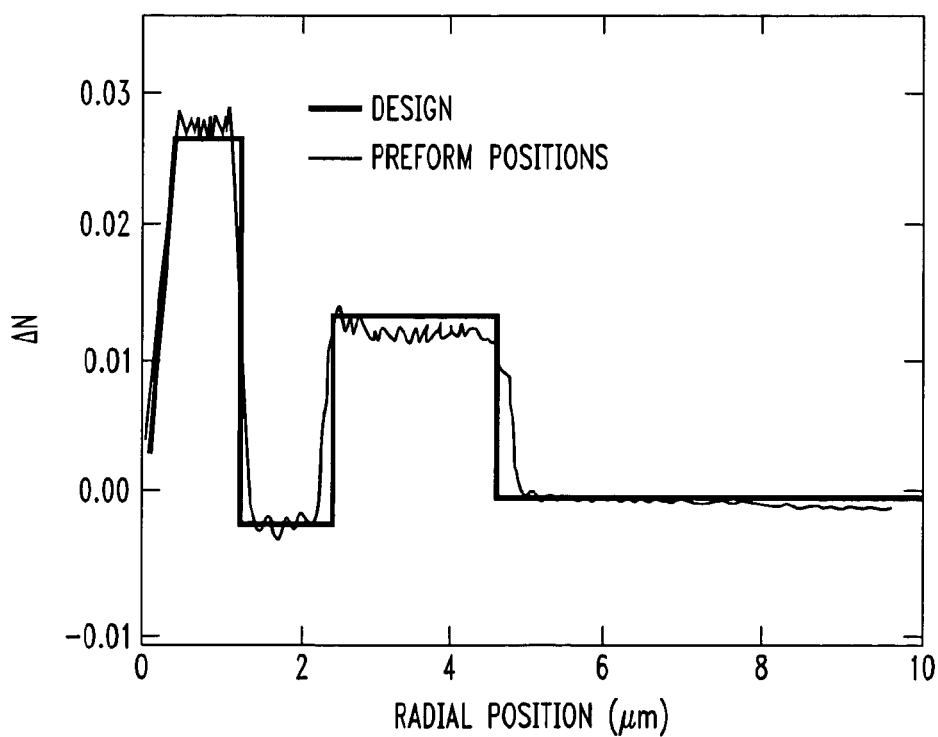
FIG. 17 shows index vs. radial position of the designed and fabricated fiber measured at several perform positions.

FIG. 17 shows an example of the designed and fabricated index profiles for an HOM fiber formed in accordance with the present invention that yields a large positive dispersion in the 1060-nm wavelength range. The preform profiles closely match the design profile in both index values and the steep index gradients. Also shown in FIG. 17 are index profiles from different sections of the preform, showing the uniformity of the MCVD process in fabrication an HOM fiber whose properties are invariant as a function of fiber length. This robust fiber fabrication process is critical to provide a constant zero-dispersion wavelength in an HOM fiber for SSFS, and is a significant advantage of the inventive HOM fiber over the prior art bandgap fibers.

Figure 18:
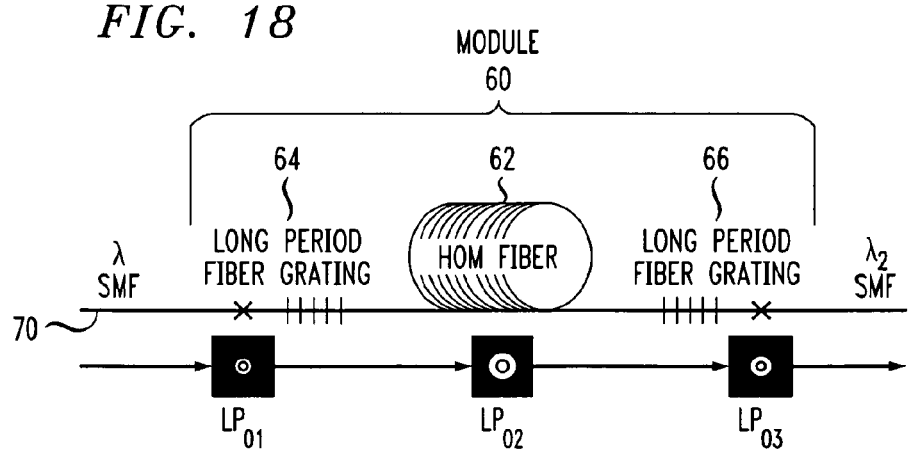
FIG. 18 illustrates an exemplary HOM module for converting an input wavelength to a desired output wavelength in accordance with the present invention.

FIG. 18 illustrates an exemplary wavelength converting HOM module 60 formed in accordance with the present invention, including a section of HOM fiber 62 having the characteristics as described above in association with the above FIGS. 15-17 to provide high energy femtosecond pulses at wavelengths less than 1300 nm. In accordance with the present invention, HOM module 60 utilizes SSFS, or a combination of SSFS with Cherenkov radiation, to shift the wavelength of an incoming signal to an output wavelength selected for a specific application (the output wavelength less than 1300 nm).

Further, in accordance with the present invention, HOM module 60 provides for dispersion compensation prior to wavelength shifting, such that chirped incoming pulses (i.e., pulses with a linear chirp of at least 5.25 ps/nm) are "de-chirped" with the required amount of dispersion within HOM fiber 62. Thereafter, the de-chirped pulses undergo SSFS and/or Cherenkov radiation to generate the output pulses at the desired wavelength.

For proper operation of HOM module 60, an input mode converter 64 is needed to convert an incoming Gaussian-shaped $LP_{01}$ mode signal into the desired $LP_{02}$ mode. One preferred method for providing the mode conversion is with one or more in-fiber long period gratings (LPGs). This type of grating can be permanently formed in fibers by lithographically transferring a grating pattern from an amplitude mask to the fiber using a UV laser. For efficient grating formation, the fiber is typically saturated with deuterium, which acts as a catalyst for the process, resulting in UV-induced index changes in the germanosilicate glass. In another embodiment, the input mode converter may convert any arbitrary incoming spatial profile of light into the HOM that is desired to be propagated in the HOM fiber. For some applications, an output mode converter may be used to transform the higher-order-mode into another spatial mode. In the illustration of FIG. 18, an output mode converter 66 is shown as disposed at the output of HOM fiber 22 to transition the wavelength-shifted $LP_{02}$ mode signal back into a conventional $LP_{01}$ signal. More generally, an output mode converter can be used to convert the HOM into any desired spatial profile of light.

Alternatively, in some applications, it may be desired that no output mode converter is used, inasmuch as the wavelength-shifted radiation already exhibits the desired spatial mode profile. In these cases, therefore, the need for an output mode converted is obviated. In yet another embodiment, the HOM module may comprise a plurality of separate HOM fiber sections coupled together in series, using fiber splicing techniques or another mode converter to join together the adjacent sections. If they are joined by splices, the HOM in the first fiber is expected to adiabatically transition to the same mode order in the second fiber. If they are joined together by means of a mode converter, on the other hand, the mode order from the first fiber to the second fiber can also be changed. Such arrangements may be desired in applications where, in order to increase the $\lambda_{tuning}$ for SSFS, two concatenated sections will provide a much larger tuning range than that associated within only a single HOM fiber section. Alternatively, such arrangements may allow for changing the dispersion slope of the zero-dispersion crossing, as may be required for adjusting the wavelength at which Cherenkov radiation occurs. In the case where a mode converter is used to join two sections of HOM fiber, it is known from the prior art that such mode converters may be tunable, with the capability of switching light from one incoming HOM fiber to any of a set of outgoing HOM fibers (including, of course, reflecting back into the incoming HOM fiber). If a tunable mode converted is employed in this case, the resulting HOM module will additional provide a means to dynamically change the effective optical path length of the fiber and, by extension, its dispersion, dispersion-zero and/or dispersion slope (as may be desired for different SSFS and Cherenkov applications). Thus, a module with adjustable HOM fiber lengths may be designed and is considered to fall within the scope of the present invention. Indeed, in embodiments that utilize a multiple-number of concatenated HOM fiber sections, tunable mode converters may be used at the interface between any two sections.

Figure 19A:
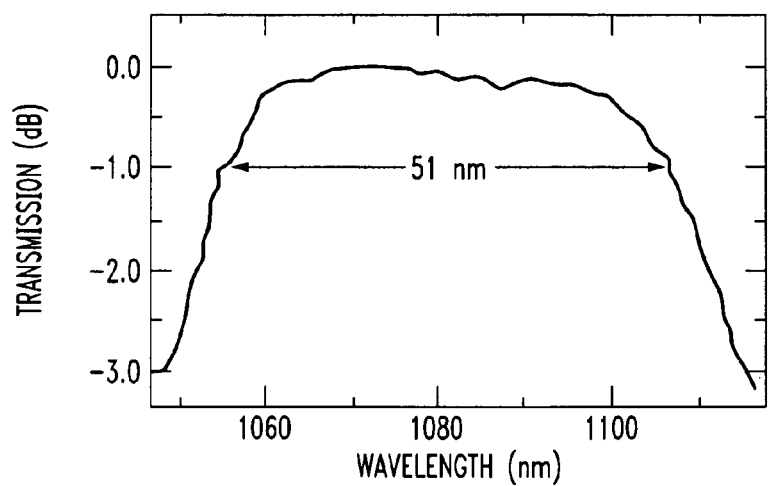
FIG. 19(a) is a plot of the bandwidth of the HOM module of FIG. 18.
Figure 19B:
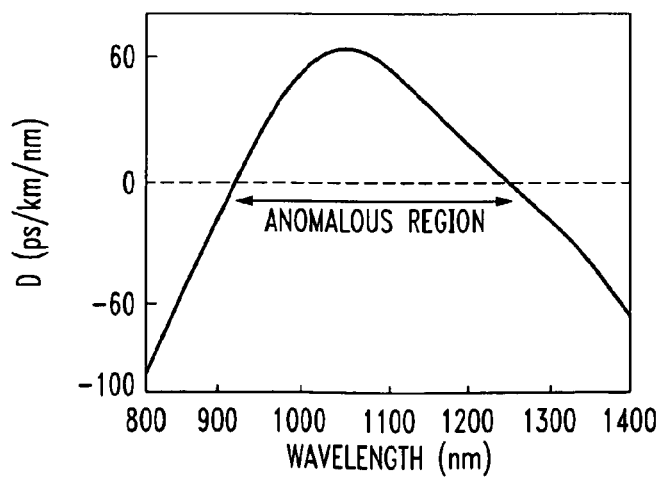
FIG. 19(b): Comparison of the dispersions of the HOM fiber (solid) and the conventional SMF (dashed). Also shown is the zero-dispersion line (dotted)
Figure 19C:
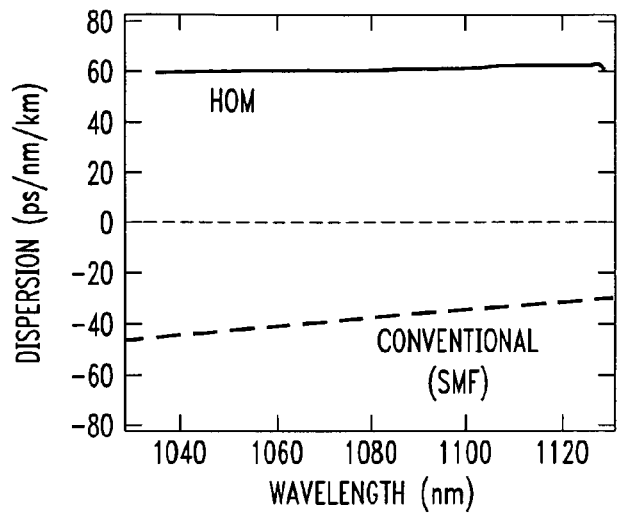
FIG. 19(c): Comparison of the dispersions over the narrow range of 1040 to 1120 nm.

LPGs offer coupling between co-propagating modes of a fiber and have found a variety of applications as spectral shaping elements and mode-conversion devices. However, LPGs are normally narrow-band devices, and while they offer strong mode coupling (>99%), the spectral width of such coupling was typically limited to a range of 0.5 to 2 nm, too narrow for a femtosecond pulse. To overcome the spectral limitation, reports have shown that the LPG bandwidth can be extended to greater than 60 nm in some cases, if the fiber waveguide is configured to yield two modes with identical group velocities. It is to be noted that the large bandwidth of HOM module 20, as shown in FIG. 19($a$) (i.e., approximately 51 nm), is uniquely enabled by the dispersive design of the fiber, which enables matching the group velocities of the two coupled modes. It is a significant aspect of the present invention that the utilization of the LPGs allows for the formation of an "all-fiber" tunable femtosecond pulse source.

Referring again to FIG. 18, HOM module 60 is spliced to an input single mode fiber 70 at input long period grating 64. The splice between single mode fiber 70 and input LPG 64 is configured such that the signal predominantly resides in the $LP_{01}$ mode, thus ensuring mode conversion with high efficiency and also minimizing signal propagating in any mode other than the desired mode. This enables a device to be constructed in which the signal experiences high modal stability, even in the presence of bends and other environmental perturbations. Indeed, input single mode fiber 70 may be the output fiber of a laser source (not shown), avoiding any spurious mode coupling, especially in systems where the chirped output of the laser source needs to be directly coupled into the HOM fiber module.

As mentioned above, output long period grating 66 is used to convert the beam back to a Gaussian output. Dispersion-matching configurations are preferably used that yield ultra-large bandwidths, ensuring that the output pulse is always converted back to a Gaussian profile, within a tuning range of approximately 250 nm. An important consideration for output grating 66 is its length. Since the energetic output pulses are solitons for the specific combination of dispersion D and effective area $A_{eff}$ of the $LP_{02}$ mode, nonlinear distortions may occur when the signal converts to the $LP_{01}$ mode (having a smaller $A_{eff}$) at the output. However, the length over which the signal travels in the $LP_{01}$ mode, and hence the distortion it accumulates, can be minimized. The high index core of HOM fiber 62 enables the use of an output long period grating 66 of lengths less than 5 mm, which implies that light resides in the $LP_{01}$ mode for less than 2.5 mm and therefore largely avoids nonlinear distortions. It is to be noted that the requirement for "short" LPGs actually complements the need for broad bandwidth operation, since the conversion bandwidth is typically inversely proportional to the grating length.

FIG. 19($b$) shows the central parameter of interest—the dispersion of the $LP_{02}$ mode, as measured by spectral interferometry. The dispersion is +60 ps/nm-km at 1080 nm. The $A_{eff}$ of this fiber (44 $\mu m^2$) is an order of magnitude larger than PCFs with similar dispersion (PCF $A_{eff}$~4 $\mu m^2$), and is in fact larger than that of commercial SMFs at these wavelengths (SMF $A_{eff}$~32 $m^2$). FIG. 19($c$) again illustrates the dispersion of the $LP_{02}$ mode, in this case over the narrow range of 1040 to 1120 nm. The dispersion is +60 ps/nm-km at 1080 nm. The $A_{eff}$ of this fiber (44 $\mu m^2$) is an order of magnitude larger than PCFs with similar dispersion (PCF $A_{eff}$~4 $\mu m^2$), and is in fact larger than that of commercial SMFs at these wavelengths (SMF $A_{eff}$~32 $\mu m^2$).

Figure 20A:
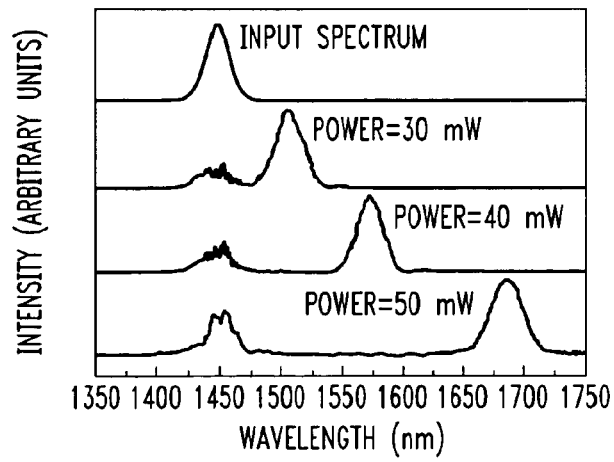
FIG. 20 is a demonstration of SSFS in a tapered PCF (inset in b). (a) Output spectra at different values of output soliton power. (b) Measured wavelength shift vs. input power.
Figure 20B:
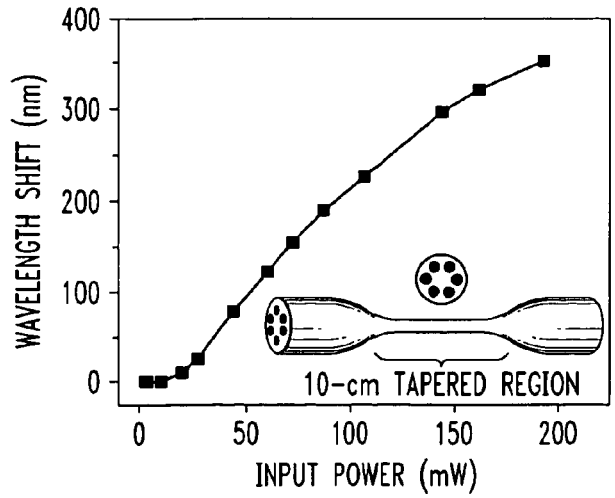
Figure 21:
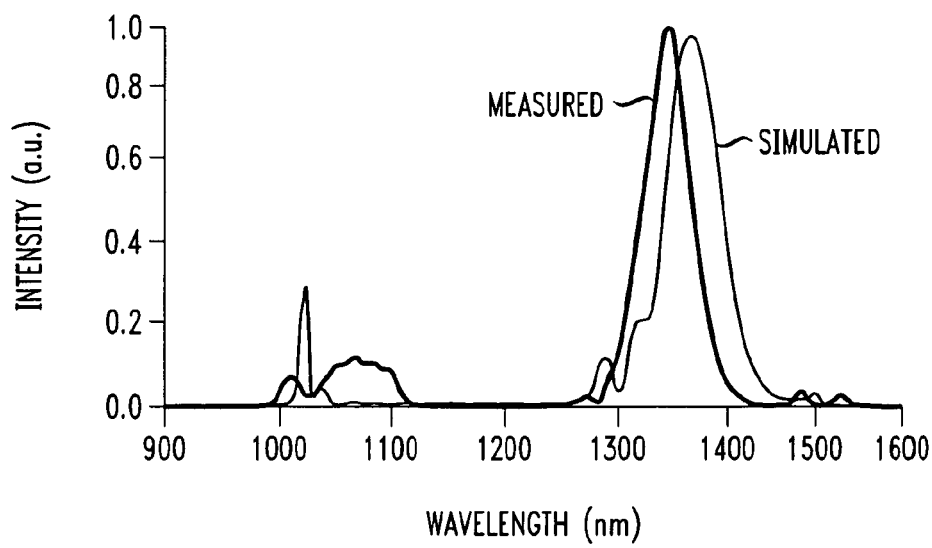
FIG. 21 shows results of SSFS in a PCF. A pulse at 1030 nm is shifted to beyond 1300 nm in this example. Result of numerical simulation is shown for comparison.

There are a number of theoretical and experimental works on SSFS in the past, including some targeting biomedical applications. Reports have demonstrated SSFS in a number of fiber structures within the last 5 years. Previously, a novel tapered air-silica microstructure fiber was fabricated and demonstrated SSFS within the telecom window of 1.3 $\mu m$ to 1.65 $\mu m$ in a 10-cm long tapered microstructure fiber (inset in FIG. 20($b$)). By varying the input power into the fiber, clean self-frequency-shifted solitons were observed with a maximum wavelength shift of 300 nm (FIG. 20($a$)). Over 60% photons were converted to the frequency-shifted soliton. The experimental dependence of soliton wavelength shift upon the incident power is shown in FIG. 20($b$). Similar experiments were also demonstrated using a mode-locked fiber laser and PCF, shifting of the pulse wavelength continuously from 1 to 1.3 $\mu m$, with ~1 m of photonic-crystal fiber (FIG. 21). Despite these early works by ourselves and colleagues in the field, the highest soliton pulse energy of 0.1 to 0.4 nJ were obtained at 1030 to 1330 nm, still substantially below 1 nJ.

Figure 22:
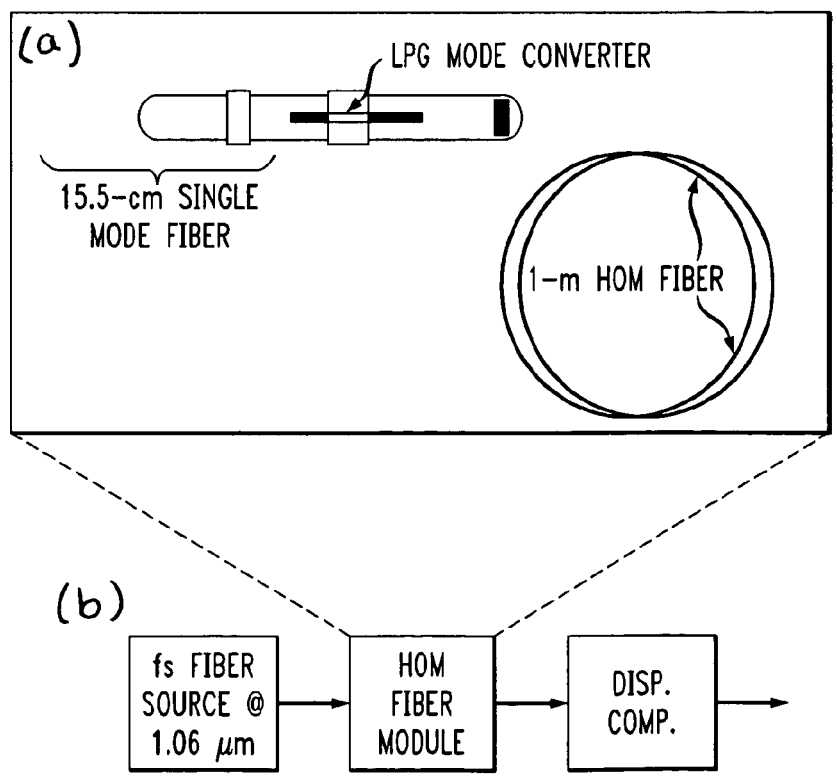
FIG. 22(a) is a photo of the HOM fiber module for the demonstration of Cherenkov radiation.
FIG. 22(b) is an associated block diagram showing the placement of the HOM fiber module in the overall system. The splice protector also protects the in-fiber FPG mode converter.
Figure 23:
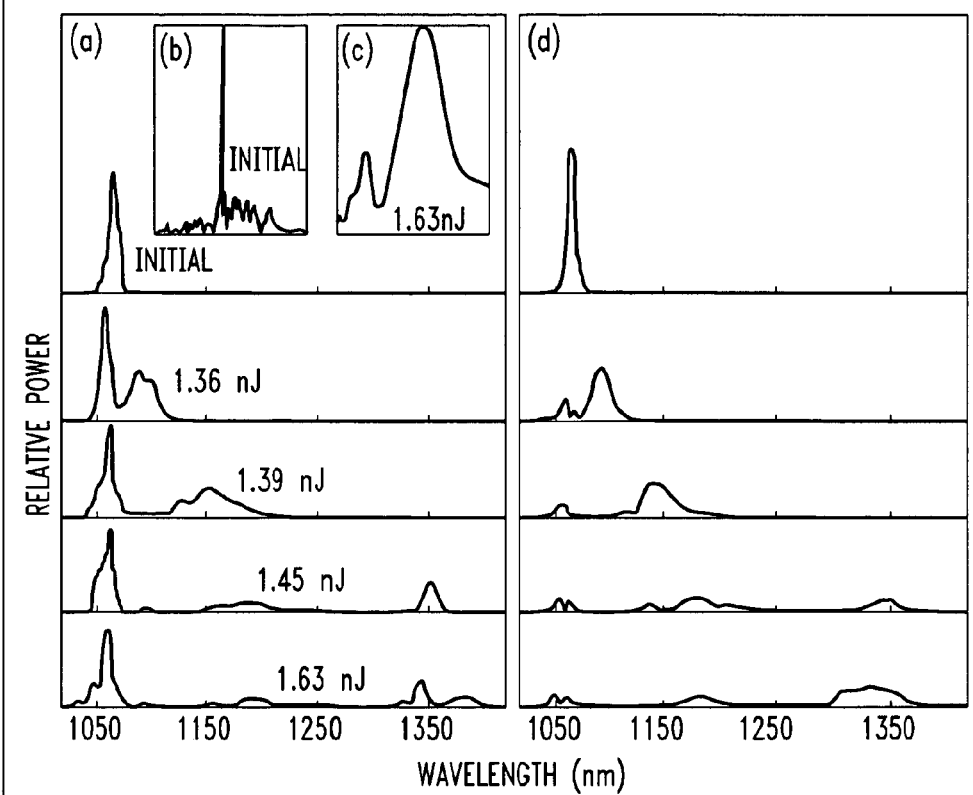
FIG. 23(a): Soliton self-frequency shifted and Cherenkov spectra corresponding to different input pulse energies into the HOM fiber of FIG. 22(b)
FIG. 23(b): High resolution trace of the initial spectrum.
FIG. 23(c): High resolution trace of the shifted soliton for 1.63 nJ input into the HOM.
FIG. 23(d): Soliton self-frequency shifted and Cherenkov spectra calculated from simulation.
Figure 23:
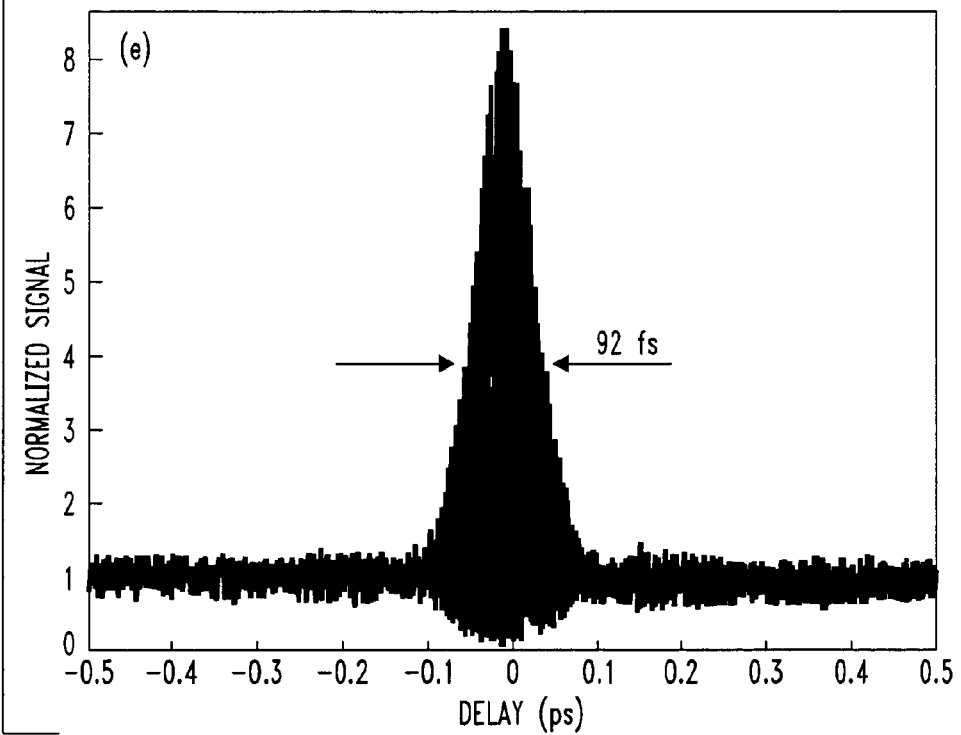

Our recent breakthrough in the HOM fiber provides an exciting new opportunity for SSFS at the practical pulse energies of 1 to 10 nJ and at wavelength below 1300 nm. We have experimentally investigated the behavior of SSFS at Cornell using the HOM fiber module provided by OFS. FIGS. 22 and 23 respectively show the experimental setup and results. Despite the fact that the HOM fiber module we used for the demonstration was designed for telecommunication purposes and was not ideally suited for SSFS at 1060-nm input, and the fact that the input pulse (inset in FIG. 23) from our commercial fiber source (Fianium, UK) is far from perfect, our preliminary results unequivocally demonstrated the feasibility and promise of the approach proposed.

Figure 24A:
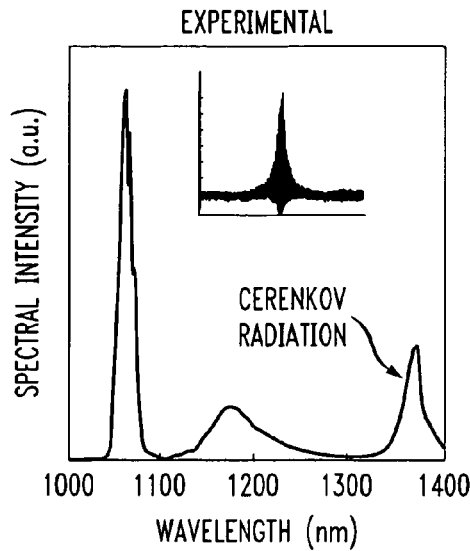
FIG. 24(a) is a measured spectral trace showing the Cherenkov radiation at the maximum achievable 2.0-nJ input power into the HOM fiber in the system of FIG. 22(b). Inset is the measured second-order interferometric autocorrelation trace (total delay of 2 ps) of the filtered Cherenkov radiation, corresponding to a deconvolved pulse width of approximately 100 fs (FWHM)
Figure 24B:
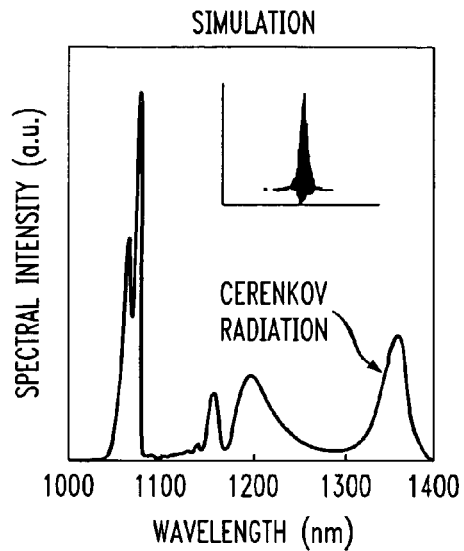
FIG. 24(b): Results from numerical simulation using the experimental parameters from FIG. 22(b). Inset is the simulated second-order interferometric autocorrelation trace of the filtered Cherenkov radiation. The input center wavelength is at 1064 nm. The spectral peaks in the middle (~1200 nm) are the Raman shifted solitons.

The maximum power that we were able to launch from our source corresponds to 2.0 nJ pulse into the HOM fiber. The output spectrum (FIG. 24($a$)) was measured by a spectrometer. The Cherenkov radiation was filtered out using a free space optical filter. After dispersion compensation to remove the linear chirp in the Cherenkov pulse, second order interferometric autocorrelation was performed to measure the pulse width (inset in FIG. 24($a$), horizontal scale is 2 ps total delay). To compare with the experimental data, we have also carried out numerical simulations using the standard split-step Fourier transform method, and the results are shown in FIG. 24($b$).

Although it was our very first attempt, and the HOM fiber was not fully optimized for soliton Cherenkov radiation, our preliminary results unequivocally demonstrated the feasibility and promise of the approach proposed. FIG. 24 clearly shows that:

1. An output pulse width of 100 fs FWHM was obtained.
2. An output pulse energy of 0.046 nJ was obtained at the center wavelength of ~1.36 µm.
3. Remarkable agreement between experiments and numerical modeling was achieved without any fitting parameter, demonstrating the reliability of our numerical prediction.

We emphasize here that the low Cherenkov energy is entirely due to the maximum input pulse energy (2.0 nJ) with our fiber source at 1.06 µm. In fact, negligible Cherenkov radiation was observed even at input pulse energy of 1.4 nJ. As we will show in the next section, our numerical modeling indicated that the existing HOM fiber should be able to provide approximately 2-nJ Cherenkov radiation at 4-nJ input. The key results are summarized below:

1. A continuous wavelength shift of ~130 nm (1060 to 1190) was achieved.
2. An output pulse energy of 0.84 nJ was obtained at 1.39-nJ input pulse.
3. A high quality output pulse with ~50-fs FWHM and a high conversion efficiency (i.e., the amount of optical power that is transferred to the wavelength shifted soliton) of ~60% were obtained despite of the low quality input pulse.
4. Remarkable agreement between experiments and numerical modeling were achieved despite of the non-ideal input, demonstrating the robustness of soliton pulse shaping.

We note that at the highest input pulse energy, a new spectral peak appeared at much longer wavelength (~1350 nm). This is the well-known resonance Cherenkov radiation of the soliton due to the negative dispersion slope, which is also predicted by our simulation (FIG. 24(b)). The onset of the Cherenkov radiation sets the long wavelength limit of the wavelength tuning range using SSFS and is highly predictable by the zero dispersion wavelength of the fiber.

Our initial success of SSFS in a HOM fiber module, and our proven capability to numerically predict the behavior of SSFS in a HOM fiber give us a high degree of confidence to achieve the stated goals. Through extensive numerical simulations, we have already determined the required dispersion (FIG. 25) and $A_{eff}$ of the HOM fibers to achieve our first goal of 1- to 2-nJ pulses, tunable from 775 to 1000 nm and 1030 to 1280 nm.

Additionally, our initial success in also generating Cherenkov radiation in an HOM fiber module, and our proven capability to numerically predict the behavior of Cherenkov radiation in an HOM fiber, also gives us a high degree of confidence to achieve the stated goals. Based on the results of our preliminary experiments, we essentially need to perform two tasks: (1) to convert the wavelength to 1300 nm instead of the 1360 nm demonstrated; (2) to increase the output pulse energy to greater than 10 nJ instead of the fraction of a nJ demonstrated. The center wavelength of the Cherenkov radiation is mostly determined by the zero dispersion wavelength and the TOD; while the Cherenkov energy is determined by the magnitude of $D*A_{eff}$. Thus, the first task can be accomplished by wavelength-shifting the dispersion curve, and the second by increasing the dispersion and/or effective area of the HOM fiber.

Figure 26A:
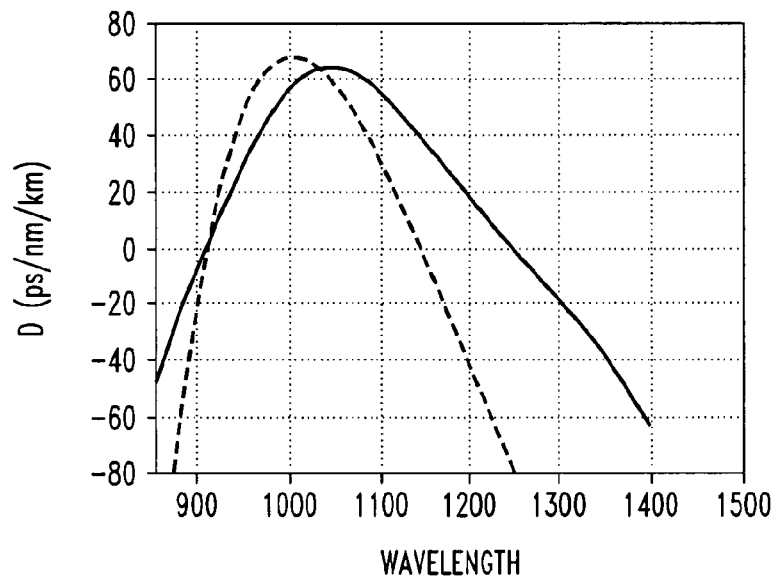
FIG. 26(a): Designed dispersion (D, dashed line) vs. wavelength for converting 1.03 μm to 1.27 μm via Cherenkov radiation. The dispersion of the existing HOM fiber (solid line) is also indicated.

A remarkable feature of soliton Cherenkov radiation is its robustness against input variations. For example, at 3.2 nJ input, our numerical modeling predicts Cherenkov radiation at 66 fs pulse width and 2 nJ, results that are very similar to those obtained at 4.2 nJ input. Numerical simulations further showed that fiber length variation from 25 to 45 cm essentially provided identical output characteristics except that the values for dispersion compensation need to be adjusted accordingly to achieve the shortest pulse. We note that the designed dispersion curve shown in FIG. 26(a) (dashed line) is of the same dispersion value as our existing HOM module except that the peak wavelength is shifted for optimum output at 1300 nm. Preliminary design simulations by the inventor indicated that such dispersion characteristics are readily achievable. We emphasize that these design studies are based on reliable in-house design tools developed at OFS, and have taken into account practical considerations such as the manufacturability and yield of the fiber. Thus, these designs are viable commercially.

Figure 26B:
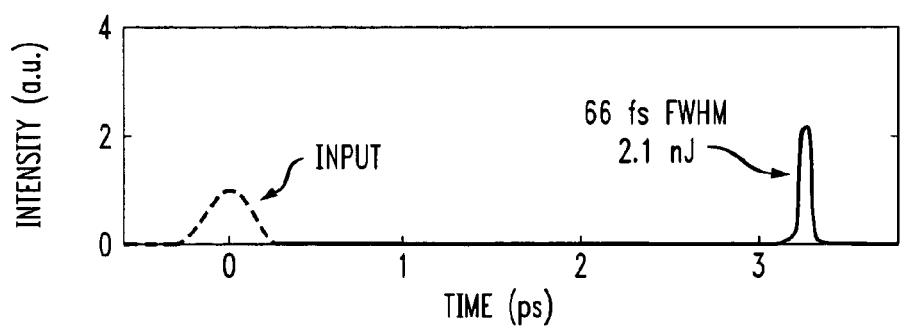
FIG. 26(b): Output intensity (top) and spectrum (bottom) after propagating through 0.25-meter of HOM fiber at an input pulse energy of 4.2 nJ. For comparison, the input spectrum (scaled down by a factor of 5) and pulse (dashed lines) are also shown. The spectral filter bandwidth is indicated.
Figure 26C:
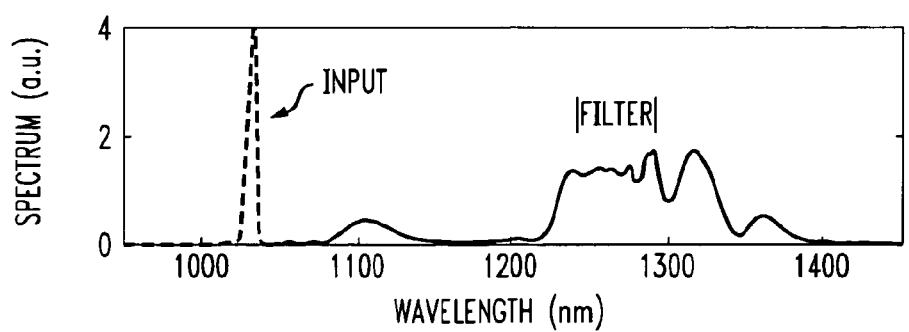

FIG. 26(b) shows numerical simulation results of the Cherenkov radiation in such HOM fibers at 4.2 nJ input. The conversion efficiency is ~50% for a Gaussian input pulse at 280-fs width (FWHM). The output pulse has a width (FWHM) of approximately ~66 fs after dispersion compensation to remove the linear chirp of the pulse. The pulse has excellent quality with more than 90% of the energy residing within the time window that is twice the FWHM. We clarify here that the local minimum for water absorption is actually located at 1270 nm instead of 1300 nm, even though it is commonly referred to as the 1300-nm spectral window. Thus, our output spectral filter (shown in FIG. 26(b) bottom) is centered at 1270 nm.

Figure 27A:
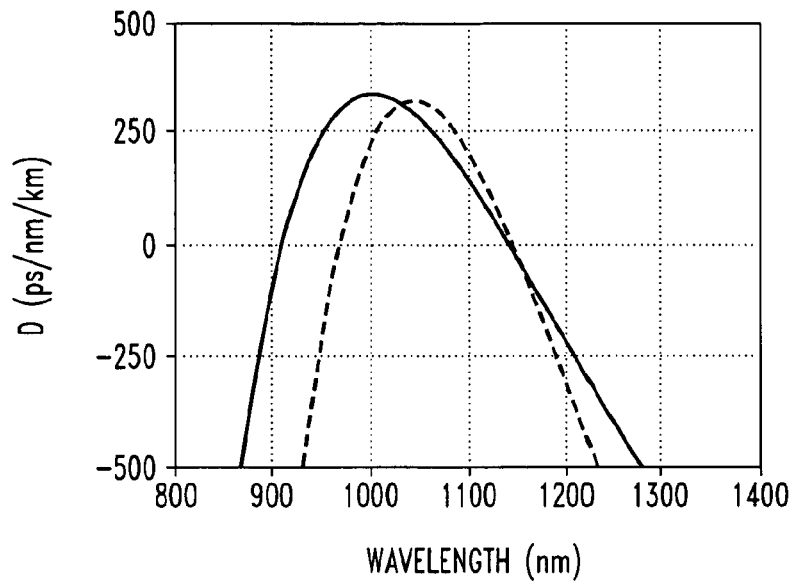
FIG. 27(a): Designed dispersion (D) vs. wavelength curves for converting 1.03 μm to 1.27 μm via Cherenkov radiation for high pulse energy (input pulse energy of 22.4 nJ)
Figure 27B:
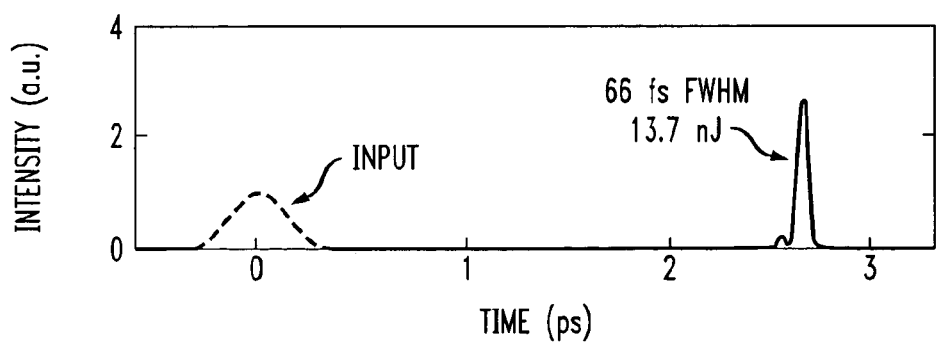
FIG. 27(b): Output intensity (top) and spectrum (bottom) after propagating through a 3-cm HOM fiber at an input energy of 22.4 nJ. For comparison, the input spectrum (scaled down by a factor of 5) and pulse (dashed line) are also shown. The output pulse width and energy are also indicated.
Figure 27C:
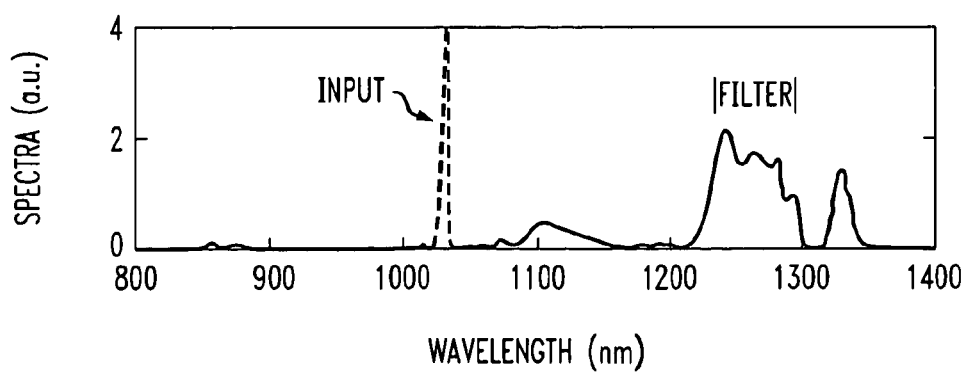

To achieve greater than 10 nJ pulse energy, the magnitude of $D*A_{eff}$ must be increased by ~5 times. FIG. 27(b) shows the numerical simulation results of Cherenkov radiation with the dispersion curves shown in FIG. 27(a). Greater than 13 nJ of Cherenkov radiation can be produced-in a HOM fiber as short as 3 cm. Both dispersion curves (solid and dashed lines in FIG. 27(a)) produced similar output characteristics. Thus, our design is reasonably tolerant to small amounts of deviation in the dispersion curve, which can be introduced in the fiber fabrication process.

Figure 25A:
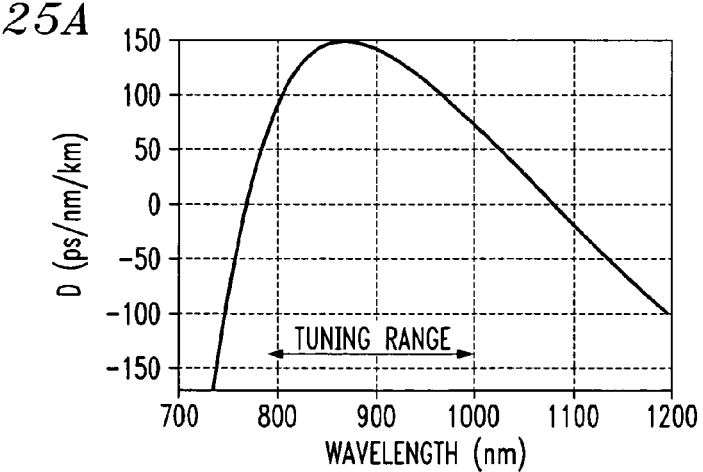
FIG. 25(a): Designed dispersion optimized for a 775-nm input.
Figure 25B:
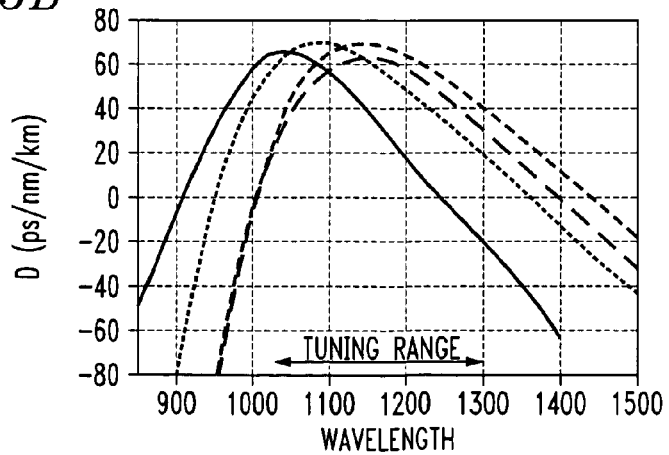
FIG. 25(b): Dispersion tuning range, illustrating a tuning range of about 50 nm for the ZDW of the HOM fiber, for a peak wavelength shift for 775-nm and 1030-nm input signals.
Figure 28A:
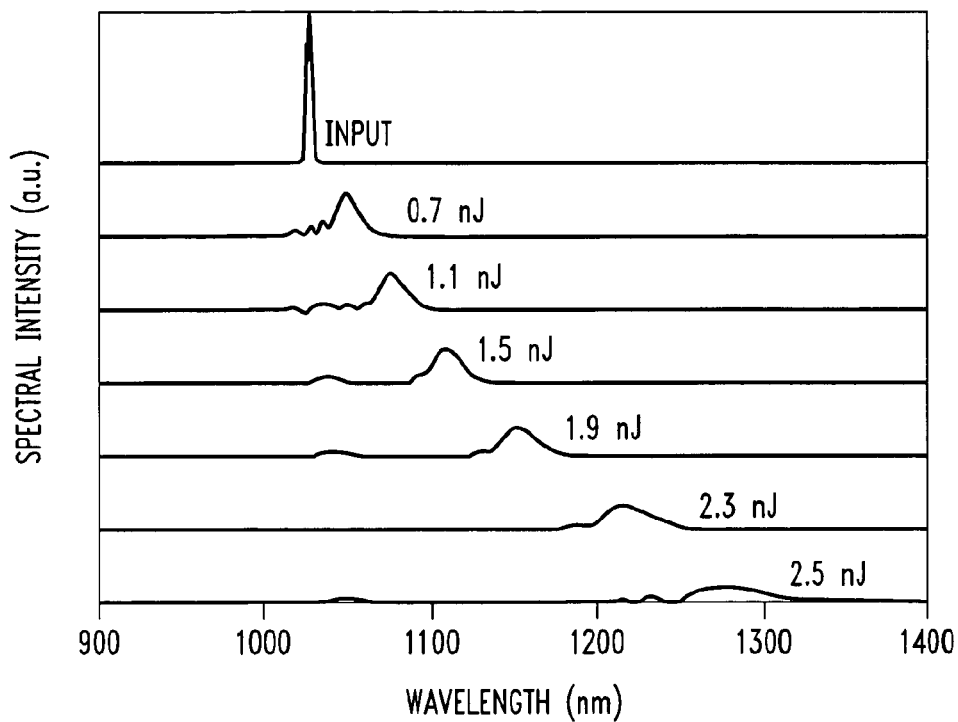
FIG. 28 shows output spectra (a) at various input pulse energies for a 1-meter HOM fiber and (b) at various propagation distance (z) in the HOM fiber (i.e., HOM fiber length) for an input pulse energy of 1.5 nJ. For comparison, the input spectrum is also shown.

FIG. 28(a) shows numerical simulation results of SSFS in such HOM fibers, by adjusting the launch power into the HOM fiber module. The conversion efficiency is ~70% for a Gaussian input pulse at 280-fs width (FWHM). Thus, even a 5-nJ pulse launched into the HOM fiber module should be sufficient to achieve the design specifications. The output pulse widths are between 50 and 70 fs throughout the tuning range. Very similar results were also obtained for the 775-nm input with the design curve shown in FIG. 25(a). We have further determined that a shift as large as ~50 nm in zero-dispersion wavelength (the dash-dotted and the dotted line in FIG. 25(b)) will not significantly impact (<8% in output pulse energy) the performance of the HOM fiber, making our design tolerant to fabrication imperfections. We note that the dispersion curves shown in FIG. 25 are of the same functional dependence as our existing HOM module except that the peak wavelength is shifted for optimum performance at 775-nm and 1030-nm input. Preliminary design simulations indicated that such dispersion characteristics are achievable. In fact, dispersion characteristics better than those shown in FIG. 25 can be readily obtained. We emphasize that these preliminary design studies are based on highly reliable in-house design tools developed at OFS, and have taken into account practical considerations such as the manufacturability and yield of the fiber. Thus, these designs are immediately viable commercially.

Figure 28B:
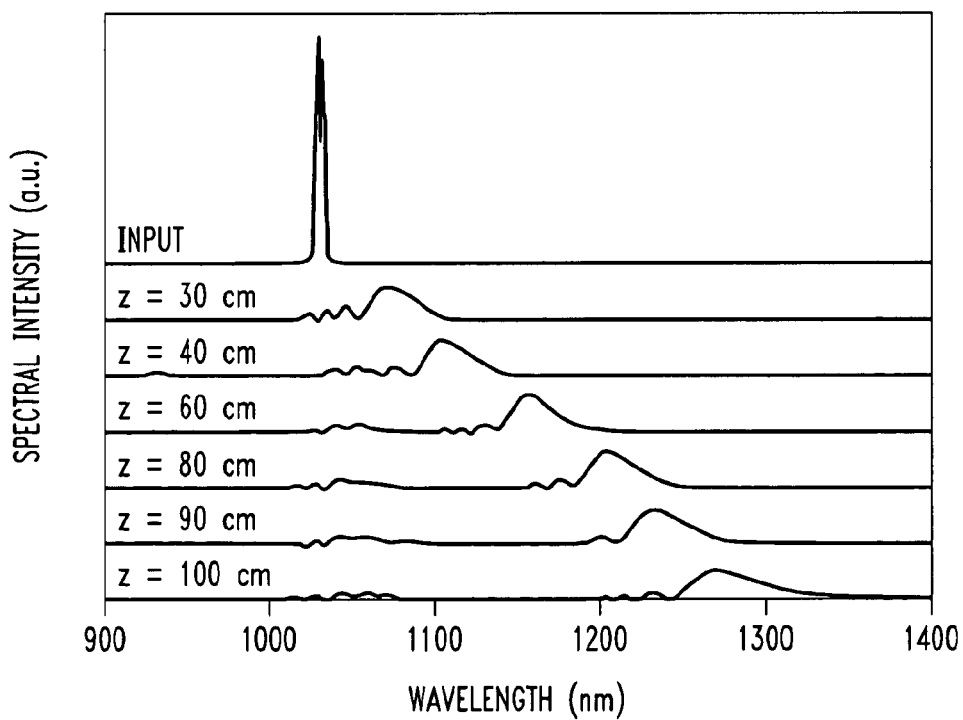

In addition to the power tuning of the output wavelength, an alternative method for wavelength tuning is simply using different fiber length. FIG. 28(b) shows the simulated output spectrum at various HOM fiber lengths while maintaining the input power. Tuning range identical to using power adjustment, with a conversion efficiency of ~70% can be easily achieved.

Perhaps the most promising and successful area in biomedical imaging that showcases the unique advantage of multiphoton excitation is imaging deep into scattering tissues. One of the promising approaches for imaging deep into scattering biological tissue is using longer excitation wavelength. It is well known that the scattering mean free path is proportional to the fourth power of the excitation wavelength in the Rayleigh region, where the size of the scatterer (a) is much smaller than the wavelength, i.e., $2\pi/\lambda < 0.1$. When the size of the scatterer becomes comparable to the wavelength, i.e., in the Mie scattering region, the scattering mean free path (MFP) has a weaker dependence on the wavelength. Although there is little data for tissue scattering beyond 1.1 μm, the available data at shorter wavelengths clearly indicates the general trend that the scattering MFP increases as one uses longer excitation wavelength. In fact, the "diagnostic and therapeutic window," which is in between the absorption regions of the intrinsic molecules and water, extends all the way to ~1280 nm (see FIG. 8 for the water absorption spectrum), significantly beyond the current investigations of the near IR spectral window of 700 to 1000 nm. We believe such a constrained is mostly caused by the lack of a convenient excitation source.

Figure 29:
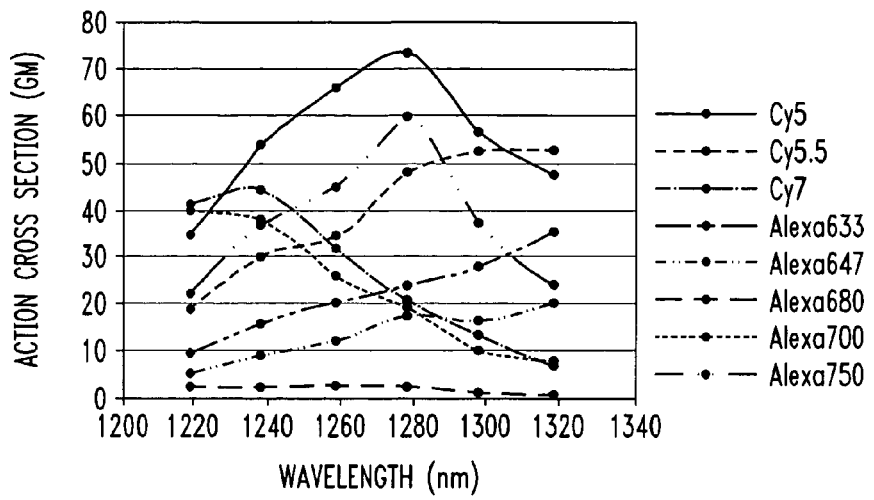
FIG. 29 shows two-photon excitation spectra of fluorophores. Data represent two-photon action cross-section, i.e., the product of the fluorescence emission quantum efficiencies and the two-photon absorption cross sections. 1 GM≡$10^{-50}$ cm$^4$ s/photon, where the spectra are excited with linearly polarized light using a Ti:S pumped OPO.
Figure 30A:
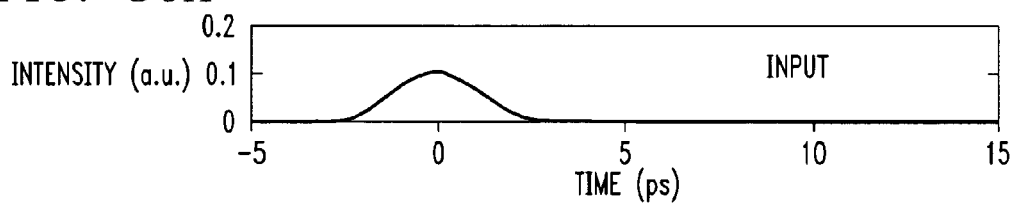
FIG. 30 is a temporal pulse evolution in an HOM fiber module at various propagation distance (z) with a 2.6-nJ chirped input pulse. Insert in (d) is the zoom-in version of the soliton pulse, and the FWHM of the soliton is 44 fs.
Figure 30B:
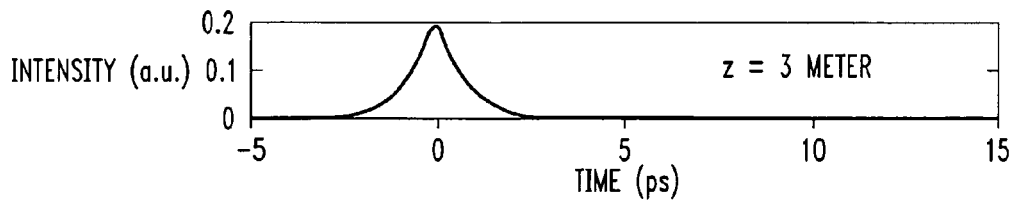
Figure 30C:
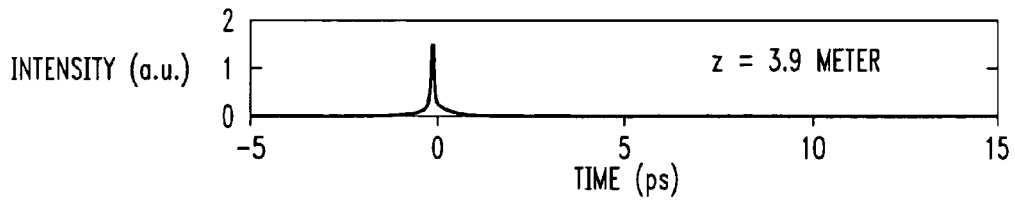
Figure 30D:
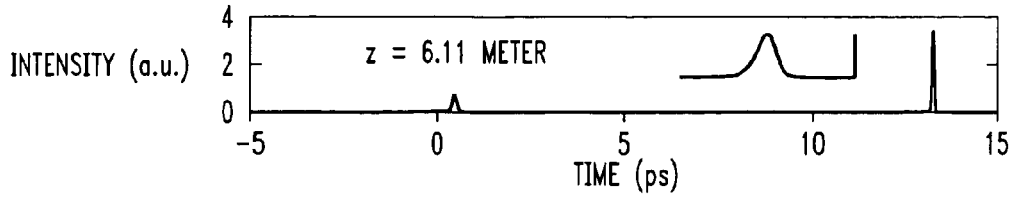

There are a few experimental demonstrations of imaging at longer wavelengths by several groups. We have also carried out detailed studies of multiphoton excitation of fluorophores within the spectral windows of 1150 to 1300 nm, and have found useful multiphoton cross sections (10 to 100 GM, comparable to fluorescein at shorter wavelength) exist for a number of long wavelength dyes (FIG. 29). Clearly, longer wavelength imaging is feasible. In addition for the reduction of scattering of the excitation light, there are a number of additional advantages at the longer excitation window. It was shown previously that longer wavelength imaging is less damaging to living tissues. The use of longer excitation wavelengths will typically result in longer wavelength fluorescence emissions and second or third harmonic generations. Because of the scattering and absorption properties of tissues, a long wavelength photon stands a much better chance of being detected by the detector. Thus, the long wavelength window for multiphoton imaging should also improve the signal collection, another critical issue in imaging scattering samples. There is no doubt that the creation of an all-fiber, wavelength tunable, energetic femtosecond source at the longer wavelength window of 1030 to 1280 nm will open significant new opportunities for biomedical imaging.

Our overall approach to wavelength-tunable sources is to develop fiber sources of 10- to 25-nJ and ~300-fs pulses, which will propagate in HOM fiber modules as Raman solitons to produce the desired outputs. Starting with pulses at 775 nm (1030 nm), pulses tunable from 775 to 1000 (1030 to 1280 nm) will be generated. The source development that we propose is enabled by the coincident advances in short-pulse fiber lasers and propagation of higher-order modes, along with the commercial development of semiconductor structures for stabilizing short-pulse lasers (to be described below). The availability of excellent fibers and continued improvement in the performance and cost of high-power laser diodes provide the technical infrastructure needed to support the development of short-pulse fiber devices.

We will develop single wavelength all-fiber femtosecond sources at 1030 nm and 775 nm with pulse energies at 10 and 25 nJ at repetition rates of 40 to 100 MHz.

Our first step is to modify and optimize commercially available femtosecond fiber sources to achieve ~10-nJ pulses, which will be sufficient to achieve our first goal of 1- to 2-nJ output pulses. Although we are fully capable of building such sources ourselves, we aim to jump start the program by fully leveraging existing commercial technologies. The main task during this stage is to make the commercial sources truly all-fiber. We realized that one of the main drawbacks of existing commercial fiber sources is that they are not all-fiber. For example, the PolarOnyx system (FIG. 10(c)) requires a separate rating compressor box (not shown in the photograph) to de-chirp the output pulse at 14-nJ output. As we have discussed, free-space components such as the grating compressor not only negate many advantages of the fiber source, they also make the fiber source ironically incompatible with fiber delivery.

Energetic femtosecond fiber sources (either from an oscillator or a CPA system) have typically chirped output to avoid optical nonlinearity, and therefore, external dispersion compensation is required to recover the femtosecond pulses. The main reason for the required free-space grating compressor in the current fiber source is the lack of low nonlinearity anomalous dispersion fiber, i.e., fibers with large $A_{eff}$ and large positive D value. Although airguided BGF can be used for dispersion compensation, there were a number of practical issues such as termination, fusion splice, birefringence, loss, etc. On the other hand, the proposed HOM fiber can easily perform dispersion compensation in addition to SSFS, by simply adding HOM fiber length in the HOM fiber module. For example, with a typical chirp of 0.24 ps²/nm from a fiber source (the amount of chirp caused by ~12 m of SMF at 1030 nm), our simulation shows that a HOM fiber length of ~6 m will produce the output nearly identical to that shown in FIG. 28. FIG. 30 shows the pulse evolution through 1 meter of standard SMF pigtail and approximately 6 meter of HOM fiber starting with a typical output chirp of 0.24 ps²/nm. Intuitively, the first ~3 meters of the HOM fiber, and the last meter or so of HOM fiber does the SSFS. Because the transmission loss of the HOM fiber is extremely low (similar to conventional SMF where light loses half of its power over a length of 10 miles), HOM fiber length of tens of meters will incur essentially zero loss. In fact, as we will explain later in greater detail, the longer fiber length not only compensates pulse chirp from the fiber source, making the source all-fiber, it would simultaneously offer a tremendous practical advantage in a clinical environment.

Figure 31A:
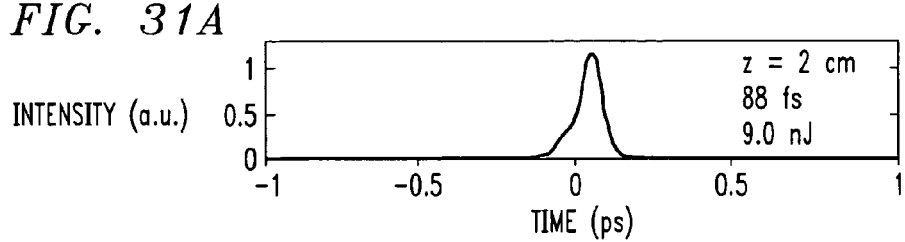
FIG. 31: Output intensity at various propagation distance (z) at an input pulse energy of 22.4 nJ, where no post dispersion compensation is employed. The pulse width (FWHM) and energy are also indicated.
Figure 31B:
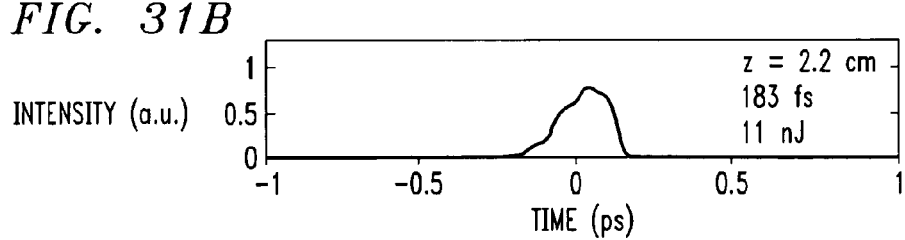
Figure 31C:
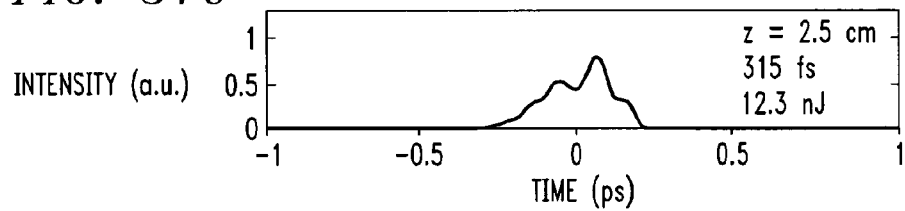

FIG. 31 shows the pulse width and energy directly from the HOM fiber at three propagation distances. Approximately 10 nJ pulses can be obtained at 100 to 200 fs pulse width without any dispersion compensation if we reduce the HOM fiber length to 2.2 cm. Although the pulse quality and energy is somewhat reduced (FIG. 31) when compared to that shown in FIG. 27(b), the elimination of dispersion compensation is highly convenient and offers the opportunity for direct fiber delivery of such an energetic pulse. We will pursue this exciting opportunity in addition to our conventional approach of post dispersion compensation.

The second step, which involves our own laser and source development, aims to improve the pulse energy to ~25 nJ in an all fiber design. Such pulse energies are necessary for achieving a final tunable output of 5- to 10-nJ pulses. There are two approaches to achieve our aim.

The first approach closely follows the strategy of the existing commercial devices using CPA. In a realistic fiber amplifier capable of the needed performance, a pulse is taken from an oscillator by splicing on an output fiber (tens of meters in length) where the pulse is highly stretched temporally. The stretched pulse is then amplified to high pulse energy by a fiber amplifier. Nonlinear effects that could distort the pulse are avoided because the pulse is stretched, which reduces the peak power. The output from the amplifier will be an amplified version of the same chirped pulse. The pulse is contained in ordinary single-mode fiber throughout the device. The above described CPA scheme has enabled significantly improved pulse energy in fiber amplifiers. Even µJ pulse energies can be obtained (although at much lower repetition rate). For our proposed sources, we will amplify pulses to 25 nJ at 1030. We aim to amplify to 50 nJ at 1550 nm in order to obtain ~25-nJ pulses at 775 nm. Commercial fiber amplifier modules already exist to delivery the necessary power for our applications. In addition, methods for overcoming fiber nonlinearity in a fiber CPA system have been demonstrated. Thus, we do not anticipate any difficulty in achieving these design goals.

The combination of a laser and an amplifier in our first approach allows both to be designed easily, and is certain to meet or exceed our design specifications. Indeed, it is highly likely that commercial femtosecond fiber sources based on the CPA technique can deliver the necessary pulse energy (25 to 50 nJ) and power (1 to 2 watts) within the grant period. Thus, there is a possibility that we can continue leveraging commercial femtosecond fiber sources. On the other hand, the addition of an amplifier adds costs and complexity to the source (at least one more pump laser and driver will be required), and always adds noise to the output. Ultimately, it will be desirable to reach the needed pulse energies directly from oscillators. Thus, as an alternative and lower cost approach, we will pursue the development of high-energy oscillators in parallel with the construction of low-energy oscillators that are amplified to the required energies.

The essential physical processes in a femtosecond laser are nonlinear phase accumulation, group-velocity dispersion, and amplitude modulation produced by a saturable absorber. A real or effective saturable absorber preferentially transmits higher power, so it promotes the formation of a pulse from noise, and sharpens the pulse. Once the pulse reaches the picosecond range, group-velocity dispersion and nonlinearity determine the pulse shape. In the steady state, the saturable absorber thus plays a lesser role, stabilizing the pulse formed by dispersion and nonlinearity. It is known that the pulse energy is always limited by excessive nonlinearity. This limitation is manifested in one or two ways:

(1) A high-energy pulse accumulates a nonlinear phase shift that causes the pulse to break into two (or more) pulses. This is referred to as "wave-breaking."

(2) To date, the best saturable absorber for fiber lasers is nonlinear polarization evolution (NPE), which produces fast and strong amplitude modulation based on polarization rotation. It was employed in the Yb fiber lasers described in our preliminary results. A disadvantage of NPE is that the transmittance is roughly a sinusoidal function of pulse energy; the transmittance reaches a maximum and then decreases with increasing energy. Once the NPE process is driven beyond that maximum transmittance, pulses are suppressed because lower powers experience lower loss and are thus favored in the laser. This situation is referred to as "over-driving" the NPE.

Figure 32:
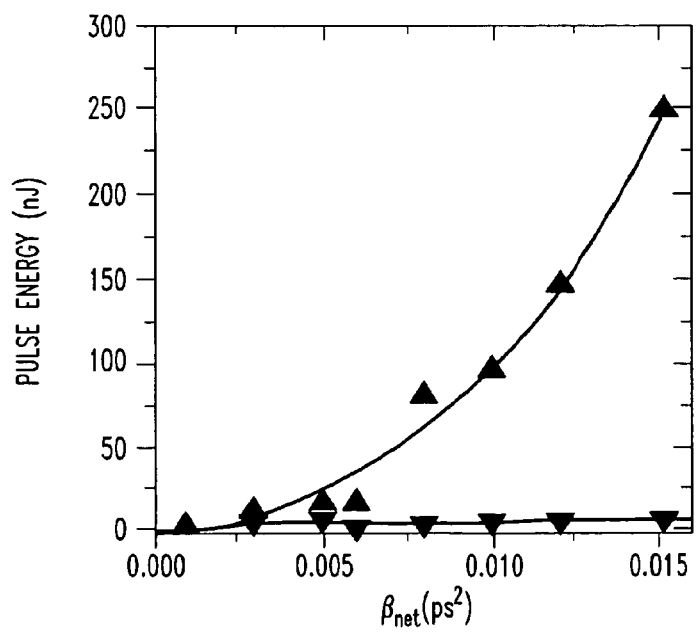
FIG. 32 shows energy of self-similar pulses (up-triangles) obtained in numerical simulations of fiber laser, plotted versus net cavity dispersion. The down-triangles are the energies produced by stretched-pulse operation of the laser.

Thus, eliminating "wavebreaking" and "over-driving" are essential in order to achieve high pulse energy from a fiber laser. We have shown that the first limitation, which is the more fundamental of the two, can be avoided using self-similar pulse evolution. We have calculated the energy of stable self-similar pulses and the result is plotted in FIG. 32 as a function of net cavity dispersion. In principle, 250-nJ pulse energies are possible, if the second limitation permits it. Thus, a promising approach is to create new saturable absorbers where "over-driving" cannot occur. In essence, we need a saturable absorber of which the transmittance is not a sinusoidal function of pulse energy. Surveying the landscape of saturable absorbers used in femtosecond lasers, the real saturable absorption in a semiconductor is ideally suited for this purpose.

Semiconductor saturable absorbers (SSA's) are based on saturation of an optical transition, and in contrast to NPE (which is based on interference) they cannot be overdriven. Therefore, it should be possible to obtain much higher pulse energies in fiber lasers if NPE is replaced by a SSA. Historically, this was not feasible, because semiconductor structures capable of producing the large modulation depth (>10%) needed in a fiber laser did not exist. In addition, a practical impediment in the past was the lack of a commercial source of such structures—painstaking research was required to develop new ones. However, significant progress in the modulation depth has been made in the last several years and there is now a commercial company that sells SSA's. BATOP GmbH (Weimar, Germany) has emerged as a reliable source of SSA's, with a variety of designs at reasonable prices (<$1K/piece). In particular, structures with 80% modulation depth are available as standard designs. It will be reasonably straightforward to incorporate these structures in out lasers in place of NPE. The main work will be optimizing the design of the structure for the target performance levels.

A second major advantage of SSA's is that they are compatible with integrated designs. The development of saturable absorbers that provide fast and deep modulation will significantly facilitate the design of all-fiber and environmentally-stable lasers. In principle, a femtosecond laser could be constructed of segments of polarization-maintaining fiber that provide gain and anomalous dispersion, and the saturable absorber. Fiber-pigtailed versions of SSA's are already commercially available. Such a laser would be as simple as possible, with no adjustments other than the pump power. We will design, construct and characterize high-power fiber lasers based on SSA's. Although the incorporation of SSA with large modulation depth in a mode-locked fiber laser is relatively new and there may be a number of practical issues to be addressed in this work, the fundamental basis of the approach is established theoretically, and initial experiments in our lab with structures from BATOP confirm that they perform as advertised. The promise of 25- to 50-nJ pulses directly from a robust and cost effective fiber oscillator is highly significant. Thus, we will include this development effort as a more exploratory component of this research program, complementing our reliable (may even commercially available), but inherently more expensive, approach of a fiber CPA system.

Figure 33:
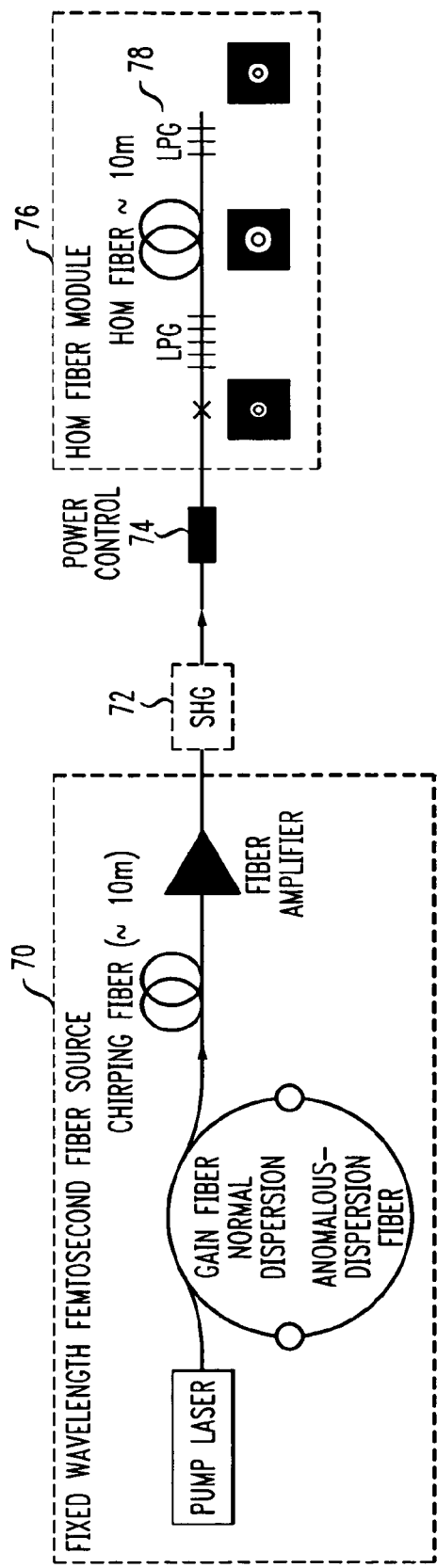
FIG. 33 is a schematic drawing of the proposed all fiber, wavelength tunable, energetic, femtosecond source after full system integration.

We aim to demonstrate two all-fiber femtosecond sources with wavelength tuning ranges of (1) 775 nm to 1000 nm and (2) 1030 nm to 1280 nm. The output pulse energies will be first at 1 to 2 and then at 5 to 10 nJ. We will combine the femtosecond sources and the HOM fiber modules developed in Aims 1 and 2 into an all-fiber system. The fully integrated source is schematically shown in FIG. 33. The dashed boxes indicate the components developed in Aims 1 and 2. A CPA approach for fixed wavelength fiber source is shown. SHG is needed only for the 775-nm input. The fiber lengths of the chirping fiber and the HOM fiber are approximate. The dark dots indicate locations for fiber splicing. The cross (x) indicates location for fiber splicing in power tuning, or connectorization in length or sequential tuning of multiple HOM fiber modules. The mode profiles of the fundamental and $LP_{02}$ modes are also shown.

The intrinsic chirp from the fiber source 80 (either a mode-locked fiber lasers or a CPA system), which was a major limitation in previous fiber systems, provides several key advantages for our system. First, it allows ~10 m in the total length of the output fiber. Second, the highly chirped pulse (chirp of at least 5.25 fs/nm) makes the length of the single mode fiber pigtail 82 inconsequential, eliminating the practical difficulties in cleaving and splicing. Finally, the longer single mode fiber pigtail 82 can also accommodate additional fiber devices such as a variable fiber attenuator and/or a fiber optic switch.

A second harmonic generator 84 (SHG) will be employed to generate femtosecond pulses at 775 nm. It was previously known that SHG with a linearly chirped fundamental pulse will result in a linearly chirped SH pulse, which can be subsequently compressed using linear dispersion. Interestingly, the final chirp-free SH pulse width is independent of whether the compression is carried out before or after the SHG 84. The conversion efficiency, however, is obviously higher if the chirped fundamental pulse is compressed before SHG. Because the designed pulse energy at the fundamental wavelength is high (at 10 to 50 nJ/pulse), the conversion efficiency for SHG with the proposed excitation source will be limited mostly by the depletion of the fundamental power, not by the available pulse peak intensity. Thus, SHG will be highly efficient event with a chirped fundamental pulse with durations on the order of several picoseconds if efficient doubling crystals are employed. For example, with a periodically poled $LiNbO_3$ (PPLN). Single-pass conversion efficiencies (energy efficiency) as much as 83% and 99% are demonstrated for bulk and waveguide PPLN devices, respectively. Thus, SHG 84 with a chirped fundamental pulse can be used with the proposed femtosecond pulse source 80 without the reduction in conversion efficiency, and, as discussed in the previous paragraph, has significant advantage in the subsequent fiber optic delivery process. In addition, chirped SHG also eliminates the possibility of damaging to the doubling crystal due to the high peak power of a femtosecond pulse. Photorefractive effects of the PPLN device is a concern at high average power (>500 mW), but such effects typically only occur at wavelength below 700 nm, and can be mitigated to a large extent by increasing the temperature of the crystal and/or by doping the crystal with magnesium. To be conservative, we are targeting a power conversion efficiency of ~50% on a routine basis.

We will design systems using two different tuning mechanisms 86: 1. power tuning, and 2. length tuning. As shown in the preliminary results, both tuning mechanisms offer similar tuning range (FIG. 28). The power tuning requires only one HOM fiber module 88 for the entire spectral range, however, the output power varies by approximately a factor of 3 (power input multiplied by the conversion efficiency). Although this power variation across the tuning range is comparable to current femtosecond systems like the Ti:S or Ti:S pumped OPO, it may nonetheless limit the practical utility of the system, particularly at the smaller wavelength shift where the output power is lowest. Another approach is fiber length tuning, which can essentially maintain the output power (FIG. 28(b), within +/−5%) across the entire spectral range. Fiber length tuning, however, requires multiple HOM fiber modules 88, increasing the system cost. An obvious compromise is to combine the two tuning mechanisms 86. As an alternative to the power tuning, we will design 2 to 3 HOM fiber modules 88 of different length, each optimized for power tuning over a ~100-nm spectral range to maintain a reasonably constant output. Such a segmented tuning also simplifies the design of the output LPGs 89 since a much narrower range of output wavelengths needs to be converted. It is interesting to note that such segmented tuning is similar to the early generations of Ti:S lasers where multiple mirror sets were required to cover the entire tuning range. However, unlike a mirror-set exchange in a Ti:S laser, which would take an experienced operator several hours to perform, the exchange of the HOM fiber modules 88 would take only a few seconds through a single mode fiber connector (see the connectorized output from a fiber source in FIG. 10), and require neither experience nor knowledge of the system. For a completely electronically controlled system, a simple fiber optic switch can be used to provide push-button HOM fiber module exchange. In fact, such a tunable HOM fiber module has already been experimentally demonstrated several years ago for telecom applications. We also note that, as a simple extension to the fiber length tuning, a HOM fiber module can also be designed to provide output at the input wavelength without SSFS. In such cases, the HOM fiber module simply serves as a delivery fiber for chirp compression and pulse delivery.

The fiber-length tuning described above is obviously similar to the sequential tuning described above to achieve high pulse energy. Both require multiple HOM fiber modules. In length tuning, however, the same HOM fiber of different lengths are used; while in sequential tuning, two or more different HOM fibers are required.

Both power tuning and segmented length tuning require a mechanism to control the incident power. SSFS is a nonlinear optical effect and effectively happens instantaneously (<1 ps). Thus, the rate of the wavelength tuning of the proposed fiber source can be ultrafast, and is completely determined by the rate of power change. There are two approaches to adjust the power into the HOM fiber module. Mechanical in-line fiber attenuators can achieve a tuning speed of ~10 Hz, several orders of magnitude faster than any existing laser systems. Because only a small range of power adjustment is necessary for achieving the entire range of wavelength tuning (less than a factor of 4 for power tuning), variable fiber attenuators that based on microbending can easily provide the speed and modulation depth required. Such a variable attenuator can be calibrated so that rapid, electronically controlled wavelength tuning can be achieved. We note that compact, electronically controlled variable fiber attenuators are widely available commercially. Most commercial attenuators can provide modulation depth of ~1000. Thus, we do not anticipate any difficulty implementing the power control mechanism. An alternative approach will be more expensive (~$2 k), it can easily provide nanosecond (i.e., pulse-to-pulse) wavelength switching speed. In addition, such a device also provides the capability for fast (ns) laser intensity control. To overcome the insertion loss of the electro-optic modulator, it can be placed before the fiber amplifier in a CPA system. We also note that these EOMs are routinely used in telecommunications and are highly robust (telecom certified) and compact (half the size of a candy bar). Our proposed source can be readily configured to provide this high speed tuning capability.

We will perform detailed system testing and characterization, providing feedbacks for iteration and optimization of our development efforts. In particular, we will assess the wavelength and power stability of the system. We are well aware the fact that SSFS is a nonlinear optical effect; and nonlinear optical effects are generally sensitive to fluctuations in input power, pulse width, and pulse spectrum. We have taken this stability issue into our design considerations. First, we start with an all-fiber, single wavelength femtosecond source. One of the salient features of an all-fiber design is its stability. It is well known that a fiber laser is more stable than a bulk solid state laser. Second, our fiber sources are specifically designed for biomedical imaging applications. Because of the broad output pulse spectrum (10 to 20 nm) and the broad excitation peaks of fluorescent molecules (tens of nm), a few nm of wavelength shift is generally inconsequential. This is in sharp contrast to applications such as precision frequency metrology, where even a small fraction of an Angstrom spectral shift cannot be tolerated. Finally, the soliton pulse shaping process is robust against fluctuations in the input, which is one of the main reasons that solitons were used in long haul communication systems. Our preliminary results in FIG. 24 also clearly demonstrate the robustness of SSFS. Even with a highly nonideal input pulse (FIG. 24 inset), a nearly perfect soliton pulse is obtained at the output. In addition, simulations with a perfect Gaussian pulse input showed good agreement with the experiments, particularly for the output at the soliton wavelength. Thus, we are confident about the stability of the proposed source. In the unlikely event that unacceptably large power fluctuations are present, an alternative approach is to employ feedback stabilization. Because power adjustment mechanisms are already needed for wavelength tuning, the only addition component for feedback control is a photodiode for power monitoring (for example, through a 1% fiber tap in the single mode pigtail before the LPG). Such a feedback control mechanism can largely eliminate power drifts on the slow time scale, ~10 Hz for the mechanical variable fiber attenuator and ~MHz for the electro-optical intensity modulator. We note that such a power stabilization scheme ("noise eater") has already been commercially implemented for a variety of laser systems. We do not anticipate any difficulty implementing the control mechanism if necessary.

Polarization control is another issue of practical concern. For applications that demand a linear input polarization, polarization maintaining (PM) fiber can be used throughout the system. Because the HOM fiber is fabricated within the conventional silica fiber platform, PM HOM fibers can be made using the same method designed for conventional PM fibers (such as adding stress rods to form a Panda fiber). For applications that demand adjustable input polarization, non-PM HOM fibers can be used and a simple in-line fiber polarization controller can be used to adjust the output polarization state, eliminating the conventional free-space wave plate and/or polarizer.

There are several methods to remove the residue input light at the output of the HOM fiber module. Perhaps the simplest approach is to directly deposit a dichroic coating (long wavelength pass) on the output face of the fiber. Such coatings were often done for fiber lasers with linear cavities and the deposition techniques were similar to that on a conventional glass substrate. After all, a silica fiber is a piece of glass with a small diameter.

Figure 34:
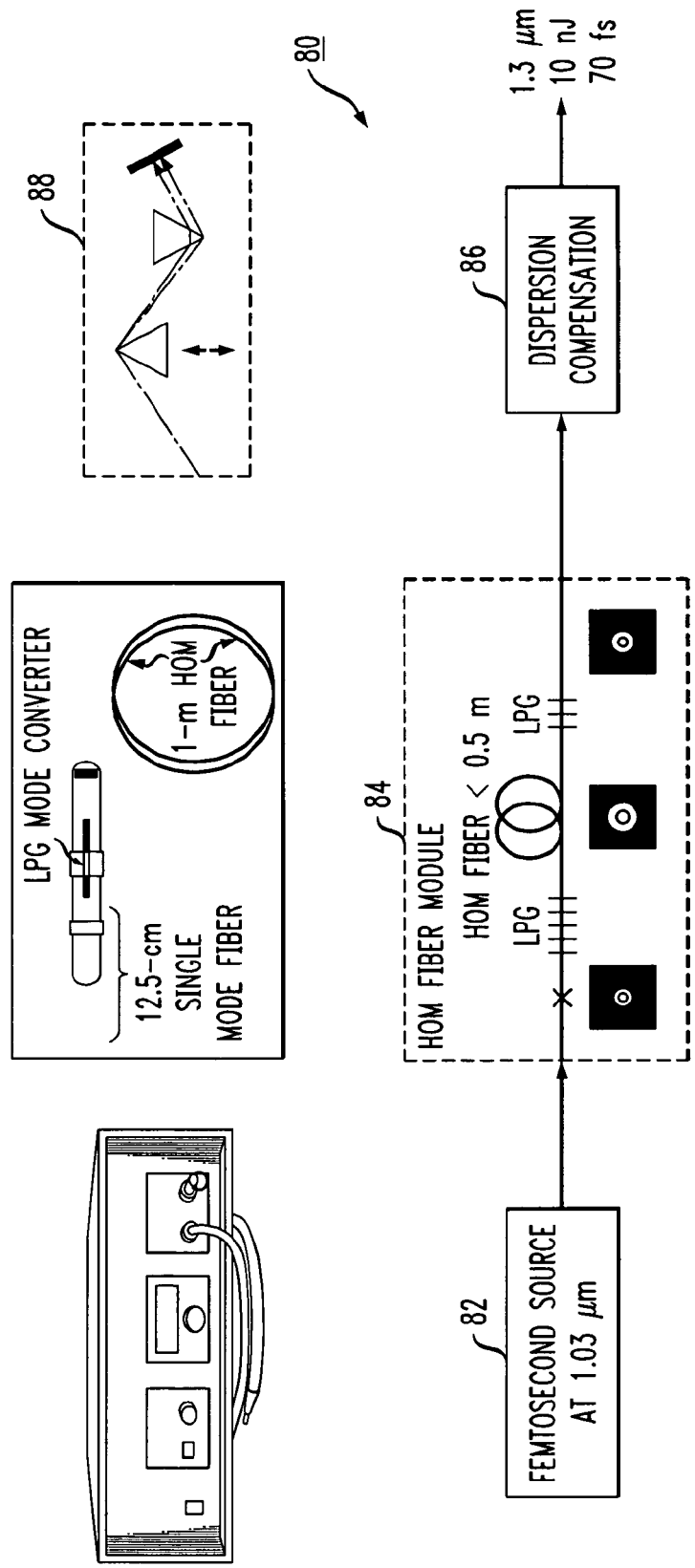
FIG. 34: Schematic drawing of the proposed energetic fiber femtosecond source after full system integration (bottom) and more detailed photographs and device setup (top). Dispersion compensation using a prism pair is shown and is optional for high energy output. The mode profiles of the fundamental and $LP_{02}$ modes are also shown.

We aim to demonstrate an energetic femtosecond fiber source at 1.3 µm. The output pulse energies will be first at 2 nJ and then at greater than 10 nJ. The fully integrated source 90 is schematically shown in FIG. 34.

We will fully leverage the existing technologies by using a commercial 1.03 µm femtosecond fiber source 92 instead of developing our own fiber laser. Such an approach will be most effective in cost, and will allow us to immediately focus on the HOM fibers and Cherenkov radiation. A number of companies, such as PolarOynx Inc (photograph of device shown in FIG. 34) and IMRS America, already provide sources that perfectly fit our applications. After propagating through the HOM fiber module 94, the output will be spectrally filtered to remove light outside the 1.24 to 1.3 µm bandwidth. Perhaps the simplest approach for optical filtering is to directly deposit a dichroic coating (long wavelength pass) on the output face of the fiber. Such coatings were often done for fiber lasers with linear cavities and the deposition techniques were similar to that on a conventional glass substrate. Dispersion compensation 96 will be used to remove the linear chirp of the Cherenkov radiation so that the shortest pulses can be obtained at the output. The amount of dispersion needed (~0.01 ps/nm) for de-chirping the Cherenkov radiation is equivalent to that of several centimeters of HOM fiber (after all, 25 cm or less HOM is used to generate the Cherenkov). Such a small amount of dispersion can be provided by a variety of methods. For example, prism pairs 98 made of pure silicon or dense glass (schematically shown in FIG. 34), which are low loss, low cost, and easy to operate, can readily provide the necessary dispersion value. As discussed in the previous section, for Cherenkov radiation above 10 nJ, we also have the option to eliminate the dispersion compensation after the HOM if a slightly longer pulse width (100 to 200 fs) is acceptable.

We will perform detailed system testing and characterization, providing feedbacks for iteration and optimization of our development efforts. In particular, we will assess the wavelength and power stability of the system. We are well aware of the fact that Cherenkov radiation is a nonlinear optical effect; and nonlinear optical effects are generally sensitive to fluctuations in input power, pulse width, and pulse spectrum. We have taken this stability issue into our design considerations. First, we start with a fiber femtosecond source. One of the salient features of a fiber source is its stability. It is well known that a fiber laser is more stable than a bull solid state laser. Second, our fiber sources are specifically designed for biomedical imaging applications. Because of the broad output pulse spectrum and the broad excitation peaks of fluorescent molecules (tens of nm), a few nm of wavelength shift is generally inconsequential. This is in sharp contrast to applications such as precision frequency metrology, where even a small fraction of an Angstrom spectral shift cannot be tolerated. Finally, the soliton pulse shaping and Cherenkov radiation is robust against fluctuations in the input, as demonstrated by both our numerical simulations and previous experiments.

Polarization control is another issue of practical concern. For applications that demand a linear input polarization, polarization maintaining (PM) fibers can be used throughout the system. Because the HOM fiber is fabricated within the conventional silica fiber platform, PM HOM fibers can be made using the same method designed for conventional PM fibers (such as adding stress rods to form a Panda fiber). For applications that demand adjustable input polarization, non-PM fibers can be used and a simple in-line fiber polarization controller can be used to adjust the output polarization state, eliminating the conventional free-space wave plate and/or polarizer.

We will demonstrate the significance of our new femtosecond sources for biomedical applications of multiphoton microscopy, spectroscopy and endoscopy. Cornell's strong biomedical nonlinear imaging research infrastructure provides an ideal proving ground for new femtosecond sources and our proposed laser development is highly synergistic with these existing research programs. Cornell is home to the Development Resource for Biophysical Imaging & Optoelectronics (DRBIO), an NIH-funded Resource, where multiphoton microscopy was originally developed. A number of multiphoton microscopes currently exist in the laboratories of both the PI and DRBIO.

The proposed longer wavelength femtosecond source offers unprecedented capability at the 1.3 µm wavelength window. Although there are only a few experimental demonstrations for multiphoton imaging beyond 1.1 μm, longer wavelength multiphoton imaging is feasible and can potentially offer significant advantage in deep tissue imaging, particularly with the high pulse energy we will be able to obtain. As a part of the NSF CAREER grant for deep tissue imaging, we have already started our effort on exploring this new spectral window for MPM, using the existing Ti:S pumped OPO at the PI's lab. We will demonstrate the capability of the proposed femtosecond source for imaging in the 1300 nm region using indicators such as shown in FIG. 29 and IR quantum dots. We will compare these results with what we currently achieve using the OPO system. We aim to achieve unprecedented imaging depth using the energetic pulses from our source. We note that these proof-of-concept experiments are not intended for answering specific biological questions. Our main objective is to compare the imaging performance of MPM with the proposed sources and with conventional femtosecond lasers. These validation experiments, carried out in a real-world biomedical imaging facility, are essential to establish the value of the proposed sources. We believe that the creation of an energetic femtosecond fiber source at the wavelength window of 1300 nm will open significant new opportunities for deep tissue imaging.

Our first stage demonstration involves "routine" multiphoton imaging and spectroscopy. We will compare the capability of the proposed tunable fiber source with our existing Ti:S lasers. We will verify the stability of the sources in imaging, especially since the two (and three) photon-dependence of excitation "amplifies" the effects of a fluctuating laser. In addition to multiphoton imaging, a potentially even more sensitive means to judge stability would be to test the laser as an excitation source in fluorescence correlation spectroscopy (FCS) experiments, where laser noise (e.g., oscillations) would be very obvious (e.g., FCS measurements on the same sample made with our Ti:S compared to ones carried out with our prototype laser). By installing our prototype laser source on one or more multiphoton systems we will test the laser in the most practical way by using it in a routine day-to-day fashion for a variety of imaging projects. Our main objective is to compare the imaging performance of MPM with the proposed sources and with conventional Ti:S lasers.

Our second stage demonstration experiments are designed to showcase the unique advantages of the proposed femtosecond sources, which have several important functional attributes for multiphoton imaging not found in the commonly used Ti:S laser. A review of the properties of the lasers being developed and their importance to multiphoton imaging include: (1) all-fiber sources with integrated fiber delivery, (2) rapid, electronically controlled wavelength tuning, and (3) energetic pulses, particularly at the longer wavelength window of 1030 to 1280 nm.

The two femtosecond sources proposed are both all-fiber sources with integrated single mode fiber-delivered (with >5 m of fiber length); that is, the output of the sources could be directly fed into a microscope scanbox, an endoscope scanning system, or through a biopsy needle for tissue spectroscopy. For multiphoton microscopy this would greatly simplify installation and maintenance of the system since alignment would be trivial; and for endoscopic imaging and spectroscopy application fiber-delivered illumination is clearly essential.

Figure 35:
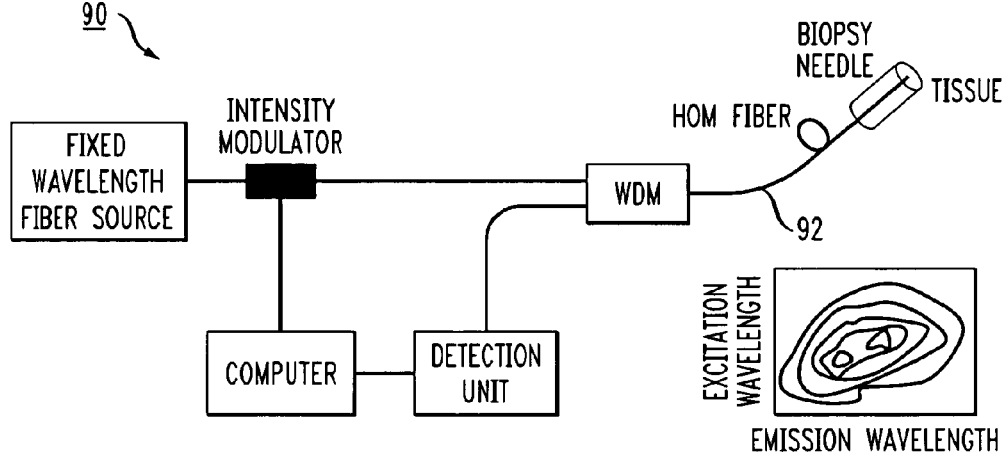
FIG. 35 shows an instrument for multiphoton spectroscopy on cancer tissues. The inset shows a schematic contour plot of the excitation-emission matrix (EEM)

A stable fiber-delivered femtosecond source in the 780-850 nm range can be directly incorporated in our current endoscope scanner design, as shown in FIG. 35. We also note that the HOM fibers are highly resistant to bending loss, a characteristic that is impossible to obtain in the large area mode fiber previously demonstrated for pulse delivery. Thus, it is particularly suited for small diameter, flexible endoscopes where bend radius as small as ~1 cm is necessary. Although no clinical experiment is planned within the scope of this program, the long fiber delivery length (~6 m) allows the source to be at a remote location away from the operating room. In a clinical environment, such a physical separation offers major practical advantages, such as eliminating the complications of sterilization, ultimately leading to a much reduced cost.

As shown in FIG. 35, HOM fiber 91 that provides the dispersion compensation and wavelength tuning through SSFS can also be simultaneously used as the delivery and collection fiber for tissue spectroscopy. The diameter of the optical fiber 91 is ~0.125 mm (standard size for single mode fiber), which is much smaller than the inside diameter of an 18 or 20 gauge needle that is routinely used for core biopsy. The excited signal will be collected by the same fiber 91. A fiber wavelength division multiplexer (WDM) 93 can be placed between the fixed wavelength femtosecond source 95 and the HOM fiber module 91 to direct the collected signal to the detecting unit 97, which consists a grating and a CCD. In addition, the rapid wavelength tuning capability allows the emission spectrum of the tissue to be recorded as a function of the excitation wavelength. These multiphoton excited fluorescence excitation-emission matrix (EEM) can potentially provide unique diagnostic signatures for cancer detection just as one-photon EEM does. The long delivery fiber (HOM fiber) once again allows the excitation and detection apparatus to be at locations away from the operating room. We further note that a double-clad fiber structure with the HOM fiber as the guiding core can easily fabricated to improve signal collection efficiency because of the all-silica fiber design.

One potential complication of the proposed tunable source for multiphoton EEM is the power and pulse width variation across the entire tuning range. Calibration using a known multiphoton excitation standard, such as fluorscein dye, will be carried out before experimentation on biological samples. Such a calibration procedure is routinely used in previous multiphoton spectroscopy work. Multiphoton excitation standards have been established in the past and has extensive experience in multiphoton spectroscopy. We don't expect significant problems in the calibration of the instrument.

Application of MPM in early cancer detection using a transgenic mouse line in which tumor formation is initiated by the conditional activation of the p53 and Rb1 genes by Adenovirus-Cre-mediated recombination has been reported. The experiment on endoscopes and tissue spectroscopy through needle biopsies is highly synergistic with the on-going cancer research and provides an ideal platform for showcasing the "all-fiber" characteristics of the proposed femtosecond source.

A unique capability of the proposed sources is the ability to rapidly tune the wavelength much faster than currently possible with single box Ti:S systems. Rapid wavelength tuning would allow for line by line switching between excitation wavelengths during scanning, or for collecting excitation spectra, a potentially important parameter for biomedical applications that may utilize intrinsic fluorophores with overlapping emissions, but different excitation spectra.

Figure 36A:
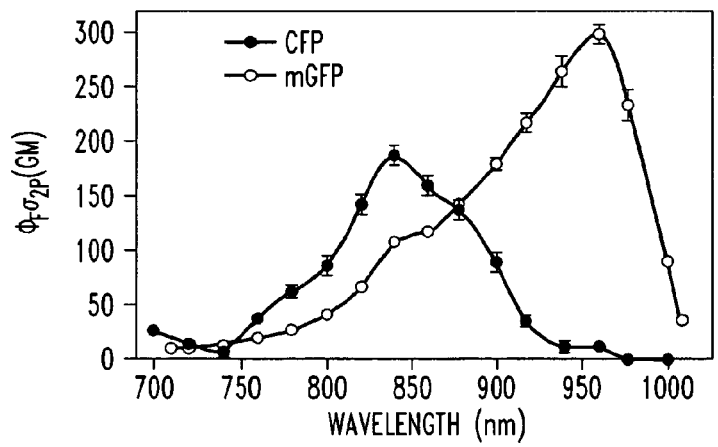
FIG. 36 shows a two-photon excitation spectra (a) and emission spectra (b) of CFP and monomeric eGFP, two common genetically encodable fluorescent proteins. A system capable of switching the excitation wavelength of ms timescales (i.e., between forward and return scan lines) would be able to more cleanly separate the emissions.
Figure 36B:
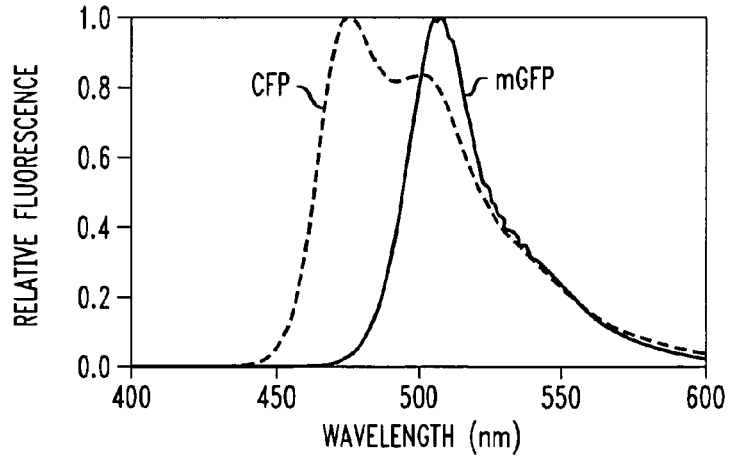

By synchronizing the wavelength control with the scanning and acquisition, we will modify one of our imaging systems to enable one wavelength during the "forward" line and a second during the return (without changing the Y position). This is analogous to what is now standard on modern AOM-equipped confocal microscopes, where, for example, a green dye is excited with 488 nm excitation in one direction and 547 nm excitation to excite a different dye during the return. In this way a two-color image can be collected using dyes with different excitation maximums and separable emissions. The temporal aspect eliminates problems with spectral cross-talk in many cases. Although multiphoton cross-sections for many dyes are broad often allowing for excitation of different dyes at the same wavelength (usually due to overlapping UV bands, so this normally only works at 800 nm or shorter), the ability to rapidly switch between wavelengths anywhere between 780 and 1000 nm would be an important enhancement for many dye pairs. After interfacing the wavelength control with our scanning systems we will apply this capability in pilot experiments with fluorophores such as CFP and GFP which have different two photon excitation maxima, but partially overlapping emission spectra (FIG. 36).

As an added benefit, the EOM device that enables rapid wavelength tuning can also be used to provide fast switching and modulation of the excitation beam. At a minimum this functionality should be comparable to what we currently achieve using our 80-nm resonance-dampened KTP*Pockel cells for routing beam blanking and intensity control (microsecond switching). Available fiber-coupled EOMs can switch in the sub-nanosecond range and should allow for a laser with a built-in modulator that would enable the user to reduce the effective laser repetition rate for measurements of fluorescent decay times and fluorescent lifetime imaging (FLIM), as well as for the more standard modulation needs. After implementing the required control electronics, we will use this functionality for routine beam blanking and control, photobleaching recovery measurements, and FLIM.

Another intriguing possibility provided by SSFS is that multiple wavelength tunable pulses can be obtained from the same fixed wavelength fiber source. For example, the output of the fixed wavelength femtosecond fiber source can be split into two halves and each half propagates through a HOM fiber module. The two HOM fiber modules can be the same (use power tuning) or of different lengths (length tuning). Such a multi-color femtosecond source opens a range of new opportunities, such as two-color photon excitation and coherent anti-Stokes Raman scattering (CARS) imaging, where two synchronized ultrafast sources are needed previously. The spectral bandwidths directly from the proposed sources will likely be too large for CARS, possibly requiring spectral filtering or shaping.

The proposed longer wavelength femtosecond source offers unprecedented capability at the wavelength window of 1030 to 1280 nm. Although there are only a few experimental works for multiphoton imaging beyond 1100 nm, longer wavelength multiphoton imaging is feasible and can potentially offer significant advantage in deep tissue imaging, particularly with the high pulse energy we will be able to obtain. Efforts are underway on exploring this new spectral window for MPM, using the existing Ti:S pumped OPO. We will demonstrate the capability of the proposed femtosecond source for imaging in the 1.27 μm region using indicators such as shown in FIG. 29 and IR quantum dots. We will compare these results with what we currently achieve using the OPO system. We aim to achieve unprecedented imaging depth using the energetic pulses from our source. There is no doubt that the creation of an all-fiber, wavelength tunable, energetic femtosecond source at the longer wavelength window of 1030 to 1280 nm will open significant new opportunities for biomedical imaging.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. An apparatus for providing optical output pulses at a desired output wavelength of less than 1300 nm from an input optical signal operating at a first, shorter wavelength, the apparatus comprising:
   an input mode converter for receiving the input optical signal exhibiting a linear chirp of at least 5.25 fs/nm and converting a spatial mode of the input signal into a higher-order-mode (HOM) optical signal; and
   a section of higher-order-mode (HOM) fiber, coupled to an output of the input mode converter, for receiving the higher-order-mode optical signal and thereafter producing as an output a higher-order-mode optical signal at the desired output wavelength, wherein the section of HOM fiber is configured to exhibit a positive dispersion and large effective area sufficient to support the propagation of the higher-order-mode optical signal therealong and induce soliton self-frequency shifting (SSFS) to produce optical output pulses at the desired output wavelength, the positive dispersion also sufficient to perform dispersion compensation on the linear chirp of the input signal so as to reduce the presence of chirp in the optical output signal.

2. The apparatus according to claim 1, wherein the dispersion and effective area of the section of HOM fiber are sufficient to produce an output pulse having an energy of not less than 20 pJ.

3. The apparatus according to claim 1, wherein the dispersion and effective area of the section of HOM fiber are sufficient to produce an output pulse having an energy greater than 1 nJ.

4. The apparatus according to claim 1, wherein the dispersion and effective area of the section of HOM fiber are sufficient to produce an output pulse having an energy greater than 5 nJ.

5. The apparatus according to claim 1, wherein the dispersion and effective area of the section of HOM fiber are sufficient to produce an output pulse having an energy greater than 10 nJ.

6. The apparatus according to claim 1, wherein the dispersion and effective area of the section of HOM fiber are further configured to generate the optical output pulses at a second output wavelength by Cherenkov radiation.

7. The apparatus according to claim 6, wherein the dispersion and effective area of the section of HOM fiber are sufficient to produce an output pulse having an energy not greater than 20 pJ.

8. The apparatus according to claim 6, wherein the dispersion and effective area of the section of HOM fiber are sufficient to produce an output pulse having an energy greater than 1 nJ.

9. The apparatus according to claim 6, wherein the dispersion and effective area of the section of HOM fiber are sufficient to produce an output pulse having an energy greater than 5 nJ.

10. The apparatus according to claim 6, wherein the dispersion and effective area of the section of HOM fiber are sufficient to produce an output pulse having an energy greater than 10 nJ.

11. The apparatus according to claim 1, wherein the section of HOM fiber is a section of solid silica-based fiber.

12. The apparatus according to claim 1, where the input mode converter comprises a long period grating.

13. The apparatus of claim 1 further comprising:
a femtosecond pulse source for generating input optical pulses at the first, shorter wavelength; and
a single mode fiber coupled between the femtosecond pulse source and the input mode converter, a combination of the single mode fiber and the input mode converter creating a linear chirp in the input optical signal of at least 5.25 fs/nm.

14. The apparatus according to claim 1 further comprising:
a second mode converter terminally connected to the output of the section of HOM fiber.

15. The apparatus according to claim 14, wherein the second converter is a long period grating (LPG).

16. The apparatus according to claim 13, wherein the optical pulse source generates input optical pulses having a pulse energy of at least 1.0 nanojoules (nJ).

17. The apparatus according to claim 13, wherein the optical pulse source generates input optical pulses having a pulse energy of at between 1.0 nJ and about 100 nJ.

18. The apparatus as defined in claim 13, wherein the optical pulse source comprises either a mode-locked laser or a chirped pulse amplification (CPA) system.

19. The apparatus according to claim 18, wherein the mode-locked laser is a mode-locked fiber laser.

20. The apparatus according to claim 18, wherein the CPA system is a fiber CPA system.

21. The apparatus according to claim 13, wherein the optical pulse source generates input optical pulses such that the first wavelength is a wavelength within a transparent region of a silica-based fiber.

22. The apparatus according to claim 21, wherein the input wavelength is below 1300 nanometers (nm).

23. The apparatus according to claim 21, wherein the input wavelength is a wavelength between the range of about 300 nm and about 1300 nm.

24. The apparatus according to claim 13, wherein the optical pulse source generates input optical pulses having a subpicosecond pulse width.

25. The apparatus according to claim 1, wherein the section of HOM fiber produces output optical pulses such that the desired output wavelength is a wavelength within the transparent region of a silica-based fiber.

26. The apparatus according to claim 25, wherein the desired output wavelength is a wavelength between the range of about 300 nm and 1300 nm.

27. The apparatus according to claim 1, wherein the section of HOM fiber produces output optical pulses having a subpicosecond pulse width.

28. The apparatus according to claim 1, further comprising:
a power control system connectedly disposed between the optical pulse source and the section of HOM fiber.

29. The apparatus according to claim 28, wherein the power control system achieves subnanosecond power tuning of the first wavelength.

30. The apparatus as defined in claim 1 wherein the section of HOM fiber is configured to exhibit a positive dispersion (D) of approximately +60 ps/nm-km and an effective area ($A_{eff}$) of 44 µm$^2$ at the desired output wavelength.

31. The apparatus as defined in claim 1 wherein the difference in effective index along the section of HOM fiber between the supported higher-order-mode optical signal and other guided modes is sufficient to provide modal stability for the supported higher-order-mode optical signal.

32. The apparatus as defined in claim 31 where the difference in effective index is greater than $10^{-5}$.

33. The apparatus as defined in claim 1 wherein the apparatus further comprises
a second section of HOM fiber coupled in a cascaded configuration to the section of HOM fiber, where the dispersion and effective area of the second section of HOM fiber are configured to create soliton self-frequency shifting of the propagating optical signal into another, different output wavelength.

34. The apparatus as defined in claim 1 wherein the apparatus further comprises
a second section of HOM fiber coupled in a cascaded configuration to the section of HOM fiber, where the dispersion and effective area of the second section of HOM fiber are configured to create Cherenkov radiation at a second, different output signal wavelength.

* * * * *